(12) United States Patent
Hussack et al.

(10) Patent No.: US 9,771,416 B2
(45) Date of Patent: Sep. 26, 2017

(54) CLOSTRIDIUM DIFFICILE-SPECIFIC ANTIBODIES AND USES THEREOF

(75) Inventors: Greg Hussack, Ottawa (CA); Mehdi Nath Arbabi-Ghahroudi, Ottawa (CA); Roger Mackenzie, Ottawa (CA); Jamshid Tanha, Orleans (CA)

(73) Assignee: National Research Council of Canada, Ottawa (CA)

( * ) Notice: Subject to any disclaimer, the term of this patent is extended or adjusted under 35 U.S.C. 154(b) by 0 days.

(21) Appl. No.: 13/881,398

(22) PCT Filed: Oct. 25, 2011

(86) PCT No.: PCT/CA2011/001201
§ 371 (c)(1),
(2), (4) Date: Apr. 25, 2013

(87) PCT Pub. No.: WO2012/055030
PCT Pub. Date: May 3, 2012

(65) Prior Publication Data
US 2013/0230537 A1    Sep. 5, 2013

Related U.S. Application Data

(60) Provisional application No. 61/406,254, filed on Oct. 25, 2010.

(51) Int. Cl.
*C07K 16/12* (2006.01)
*G01N 33/569* (2006.01)

(52) U.S. Cl.
CPC .... *C07K 16/1282* (2013.01); *G01N 33/56911* (2013.01); *C07K 2317/22* (2013.01); *C07K 2317/35* (2013.01); *C07K 2317/569* (2013.01); *C07K 2317/76* (2013.01); *C07K 2317/92* (2013.01); *C07K 2317/94* (2013.01); *G01N 2333/33* (2013.01)

(58) Field of Classification Search
None
See application file for complete search history.

(56) References Cited

FOREIGN PATENT DOCUMENTS

WO    2006099747    10/2006

OTHER PUBLICATIONS

Skolnick et al. (Trends in Biotechnology 18: 34-39, 2000).*
Greenspan et al. (Nature Biotechnology 7: 936-937, 1999).*
Giusti et al. (Proc. Natl. Acad. Sci. USA. May 1987; 84 (9): 2926-2930).*
Winkler et al (J. Imm., 265:4505-4514, 2000).*
Chien et al. (Proc. Natl. Acad. Sci. USA. Jul. 1989; 86 (14): 5532-5536).*
Caldas et al. (Mol. Immunol. May 2003; 39 (15): 941-952).*
Planche, T., Aghaizu, A., Holliman, R., Riley, P., Poloniecki, J., Breathnach, A., and Krishna, S. (2008) Lancet Infect. Dis. 8, 777-784.
Rupnik, M., Wilcox, M.H., and Gerding, D.N. (2009) Nat. Rev. Microbial. 7, 526-536.
Russmann, H., Panthel, K., Bader, R.C., Schmitt, C., and Schaumann, R. (2007) Eur. J. Clin. Microbial. Infect. Dis. 26, 115-119.
Saerens, D., Conrath, K., Govaert, J., and Muyldermans, S. (2008) J. Mol. Bioi. 377, 478-488.
Salcedo, J., Keates, S., Pothoulakis, C., Warny, M., Castagliuolo, I., LaMont, J.T., and Kelly, C.P. (1997) Gut 41, 366-370.
Salnikova, M.S., Joshi, S.B., Rytting, J.H., Warny, M., and Middaugh, C.R. (2008) J. Pharm. Sci. 97, 3735-3752.
Sloan, L.M., Duresko, B.J., Gustafson, D.R., and Rosenblatt, J.E. (2008) J. Clin. Microbial. 46, 1996-2001.
Songer, J.G. (2004) Anim. Health Res. Rev. 5, 321-326.
Stewart, C.S., MacKenzie, C.R., and Hall, J.C. (2007) Toxicon 49, 699-709.
Tanha, J., Muruganandam, A., and Stanimirovic, D. (2003) Methods Mol. Med. 89, 435-449.
Thompson, J.D., Higgins, D. G., and Gibson, T.J. (1994) Nucleic Acids Res. 22, 4673-4680.
Tjellstrom, B., Stenhammar, L., Eriksson, S., and Magnusson, K.E. (1993) Lancet 341, 701-702.
To, R., Hirama, T., Arbabi-Ghahroudi, M., MacKenzie, R., Wang, P., Xu, P., Ni, F., and Tanha, 5 J. (2005) J. Bioi. Chem. 280,41395-41403.
Turgeon, O.K., Novicki, T.J., Quick, J., Carlson, L., Miller, P., Ulness, B., Cent, A., Ashley, R., Larson, A., Coyle, M., Limaye, A.P., Cookson, B.T., and Fritsche, T.R. {2003) J. Clin. Microbial. 41, 667-670.
Viscidi, R., Laughon, B.E., Yolken, R., So-Linn, P., Moench, T., Ryeder, R.W., and Bartlett, J.G. (1983) J. Infect. Dis. 148, 93-100.
Vu, K.B., Ghahroudi, M.A., Wyns, L., and Muyldermans, S. (1997) Mol. Immunol. 34, 1121-1131.
Warny, M., Fatimi, A., Bostwick, E.F., Laine, D.C., Label, F., LaMont, J.T., Pothoulakis, C., and Kelly, C.P. (1999) Gut 44, 212-217.
Warny, M., Pepin, J., Fang, A., Killgore, G., Thompson, A., Brazier, J., Frost, E., and McDonald, L.C. (2005) Lancet 366, 1079-1084.
Warny, M., Vaerman, J.P., Avesani, V., and Delmee, M. (1994) Infect. Immun. 62, 384-389.
Wesolowski, J., Alzogaray, V., Reyelt, J., Unger, M., Juarez, K., Urrutia, M., Cauerhff, A., Oanguah, W., Rissiek, B., Scheuplein, F., Schwarz, N., Adriouch, S., Boyer, 0., Seman, M., Licea, A., Serreze, D.V., Goldbaum, F.A., Haag, F., and Koch-Nolte, F. (2009) Med. Microbial. Immunol. 198, 157-174.

(Continued)

*Primary Examiner* — Robert A Zeman
(74) *Attorney, Agent, or Firm* — Roula Thomas; Sonia Patenaude

(57) ABSTRACT

The present invention is directed to *Clostridium difficile* toxin-specific antibodies, compositions, and uses thereof. The anti-toxin antibodies may be specific for either TcdA or TcdB. The invention also includes methods of treating a *Clostridium difficile* infection, methods of capturing *Clostridium difficile* toxins, and methods of detecting *Clostridium difficile* toxins.

9 Claims, 34 Drawing Sheets

(56) References Cited

OTHER PUBLICATIONS

Wilcox, N.H. (2004) J. Antimicrob. Chemother. 53, 882-884.
Wilkins, T.D., and Lyerly, D.M. (2003) J. Clin. Microbial. 41, 531-534.
Anderson, G.P., Liu, J.L., Hale, M.L., Bernstein, R.D., Moore, M., Swain, M.D., and Goldman, E.R. (2008) Anal. Chern. 80, 9604-9611.
Arbabi-Ghahroudi, M., MacKenzie, R., and Tanha, J. (2009c) Methods Mol. Bioi. 525, 187-216.
Arbabi-Ghahroudi, M., MacKenzie, R., and Tanha, J. (2010) Methods Mol. Bioi. 634,309-330.
Arbabi-Ghahroudi, M., To, R., Gaudette, N., Hirama, T., Ding, W., MacKenzie, R., and Tanha,J. (2009b) Protein Eng. Des. Sel. 22, 59-66.
Babcock, G.J., Broering, T.J., Hernandez, H.J., Mandell, R.B., Donahue, K., Boatright, N., Stack, A.M., Lowy, 1., Graziano, R., Molrine, D., Ambrosino, D.M., and Thomas, W.O. Jr. (2006) Infect. Immun. 74, 6339-6347.
Bell, A., Wang, Z.J., Arbabi-Ghahroudi, M., Chang, T.A., Durocher, Y., Trojahn, U., Baardsnes,J., Jaramillo, M.L., Li, S., Baral, T.N., O'Connor-McCourt, M., Mackenzie, R., and Zhang, J. (2010) Cancer Lett. 289, 81-90.
Corthier, G., Muller, M.G., Wilkins, T.D., Lyerly, D., and L'Haridon, R. (1991) Infect. Immun. 59, 1192-1195.
De Genst, E., Silence, K., Decanniere, K., Conrath, K., Loris, R., Kinne, J., Muyldermans, S., and Wyns, L. (2006) Proc. Natl. Acad. Sci. U.S.A. 103, 4586-4591.
Doyle, P.J., Arbabi-Ghahroudi, M., Gaudette, N., Furzer, G., Savard, M.E., Gleddie, S., Mclean, M.D., MacKenzie, C. R., and Hall, J.C. (2008) Mol. Immunol. 45, 3703-3713.
Fenner, L., Widmer, A.F., Goy, G., Rudin, S., and Frei, R. (2008) J. Clin. Microbial. 46, 328-330.
Florin, and Thelestam, M. (1983) Biochim. Biophys. Acta 763, 383-392.
Gardiner, D.F., Rosenberg, T., Zaharatos, J., Franco, D., and Ho, D.O. (2009) Vaccine 27, 3598-3604.
Giannasca, P.J., Zhang, Z.X., Lei, W.O., Boden, J.A., Giel, M.A., Monath, T.P., and Thomas, W.O. Jr. (1999) Infect. Immun. 67, 527-538.
Goldman, E.R., Anderson, G.P., Conway, J., Sherwood, L.J., Fech, M., Vo, B., Liu, J.L., and Hayhurst, A. (2008) Anal. Chern. 80, 8583-8591.
Goldman, E.R., Anderson, G.P., Liu, J.L., Delehanty, J.B., Sherwood, L.J., Osborn, L.E., Cummins, L.B., and Hayhurst, A. (2006) Anal. Chern. 78, 8245-8255.
Greco, A., Ho, J.G., Lin, S.J., Palcic, M.M., Rupnik, M., and Ng, K.K. (2006) Nat. Struct. Mol. Bioi. 13,460-461.
Hagihara, Y., Mine, S., and Uegaki, K. (2007) J. Bioi. Chern. 282, 36489-36495.
Hassoun, A., and Ibrahim, F. (2007) Am. J. Geriatr. Pharmacother. 5, 48-51.
Ho, S.N., Hunt, H.D., Horton, R.M., Pullen, J.K., and Pease, L.R. (1989) Gene 77, 51-59.
Hmila, Abdallah, R.B.A., Saerens, D., Benlasfar, Z., Conrath, K., Ayeb, M.E., Muyldermans, S., and Bouhaouala-Zahar, B. (2008) Mol. Immunol. 45, 3847-3856.
Hussack, G., Luo, Y., Veldhuis, L., Hall, J.C., Tanha, J., and MacKenzie, R. (2009) Sensors 9, 5351-5367.
Hussack, G., Hirama, T., Ding, W., MacKenzie, R., and Tanha, J. (2011) PLoS ONE, In press.
Jank, T., and Aktories, K. (2008) Trends Microbial. 16, 222-229.

Jank, T., Giesemann, T., and Aktories, K. (2007) Glycobiology 17, 15R-22R.
Johal, S.S., Lambert, C.P., Hammond, J., James, P.O., Borriello, S.P., and Mahida, Y.R. (2004) J. Clin. Pathol. 57, 973-979.
Johnson, S. (2009) J. Infect. 58, 403-410.
Juang, P., Skledar, S.J., Zgheib, N.K., Paterson, D.L., Vergis, E.N., Shannon, W.O., Ansani, N.T., and Branch, R.A. (2007) Am. J. Infect. Control 35, 131-137.
Katchar, K., Taylor, C.P., Tummala, S., Chen, X, Sheikh, J., and Kelly, C.P. (2007) Clin. Gastroenterol. Hepatol. 5, 707-713.
Keel, M.K., and Songer, J.G. (2007) Vet. Pathol. 44, 814-822.
Kelly, C.P., Chetham, S., Keates, S., Bostwick, E.F., Roush, A.M., Castagliuolo, 1., LaMont J.T., and Pothoulakis, C. (1997) Antimicrob. Agents Chemother. 41, 236-241.
Kelly, C.P., Pothoulakis, C., and LaMount, J.T. (1994) N. Engl. J. Med. 330, 257-262.
Kelly, C.P., Pothoulakis, C., Orellana, J., and LaMont, J.T. (1992} Gastroenterology 102, 35-40 (2009) Nat. Rev. Drug Discov. 8, 442.
Kelly, C.P., Pothoulakis, C., Vavva, F., Castagliuolo, 1., Bostwick, E.F., O'Keane, J.C., Keates, S., and LaMont, J.T. (1996) Antimicrob. Agents Chemother. 40, 373-379.
Kink, J.A., and Williams, J.A. (1998) Infect. Immun. 66, 2018-2025.
Kyne, L., Hamel, M.B., Polavaram, R., and Kelly, C.P. (2002) Clin. Infect. Dis. 34, 346-353.
Kyne, L., Warny, M., Qamar, A., and Kelly, C.P. (2000) N. Engl. J. Med. 340, 390-397.
Kyne, L., Warny, M., Qamar, A., and Kelly, C.P. (2001) Lancet 357, 189-193.
Leffler, D.A., and Lamont, J.T. (2009) Gastroenterology 136, 1899-1912.
Leung, D.Y., Kelly, C.P., Boguniewicz, M., Pothoulakis, C., LaMont, J.T., and Flores, A. (1991) J. Pediatr. 118, 633-637.
Liu, J.L., Anderson, G.P., and Goldman, E.R. (2007a) BMC Biotechnol. 7, 78-88.
Lowy, Molrine, D.C., Leav, B.A., Blair, B.M., Baxter, R., Gerding, D.N., Nichol, G., Thomas, W.O. Jr., Leney, M., Sloan, S., Hay, C.A., and Ambrosino, D.M. (2010) N. Engl. J. Med. 362, 197-205.
Lyerly, D.M., Bostwick, E.F., Binion, S.B., and Wilkins, T.D. (1991} Infect. Immun. 59, 2215-2218.
Lyerly, D.M., Phelps, C.J., Toth, J., and Wilkins, J.D. (1986) Infect. Immun. 54, 70-76.
Lyras, D., O'Connor, J.R., Howarth, P.M., Sambol, S.P., Carter, G.P., Phumoonna, T., Poon, R., Adams, V., Vedantam, G., Johnson, S., Gerding, D.N., and Rood, J.I. (2009} Nature 458, 1176-1179.
McPherson, S., Rees, C.J., Ellis, R., Soo, S., and Panter, S.J. (2006) Dis. Colon Rectum 49, 640-645.
Musher, D.M., Manhas, A., Jain, P., Nuila, F., Waqar, A., Logan, N., Marino, B., Graviss, E.A. (2007) J. Clin. Microbial. 45, 2737-2739.
O'Connor, J.R., Johnson, S., and Gerding, D.N. (2009) Gastroenterology 136, 1913-1924.
Ochsner, U.A., Bell, S.J., O'Leary, A.L., Hoang, T., Stone, K.C., Young, C.L., Critchley, I.A., and Janjic, N. (2009) J. Antimicrob. Chemother. 63, 964-971.
Pace, C. N., Vajdos, F., Fee, L., Grimsley, G., and Gray, T. (1995) Protein Sci. 4, 2411-2423.
Pepin, J., Valiquette, L., and Cossette, B. (2005) CMAJ 173, 1037-1042.
Office Action dated Jun. 2, 2016 for corresponding European Application No. 11835391.8.
Hussack G. et al. Toxin-Specific antibodies for the Treatment of Clostridium difficile: Current Status and future perspectives, Toxins, vol. 2(5), 2010, pp. 998-1010, XP002692188.

* cited by examiner

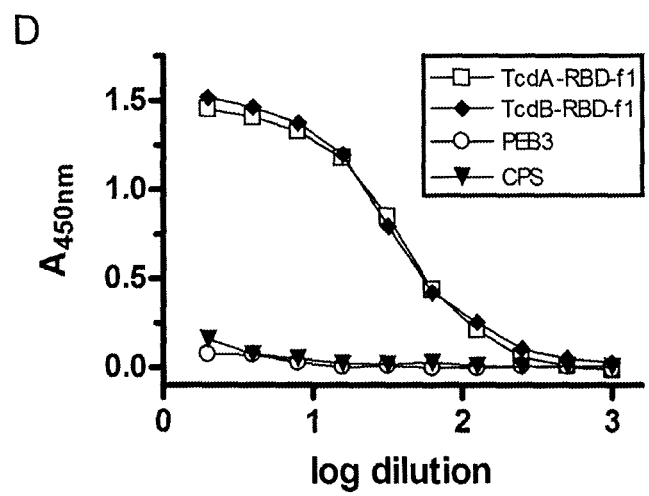
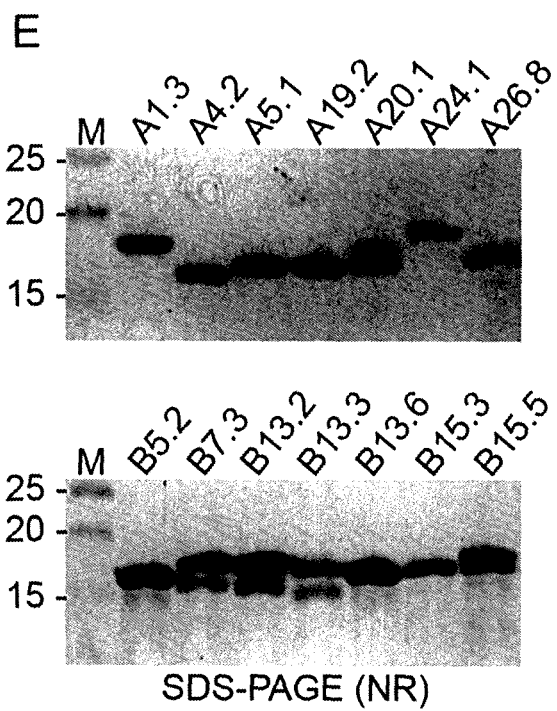
FIG. 1

```
              FR1               CDR1   42    FR2  4950 52  CDR2
                                                 * ** *
A1.3    QVKLEESGGGLVQAGGSLRLSCAAS IRSFSYRNMGW FRQPPGKEREFVAA ITWDGGST
A4.2    QVKLEESGGGLVQAGGSLRLSCAAS GRTFNTLSMGW FRQAPGKEREFVAA VSRSGGST
A5.1    QVKLEESGGGLVQAGGSLRLSCAAS GRTFSMYRMGW FRQAPGKEREFVGV ITRNGSST
A19.2   QVKLEESGGGLVQPGGSLRLSCAAS GRTLSSYIVAW FRQAPGKEREFVAG ISRRGGNS
A20.1   QVQLVESGGGLAQAGGSLRLSCAAS GRTFSMDPMAW FRQPPGKEREFVAA GSSTGRTT
A24.1   QVQLVESGGGLVQAGGSLRLSCAAS IRSFSNRNMGW FRQPPGKEREFVAG ISWGGGST
A26.8   QVKLEESGGGLVQAGGSLRLSCAAS ERTFSRYPVAW FRQAPGAEREFVAV ISSTGTST

B5.2    QVQLVESGGGLVQPGGSLRLSCAAS GNIFSINTMGW YRQAPGKQLELVAA IT-SGGTT
B7.3    QVKLEESGGGLVQPGGSLRLSCAAS GRTASGYGMGW FRQAPGKEREFVAA ISRSGAGT
B13.2   QVKLEESGGGSVQAGGSLRLSCAAS GRDFSTLAMGW FRQAPGKEREFVAT INWSGGTT
B13.3   QVKLEESGGGLVQAGGSLRLSCSAS GSIFSINDMGW YRRAPGKRRELVAA IT-SGGIP
B13.6   QVKLEESGGGLVQAGGSLRLSCSAS GRTFSSGVMGW FRQAPGKQRELVAA IT-TGGST
B15.3   QVQLVESGGGSVQAGGSLRLSCAAS G--LSRYAMAW FRQGTGKEREFVAS TNWSSGNT
B15.5   QVQLVESGGDLVQAGGSLRLSCAAS GSISRISTMGW YRQAPGKQRELVAT IS-TGGTT

FR3                              CDR3
A1.3    RYADSVKGRFTVSRDNAKKTVYLQMNSLKPEDAAVYYC AAGFGHTLATSSDE----YDY
A4.2    YYADSVKGRFTISRDNAKNTVYLQMNSLKPEDTAVYYC AAAATKSNTTAYRLS---FDY
A5.1    YYADSVKGRFTISRDNAKNTVYLQMNSLKPEDTALYYC AATSGSSYLDAAHV----YDY
A19.2   AYVESVKGRFTISRDNAKNTVYLQMNSLKPEDTAVYYC AADGSVAGWGRRSVSVSSYDY
A20.1   YYADSVKGRFTISRDNAKNTVYLQMNSLKPEDTAVYYC AAPYGANWYRDE-----YAY
A24.1   RYADSVKGRFTISRDNAKKTVYLQMNSLKPEDTAVYYC AAEFGHNIATSSDE----YDY
A26.8   YYADSVKGRFTISRDNAKVTVYLQMNNLKREDTAVYFC AVNSQRTRLQDPNE----YDY

B5.2    SYTDSVEGRFTISRDNAKNAVYLQMNSLKAEDTAVYYC NTVKVVGGRLDN-----PDY
B7.3    LNADFVKGRFTISRDNAKNTVYLQMNSLKPEDTAVYYC VARPTKVDRDYATRREM-YNY
B13.2   HYADSVKGRFTISRDNAKNTVYLQMGSLKPEDTAVYYC GRSKYAAGALTRAYD---YNY
B13.3   NYADSVKGRFTISRDNAKNTGYLQMNSLKPEDTAVYYC AAQFGTVAAALRRHE---YDY
B13.6   SYTDSVKGRFTISRDNAKNTVYLQMNSLKPEDTAVYYC NSVAVVGGVIKS------PDY
B15.3   PYADSVKGRFIISRDNAKNTVYLQMNSLKPGDTAIYYC AARKLDVPSRYSQH----YDY
B15.5   NYAESVKGRFTVSRDNAKNTMYLQMNSLKPEDTAVYYC AAGWKVVRGSLE------YEY

FR4
A1.3    WGQGTQVTVSS  SEQ ID NO:88
A4.2    WGQGTQVTVSS  SEQ ID NO:34
A5.1    WGQGTQVTVSS  SEQ ID NO:35
A19.2   WGQGTQVTVSS  SEQ ID NO:36
A20.1   WGQGTQVTVSS  SEQ ID NO:37
A24.1   WGQGTQVTVSS  SEQ ID NO:38
A26.8   WGQGTQVTVSS  SEQ ID NO:39

B5.2    WGQGTQVTVSS  SEQ ID NO:40
B7.3    WGQGTQVTVSS  SEQ ID NO:41
B13.2   WGQGTQVTVSS  SEQ ID NO:89
B13.3   WGQGTQVTVSS  SEQ ID NO:90
B13.6   WGQGTQVTVSS  SEQ ID NO:42
B15.3   WGQGTQVTVSS  SEQ ID NO:43
B15.5   SGQGTQVTVSS  SEQ ID NO:44
```

V$_H$H monomer

Verotoxin B subunit

V$_H$H pentamer

B

A5.1p fractions    A20.1p fractions

M 50
37

25
20

SDS-PAGE (NR)

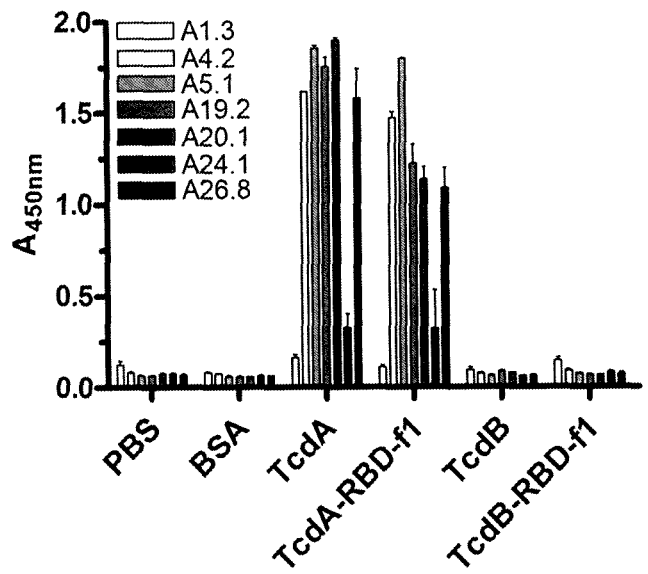
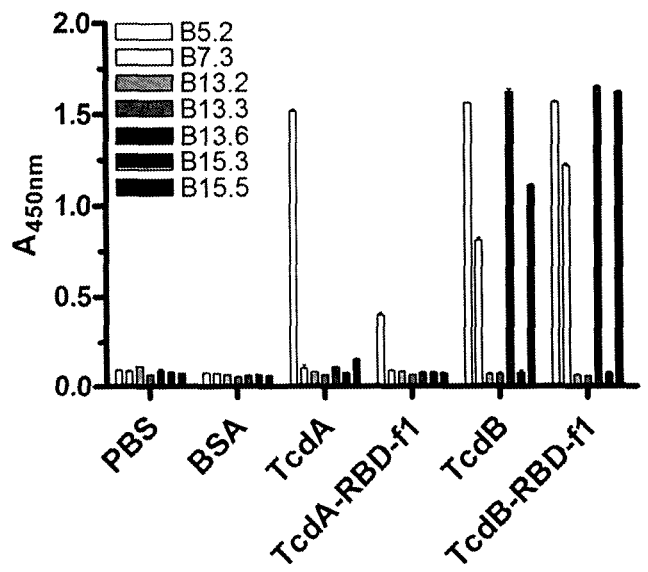
FIG. 4

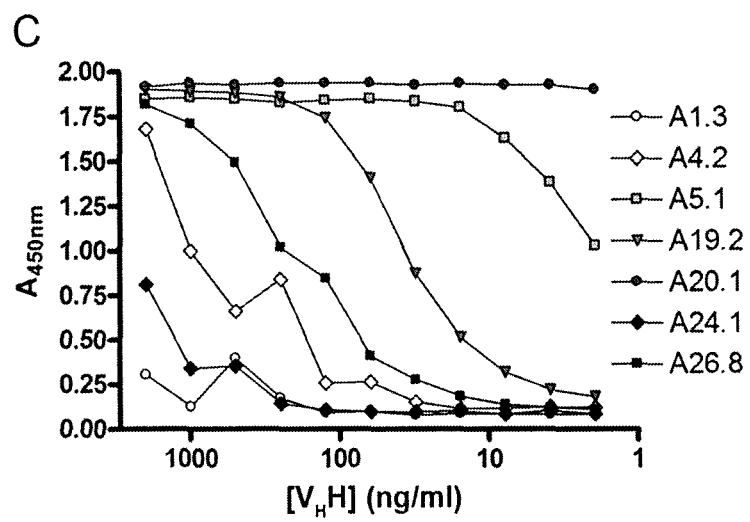
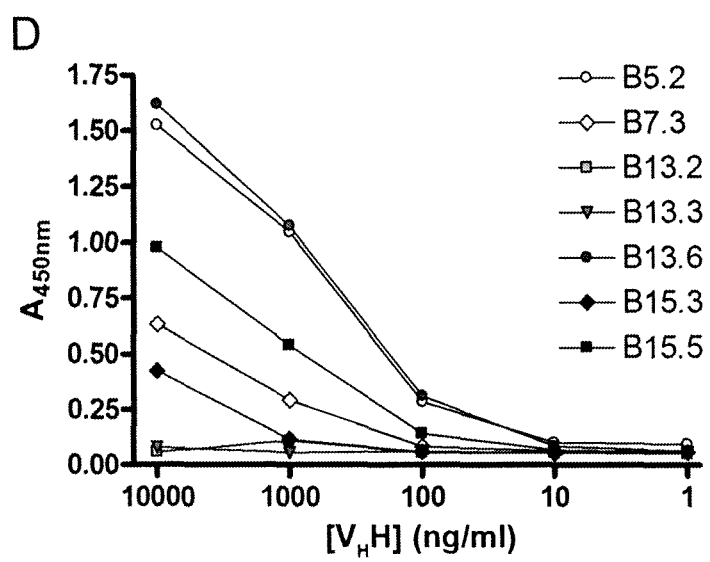
FIG. 4

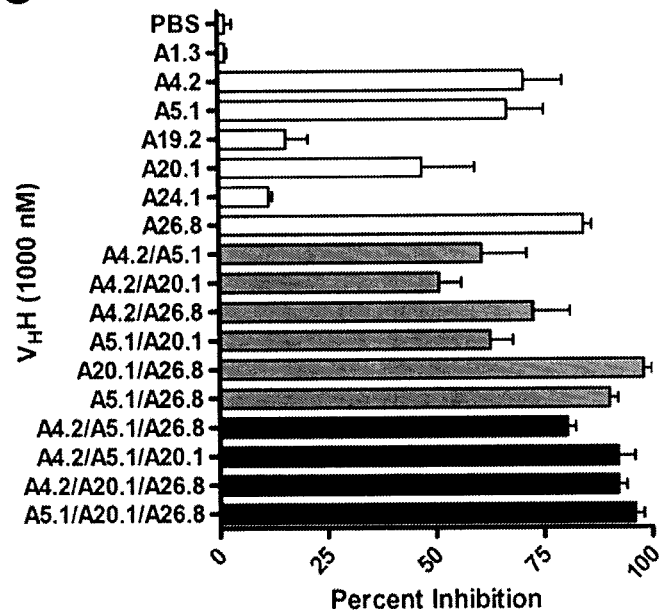
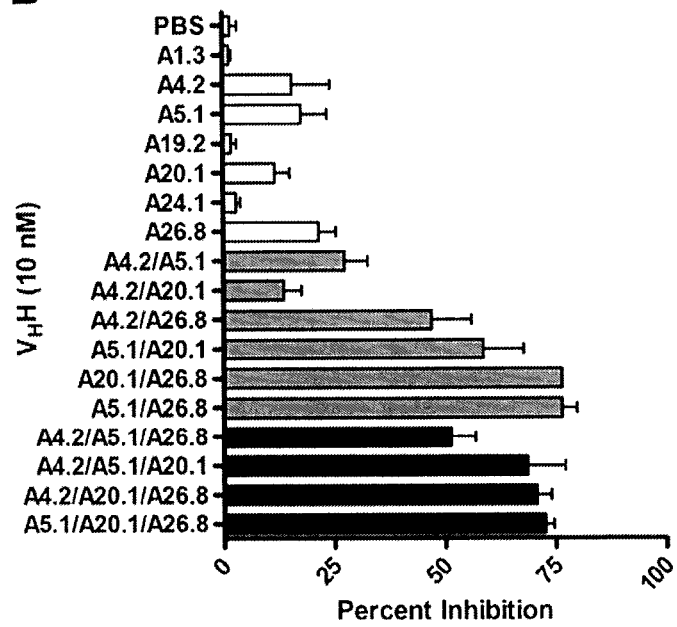
FIG. 8

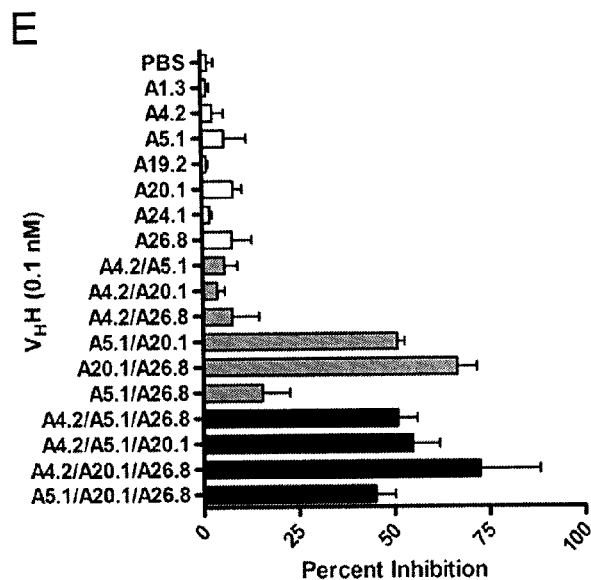
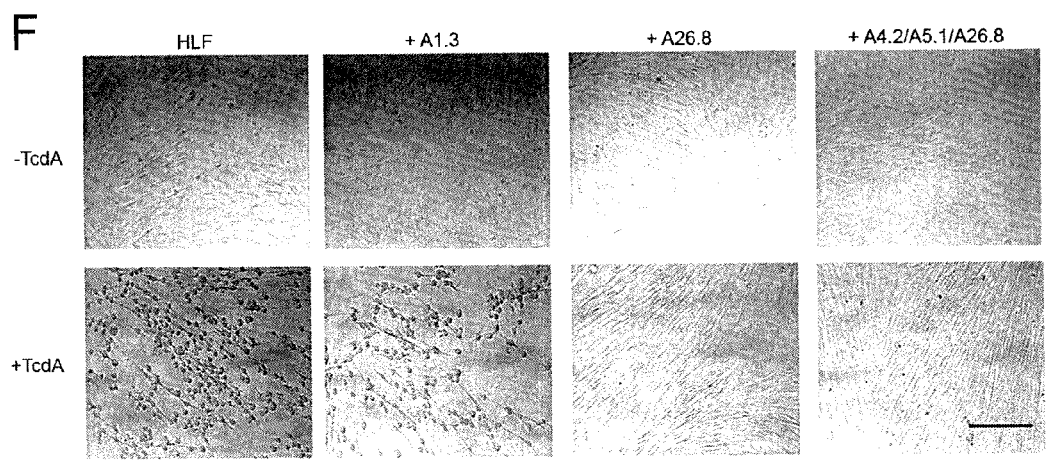
FIG. 8

```
             FR1                              CDR1              FR2          *       CDR2                      FR3                                         CDR3                FR4
WT      QVKLEESGGGLVQAGGSLRLSCAASGRTFNTLSMGWFRQAPGKEREFVAAVSRSGGSTYYADSVKGRFTISRDNAKNTVLQMNSLKPEDTAVYYCAAAATKSNTTAYRLS---FDYWGQGTQVTVSS
A4.2    QVKLEESGGGLVQAGGSLRLSCAASGRTFSMYRMGWFRQAPGKEREFVGVITRNGSSTYYADSVKGRFTISRDNAKNTVLQMNSLKPEDTALYYCAATSGSSYLDAARV---YDYWGQGTQVTVSS
A5.1    QVKLEESGGGLVQPGGSLRLSCAASGRTLSSYIVAWFRQAPGKEREFVAGISRRGNSAYESVKGRFTISRDNAKNTVLQMNSLKPEDTAVYYCAADGSVAGWGRRSVSVSSYDYWGQGTQVTVSS
A19.2   QVQLVESGGGLAQAGGSLRLSCAASGRTFSMDPMAWFRQPPGKEREFVAAGSSTGRTYYADSVKGRFTISRDNAKNTVYLQMNSLKPEDTAVYYCAAPYGANWYRDE---YAYWGQGTQVTVSS
A20.1   QVQLVESGGGLVQAGGSLRLSCAASIRSFSNRNMGWFRQPPGKEREFVAGISWGGSTRYADSVKGRFTISRDNAKKTVLQMNSLKPEDTAVYYCAAEFGHNIATSSDE---YDYWGQGTQVTVSS
A24.1   QVQLVESGGGLVQAGGSLRLSCAASERTFSRYPVAWFRQAPGAEREFVAVISSTGTSTYYADSVKGRFTISRDNAKVTVYLQMNNLKREDTAVYFCAVNSQRTRLQDPNE---YDYWGQGTQVTVSS
A26.8   QVKLEESGGGLVQAGGSLRLSCAASERTFSRYPVAWFRQAPGAEREFVAVISSTGTSTYYADSVKGRFTISRDNAKVTVYLQMNNLKREDTAVYFCAVNSQRTRLQDPNE---YDYWGQGTQVTVSS

Mut
A4.2m   QVKLEESGGGLVQAGGSLRLSCAASGRTFNTLSMGWFRQAPGKEREFVCAVSRSGGSTYYADSVKGRFTCSRDNAKNTVLQMNSLKPEDTAVYYCAAAATKSNTTAYRLS---FDYWGQGTQVTVSS
A5.1m   QVKLEESGGGLVQAGGSLRLSCAASGRTFSMYRMGWFRQAPGKEREFVCVITRNGSSTYYADSVKGRFTCSRDNAKNTVLQMNSLKPEDTALYYCAATSGSSYLDAAHV---YDYWGQGTQVTVSS
A19.2m  QVKLEESGGGLVQPGGSLRLSCAASGRTLSSYIVAWFRQAPGKEREFVCGISRRGNSAYESVKGRFTCSRDNAKNTVLQMNSLKPEDTAVYYCAADGSVAGWGRRSVSVSSYDYWGQGTQVTVSS
A20.1m  QVQLVESGGGLAQAGGSLRLSCAASGRTFSMDPMAWFRQPPGKEREFVCAGSSTGRTYYADSVKGRFTCSRDNAKNTVYLQMNSLKPEDTAVYYCAAPYGANWYRDE---YAYWGQGTQVTVSS
A24.1m  QVQLVESGGGLVQAGGSLRLSCAASIRSFSNRNMGWFRQPPGKEREFVCGISWGGSTRYADSVKGRFTCSRDNAKKTVLQMNSLKPEDTAVYYCAAEFGHNIATSSDE---YDYWGQGTQVTVSS
A26.8m  QVKLEESGGGLVQAGGSLRLSCAASERTFSRYPVAWFRQAPGAEREFVCVISSTGTSTYYADSVKGRFTCSRDNAKVTVYLQMNNLKREDTAVYFCAVNSQRTRLQDPNE---YDYWGQGTQVTVSS

A4.2    SEQ ID NO:34            A4.2m   SEQ ID NO:45
A5.1    SEQ ID NO:35            A5.1m   SEQ ID NO:46
A19.2   SEQ ID NO:36            A19.2m  SEQ ID NO:47
A20.1   SEQ ID NO:37            A20.1m  SEQ ID NO:48
A24.1   SEQ ID NO:38            A24.1m  SEQ ID NO:49
A26.8   SEQ ID NO:39            A26.8m  SEQ ID NO:50
```

FIG. 14

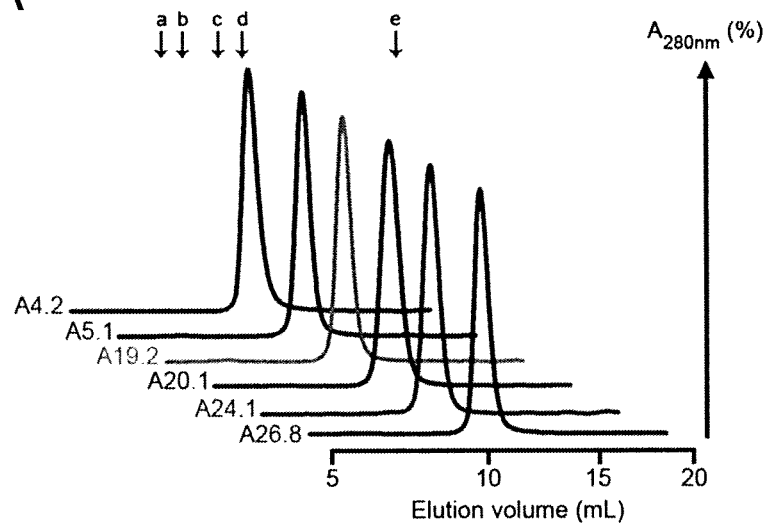
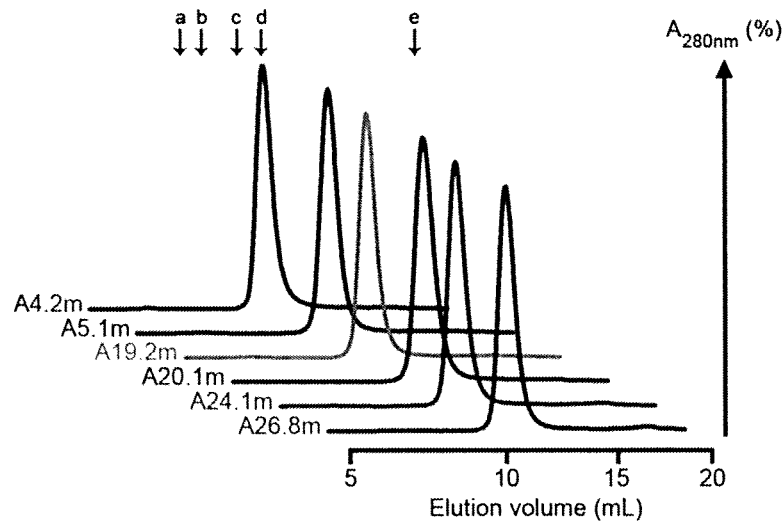
FIG. 17

(B)
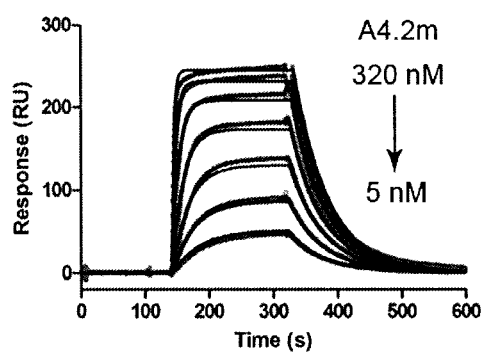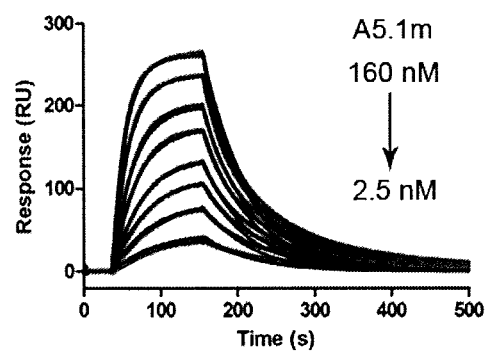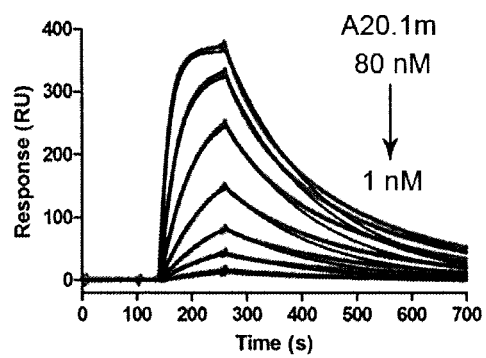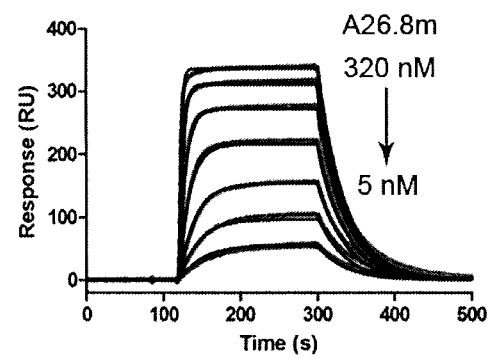
FIG. 17

CLOSTRIDIUM DIFFICILE-SPECIFIC ANTIBODIES AND USES THEREOF

CROSS-REFERENCE TO RELATED APPLICATIONS

This application is a national phase entry of International Patent Application PCT/CA2011/001201 filed Oct. 25, 2011, which claims the benefit of U.S. Provisional Patent Application Ser. No. 61/406,254 filed Oct. 25, 2010, the contents of both of which are incorporated herein in their entirety.

FIELD OF THE INVENTION

The present invention relates to Clostridium difficile-specific antibodies and uses thereof. More specifically, the present invention relates to Clostridium difficile toxin-specific antibodies and uses thereof.

BACKGROUND OF THE INVENTION

Clostridium difficile is a Gram-positive, anaerobic, endospore-forming gastrointestinal pathogen responsible for C. difficile-associated disease (CDAD) in humans and animals with symptoms ranging in severity from mild cases of antibiotic-associated diarrhea to fatal pseudomembranous colitis (Rupnik et al, 2009; Leffler and Lamont, 2009; Songer, 2004; Kelly et al, 1994). Each year in North America, 1-3% of hospitalized patients receiving antibiotics become infected with C. difficile, leading to thousands of deaths and over $1 billion in associated costs to the healthcare system (Wilkins and Lyerly, 2003; Kyne et al, 2002; Kelly et al, 1994). C. difficile produces two primary virulence factors, toxin A (TcdA) and toxin B (TcdB), which are large (308 kDa and 269 kDa, respectively), single-subunit exotoxins composed of a catalytic, a translocation and a cell-receptor binding domain (RBD) (Jank and Aktories, 2008; Jank et al, 2007). Recently it was suggested TcdB is solely responsible for C. difficile virulence (Lyras et al, 2009), although earlier studies have shown both anti-TcdA and anti-TcdB monoclonal antibodies (mAbs) were required for full protection of hamsters from CDAD (Babcock et al, 2006; Kink and Williams, 1998) and anti-TcdA mAbs were required for protection in mice (Corthier et al, 1991).

The current approach for treating most CDAD infections involves administration of antibiotics, most commonly metronidazole or vancomycin (Leffler and Lamont, 2009). Antibiotic treatment places selection pressure on the organism, can lead to antibiotic resistance, and suppresses or eliminates beneficial commensal microbes. However, there are several other emerging challenges warranting the development of novel therapeutics. First, there is no acute CDAD treatment targeting TcdA/B. These toxins are responsible for loss of epithelial barrier function in the colon by disrupting tight junctions and increasing membrane permeability, causing diarrhea and promoting severe inflammation (Rupnik et al, 2009; Jank and Aktories, 2008). Second, hypervirulent strains of C. difficile, such as the NAP1/027 isolate, overexpress TcdA and TcdB (Warny et al, 2005) and have been associated with increased mortality rates and disease severity (O'Connor et al, 2009; Pépin et al, 2005). Third, an estimated 20-25% of patients suffering from CDAD experience symptomatic relapse after the initial infection is cleared, with 45% of these patients prone to subsequent relapses (Johnson, 2009). Taken together, there is a need for non-antibiotic based reagents which target and inhibit TcdA and TcdB for CDAD therapy.

Individuals who are asymptomatic C. difficile carriers and patients who experience mild cases of CDAD tend to possess high anti-toxin A titers (Kyne et al, 2001; Kyne et al, 2000; Warny et al, 1994; Viscidi et al, 1983). Conversely, patients susceptible to relapsing C. difficile infection have low anti-TcdA immunoglobulin titers, specifically IgM, IgG2 and IgG3 isotypes (Katchar et al, 2007; Kyne et al, 2001). TcdA-neutralizing secretory IgA antibodies are also thought to play a role in regulating CDAD severity (Johal et al 2004; Kelly et al 1992). Therefore, the introduction of anti-toxin antibodies to patients suffering from severe C. difficile infection may be a therapeutically useful approach.

A limited number of animal and human studies have illustrated the effectiveness of anti-toxin Abs for treatment of CDAD. Babcock et al (2006) intravenously administered anti-TcdA and anti-TcdB mAbs to hamsters and found a significant reduction in hamster mortality in prophylactic, primary disease and relapse models when both anti-toxin mAbs were administered. A recently completed clinical trial involving these two humanized mAbs appears promising (Lowy et al, 2010). In another study, intravenous administration of anti-TcdA mAbs raised against the RBD followed by oral challenge with C. difficile resulted in protection of mice (Corthier et al, 1991). Elsewhere, a toxoid vaccine given by the intraperitoneal route to hamsters conferred protection against oral C. difficile challenge (Giannasca et al, 1999) and mice vaccinated with DNA encoding the TcdA RBD resulted in full protection from oral TcdA challenge (Gardiner et al, 2009). In humans, a number of uncontrolled studies have reported intravenous immunoglobulin (IVIG) therapy to be successful for the treatment of severe CDAD (Juang et al, 2007; Hassoun and Ibrahim, 2007; McPherson et al, 2006; Wilcox, 2004; Salcedo et al, 1997; Leung et al, 1991). IVIG involves administration of high concentrations (150-400 mg/kg) of human immunoglobulins from healthy donors which are thought to contain neutralizing anti-toxin antibodies as an estimated 60% of healthy adults have detectable TcdA- and TcdB-specific serum IgG antibodies (Viscidi et al, 1983).

Given that C. difficile toxins rely on attachment to epithelial cells for entry (Jank and Aktories, 2008; Jank et al, 2007), neutralizing the toxins within the lower gastrointestinal tract with antibodies may block the first step in CDAD pathogenesis. In animals, orally administered bovine immunoglobulin concentrate (BIC) containing TcdA and TcdB neutralizing IgGs were able to prevent hamster mortality when used as a propholyactic (Lyerly et al, 1991) and protected rats from the enterotoxic effects of TcdA in vivo (Kelly et al, 1996). Chicken IgY antibodies specific for toxin RBDs were shown to reduce hamster mortality when administered orally to infected animals (Kink and Williams, 1998). In humans, there have been limited reports on CDAD therapy with orally delivered Abs. Tjellströem et al (1993) reported the successful treatment of a 3½ year old boy suffering from severe CDAD with IgA antibody orally. Warny et al (1999) and Kelly et al (1997) examined the passage of anti-toxin bovine IgG through the human gastrointestinal tract and found a significant reduction in IgG activity, likely due to proteolytic degradation within the upper gastrointestinal tract. The limited success of both oral and systemic anti-toxin immunotherapy in clinical settings has likely been hampered by the high immunoglobulin dose requirements (150-400 mg/kg), the associated costs of these doses, and a lack of published clinical data showing the effectiveness of these treatments.

Despite such advances, there remains a need in the art for a safe and effective therapeutic for treating *C. difficile*-associated disease as well as for sensitive and effective reagents for the detection of toxins A and B, the factors responsible for *C. difficile*-associated disease.

SUMMARY OF THE INVENTION

The present invention relates to *Clostridium difficile*-specific antibodies and uses thereof. More specifically, the present invention relates to *Clostridium difficile* toxin-specific antibodies and uses thereof.

The present invention provides an isolated or purified antibody or fragment thereof, comprising
- a sequence of complementarity determining region (CDR) 1 selected from GRTFNTLS (SEQ ID NO:1); GRTFSMYR (SEQ ID NO:2); GRTLSSYI (SEQ ID NO:3); GRTFSMDP (SEQ ID NO:4); IRSFSNRN (SEQ ID NO:5); and ERTFSRYP (SEQ ID NO:6);
- a sequence of CDR2 selected from VSRSGGST (SEQ ID NO:7); ITRNGSST (SEQ ID NO:8); ISRRGGNS (SEQ ID NO:9); GSSTGRTT (SEQ ID NO:10); ISWGGGST (SEQ ID NO:11); and ISSTGTST (SEQ ID NO:12); and
- a sequence of CDR3 selected from AAAATKSNTTAYRLSFDY (SEQ ID NO:13); AATSGSSYLDAAHVYDY (SEQ ID NO:14); AADGSVAGWGRRSVSVSSYDY (SEQ ID NO:15); AAAPYGANWYRDEYAY (SEQ ID NO:16); AAEFGHNIATSSDEYDY (SEQ ID NO:17); and AVNSQRTRLQDPNEYDY (SEQ ID NO:18), wherein the antibody or fragment thereof is specific for TcdA. The isolated or purified antibody or fragment thereof as described above may be selected from the group consisting of:

- an isolated or purified antibody or fragment thereof comprising a sequence of CDR 1 of GRTFNTLS (SEQ ID NO:1); CDR2 of VSRSGGST (SEQ ID NO:7); and CDR3 of AAAATKSNTTAYRLSFDY (SEQ ID NO:13);
- an isolated or purified antibody or fragment thereof comprising a sequence of CDR 1 of GRTFSMYR (SEQ ID NO:2); CDR2 of ITRNGSST (SEQ ID NO:8); and CDR3 of AATSGSSYLDAAHVYDY (SEQ ID NO:14);
- an isolated or purified antibody or fragment thereof comprising a sequence of CDR 1 of GRTLSSYI (SEQ ID NO:3); CDR2 of ISRRGGNS (SEQ ID NO:9); and CDR3 of AADGSVAGWGRRSVSVSSYDY (SEQ ID NO:15);
- an isolated or purified antibody or fragment thereof comprising a sequence of CDR 1 of GRTFSMDP (SEQ ID NO:4); CDR2 of GSSTGRTT (SEQ ID NO:10); and CDR3 of AAAPYGANWYRDEYAY (SEQ ID NO:16);
- an isolated or purified antibody or fragment thereof comprising a sequence of CDR 1 of IRSFSNRN (SEQ ID NO:5); CDR2 of ISWGGGST (SEQ ID NO:11); and CDR3 of AAEFGHNIATSSDEYDY (SEQ ID NO:17); or
- an isolated or purified antibody or fragment thereof comprising a sequence of CDR 1 of ERTFSRYP (SEQ ID NO:6); CDR2 of ISSTGTST (SEQ ID NO:12); and CDR3 of AVNSQRTRLQDPNEYDY (SEQ ID NO:18).

The isolated or purified antibody or fragment thereof described above may comprise a sequence selected from the group consisting of:

```
                                                   (SEQ ID NO: 34)
QVKLEESGGGLVQAGGSLRLSCAASGRTFNTLSMGWFRQAPGKEREFVAAVSRSGGST

YYADSVKGRFTISRDNAKNTVYLQMNSLKPEDTAVYYCAAAATKSNTTAYRLSFDYWGQG

TQVTVSS;

(SEQ ID NO: 35)
QVKLEESGGGLVQAGGSLRLSCAASGRTFSMYRMGWFRQAPGKEREFVGVITRNGSSTY

YADSVKGRFTISRDNAKNTVYLQMNSLKPEDTALYYCAATSGSSYLDAAHVYDYWGQGT

QVTVSS;

(SEQ ID NO: 36)
QVKLEESGGGLVQPGGSLRLSCAASGRTLSSYIVAWFRQAPGKEREFVAGISRRGGNSAY

VESVKGRFTISRDNAKNTVYLQMNSLKPEDTAVYYCAADGSVAGWGRRSVSVSSYDYWG

QGTQVTVSS;

(SEQ ID NO: 37)
QVQLVESGGGLAQAGGSLRLSCAASGRTFSMDPMAWFRQPPGKEREFVAAGSSTGRTT

YYADSVKGRFTISRDNAKNTVYLQMNSLKPEDTAVYYCAAAPYGANWYRDEYAYWGQGT

QVTVSS;

(SEQ ID NO: 38)
QVQLVESGGGLVQAGGSLRLSCAASIRSFSNRNMGWFRQPPGKEREFVAGISWGGGST

RYADSVKGRFTISRDNAKKTVYLQMNSLKPEDTAVYYCAAEFGHNIATSSDEYDYWGQGT

QVTVSS;

(SEQ ID NO: 39)
QVKLEESGGGLVQAGGSLRLSCAASERTFSRYPVAWFRQAPGAEREFVAVISSTGTSTYY
```

```
                                                    -continued
ADSVKGRFTISRDNAKVTVYLQMNNLKREDTAVYFCAVNSQRTRLQDPNEYDYWGQGTQ

VTVSS;

(SEQ ID NO: 45)
QVKLEESGGGLVQAGGSLRLSCAASGRTFNTLSMGWFRQAPGKEREFVCAVSRSGGST

YYADSVKGRFTCSRDNAKNTVYLQMNSLKPEDTAVYYCAAAATKSNTTAYRLSFDYWGQ

GTQVTVSS;

(SEQ ID NO: 46)
QVKLEESGGGLVQAGGSLRLSCAASGRTFSMYRMGWFRQAPGKEREFVCVITRNGSSTY

YADSVKGRFTCSRDNAKNTVYLQMNSLKPEDTALYYCAATSGSSYLDAAHVYDYWGQGT

QVTVSS;

(SEQ ID NO: 47)
QVKLEESGGGLVQPGGSLRLSCAASGRTLSSYIVAWFRQAPGKEREFVCGISRRGGNSA

YVESVKGRFTCSRDNAKNTVYLQMNSLKPEDTAVYYCAADGSVAGWGRRSVSVSSYDY

WGQGTQVTVSS;

(SEQ ID NO: 48)
QVQLVESGGGLAQAGGSLRLSCAASGRTFSMDPMAWFRQPPGKEREFVCAGSSTGRTT

YYADSVKGRFTCSRDNAKNTVYLQMNSLKPEDTAVYYCAAAPYGANWYRDEYAYWGQG

TQVTVSS;

(SEQ ID NO: 49)
QVQLVESGGGLVQAGGSLRLSCAASIRSFSNRNMGWFRQPPGKEREFVCGISWGGGST

RYADSVKGRFTCSRDNAKKTVYLQMNSLKPEDTAVYYCAAEFGHNIATSSDEYDYWGQG

TQVTVSS;
and
                                                                    (SEQ ID NO: 50)
QVKLEESGGGLVQAGGSLRLSCAASERTFSRYPVAWFRQAPGAEREFVCVISSTGTSTYY

ADSVKGRFTCSRDNAKVTVYLQMNNLKREDTAVYFCAVNSQRTRLQDPNEYDYWGQGT

QVTVSS,
``` or a sequence substantially identical thereto.

In another aspect, the present invention provides an isolated or purified antibody or fragment thereof, comprising
  a sequence of complementarity determining region (CDR) 1 selected from GNIFSINT (SEQ ID NO:19); GRTASGYG (SEQ ID NO:20); GRTFSSGV (SEQ ID NO:21); GLSRYA (SEQ ID NO:22); and GSISRIST (SEQ ID NO:23);
  a sequence of CDR2 selected from ITSGGTT (SEQ ID NO:24); ISRSGAGT (SEQ ID NO:25); ITTGGST (SEQ ID NO:26); TNWSSGNT (SEQ ID NO:27); and ISTGGTT (SEQ ID NO:28); and
  a sequence of CDR3 selected from NTVKVVGGRLDNPDY (SEQ ID NO:29); VARPTKVDRDYATRREMYNY (SEQ ID NO:30); NSVAVVGGVIKSPDY (SEQ ID NO:31); AARKLDVPSRYSQHYDY (SEQ ID NO:32); and AAGVVKWRGSLEYEY (SEQ ID NO:33),
wherein the antibody or fragment thereof is specific for TcdB. The isolated or purified antibody or fragment thereof as just described may be selected from the group consisting of:
  an isolated or purified antibody or fragment thereof comprising a sequence of CDR 1 of GNIFSINT (SEQ ID NO:19); CDR2 of ITSGGTT (SEQ ID NO:24); and CDR3 of NTVKVVGGRLDNPDY (SEQ ID NO:29);

an isolated or purified antibody or fragment thereof comprising a sequence of CDR 1 of GRTASGYG (SEQ ID NO:20); CDR2 of ISRSGAGT (SEQ ID NO:25); and CDR3 of VARPTKVDRDYATRREMYNY (SEQ ID NO:30);

an isolated or purified antibody or fragment thereof comprising a sequence of CDR 1 of GRTFSSGV (SEQ ID NO:21); CDR2 of ITTGGST (SEQ ID NO:26); and CDR3 of NSVAVVGGVIKSPDY (SEQ ID NO:31);

an isolated or purified antibody or fragment thereof comprising a sequence of CDR 1 of GLSRYA (SEQ ID NO:22); CDR2 of TNWSSGNT (SEQ ID NO:27); and CDR3 of AARKLDVPSRYSQHYDY (SEQ ID NO:32); or an isolated or purified antibody or fragment thereof comprising a sequence of CDR 1 of GSISRIST (SEQ ID NO:23); CDR2 of ISTGGTT (SEQ ID NO:28); and CDR3 of AAGWKVVRGSLEYEY (SEQ ID NO:33).

The isolated or purified antibody or fragment thereof as described above may comprise a sequence selected from the group consisting of:

(SEQ ID NO: 40)
QVQLVESGGGLVQPGGSLRLSCAASGNIFSINTMGWYRQAPGKQLELVAAITSGGTTSYT
DSVEGRFTISRDNAKNAVYLQMNSLKAEDTAVYYCNTVKVVGGRLDNPDYWGQGTQVTV
SS;

(SEQ ID NO: 41)
QVKLEESGGGLVQPGGSLRLSCAASGRTASGYGMGWFRQAPGKEREFVAAISRSGAGTL
NADFVKGRFTISRDNAKNTVYLQMNSLKPEDTAVYYCVARPTKVDRDYATRREMYNYWG
QGTQVTVSS;

(SEQ ID NO: 42)
QVKLEESGGGLVQAGGSLRLSCSASGRTFSSGVMGWFRQAPGKQRELVAAITTGGSTSY
TDSVKGRFTISRDNAKNTVYLQMNSLKPEDTAVYYCNSVAVVGGVIKSPDYWGQGTQVTV
SS;

(SEQ ID NO: 43)
QVQLVESGGGSVQAGGSLRLSCAASGLSRYAMAWFRQGTGKEREFVASTNWSSGNTPY
ADSVKGRFIISRDNAKNTVYLQMNSLKPGDTAIYYCAARKLDVPSRYSQHYDYWGQGTQV
TVSS;

(SEQ ID NO: 44)
QVQLVESGGDLVQAGGSLRLSCAASGSISRISTMGWYRQAPGKQRELVATISTGGTTNYA
ESVKGRFTVSRDNAKNTMYLQMNSLKPEDTAVYYCAAGWKVVRGSLEYEYSGQGTQVTV
SS;

(SEQ ID NO: 51)
QVQLVESGGGLVQPGGSLRLSCAASGNIFSINTMGWYRQAPGKQLELVCAITSGGTTSYTDS
VEGRFTCSRDNAKNAVYLQMNSLKAEDTAVYYCNTVKVVGGRLDNPDYWGQGTQVTVSS,
referred to herein as B5.2m;

(SEQ ID NO: 52)
QVKLEESGGGLVQPGGSLRLSCAASGRTASGYGMGWFRQAPGKEREFVCAISRSGAGTLN
ADFVKGRFTCSRDNAKNTVYLQMNSLKPEDTAVYYCVARPTKVDRDYATRREMYNYWGQG
TQVTVSS,
referred to herein as B7.3m;

(SEQ ID NO: 53)
QVKLEESGGGLVQAGGSLRLSCSASGRTFSSGVMGWFRQAPGKQRELVCAITTGGSTSYTD
SVKGRFTCSRDNAKNTVYLQMNSLKPEDTAVYYCNSVAVVGGVIKSPDYWGQGTQVTVSS,
referred to herein as B13.6m;

(SEQ ID NO: 54)
QVQLVESGGGSVQAGGSLRLSCAASGLSRYAMAWFRQGTGKEREFVCSTNWSSGNTPYAD
SVKGRFICSRDNAKNTVYLQMNSLKPGDTAIYYCAARKLDVPSRYSQHYDYWGQGTQVTVS
S,
referred to herein as B15.3m; and (SEQ ID NO: 55)
QVQLVESGGDLVQAGGSLRLSCAASGSISRISTMGWYRQAPGKQRELCATISTGGTTNYAES
VKGRFTCSRDNAKNTMYLQMNSLKPEDTAVYYCAAGWKVVRGSLEYEYSGQGTQVTVS,
referred to herein as B15.5m, or a sequence substantially identical thereto.

The isolated or purified antibody or fragment thereof as described above may be a single-domain antibody (sdAb); the sdAb may be of camelid origin.

The isolated or purified antibody or fragment thereof of as described herein may be in a multivalent display format.

The isolated or purified antibody or fragment thereof as described herein may be immobilized onto a surface.

The isolated or purified antibody or fragment thereof of the present invention may be linked to a cargo molecule; the cargo molecule may be a detectable agent, a therapeutic, a drug, a peptide, a protease, an enzyme, a carbohydrate moiety, or a cytotoxic agent; one or more liposomes loaded with a detectable agent, a therapeutic, a drug, a peptide, an enzyme, or a cytotoxic agent; or one or more nanoparticle, nanowire, nanotube, or quantum dots.

The present invention further encompasses a nucleic acid molecule encoding the isolated or purified antibody or fragment thereof as described above. The present invention also includes a vector comprising the nucleic acid molecule just described.

Also provided is a composition comprising one or more than one isolated or purified antibody or fragment thereof of the present invention and a pharmaceutically-acceptable carrier, diluent, or excipient.

The present invention further provides a method of treating a *Clostridium difficile* infection, comprising administering the isolated or purified antibody or fragment thereof of the present invention or the composition of described above to a subject in need thereof.

In another aspect, there is provided a method of capturing *Clostridium difficile* toxins, comprising contacting a sample with one or more than one isolated or purified antibody or fragment thereof of the present invention immobilized onto a surface, and allowing the toxin(s) to bind to the isolated or purified antibody or fragment thereof. The method just described may further comprise identifying the toxin by mass spectrometric methods and/or eluting the bound toxin.

The present invention additionally provides a method of detecting *Clostridium difficile* toxins, comprising contacting a sample with one or more than one isolated or purified antibody or fragment thereof linked to a cargo molecule, and detecting the bound antibody or fragment thereof using a suitable imaging or detection technology. The cargo molecule may be a detectable agent.

The present invention provides isolated llama single-domain antibodies ($V_HHs$) capable of binding, detecting, capturing, and/or neutralizing *C. difficile* TcdA and TcdB. Without wishing to be bound by theory, $V_HHs$ targeting the toxin's receptor binding domain (RBD) may block the toxin-receptor interaction, thereby preventing toxin entry into the host cell; a critical initial step in the TcdA/B mechanism of action (Jank and Aktories, 2008). To do so, a hyperimmunized llama $V_HH$ phage display library was constructed and panned with recombinant RBD fragments. The isolated $V_HHs$ were then characterized for their ability to bind native toxins and recombinant RBD fragments and the nature and relative positioning of epitopes. In addition, the ability of $V_HHs$ to neutralize toxins in an in vitro cell cytotoxicity assay was assessed.

Several TcdA-specific $V_HHs$ capable of neutralizing TcdA in vitro through high-affinity interactions with TcdA-RBD were found. $V_HHs$ are extremely stable antigen-binding domains that are expressed at high-yields in recombinant organisms and are capable of neutralizing infectious disease-related targets (Wesolowski et al, 2009). With respect to CDAD therapy, $V_HHs$ could be administered systemically to target TcdA and TcdB as they share high sequence homology with human $V_H$ domains, thus are well-tolerated in humans (Vu et al, 1997; www.Ablynx.com). Enhanced toxin neutralizing efficacy may be obtained by increasing their blood circulation half lives, size and avidity using various techniques, including chimeric formats of anti-TcdA $V_HHs$ linked to an Fc domain, generation of bi- or tri-specific antibody fusions with two or three anti-TcdA $V_HHs$ recognizing unique epitopes, PEGylation, fusion to serum albumin, or fusion to serum albumin-specific antibody fragments. By targeting *C. difficile* virulence factors such as TcdA/B, selection pressure is removed from the organism, decreasing the chance of antibiotic resistance. A mutation in the RBD, which is conserved among *C. difficile* isolates including hypervirulent 027 ribotype strains, is unlikely to benefit the organism and in the event it does occur, the toxin may lose its ability to enter host cells. As such, anti-TcdA/B $V_HHs$ are logical agents to explore for CDAD therapy.

In order to improve the $V_HHs$' biophysical properties, the *C. difficile* TcdA-specific $V_HHs$ were engineered to insert a non-canonical disulfide bond by introducing Ala/Gly$^{54}$→Cys$^{54}$ and Ile$^{78}$→Cys$^{78}$ mutations, allowing for the formation of a second, non-native disulfide bond between FR2 and FR3 in the $V_HH$ hydrophobic core. Disulfide bond formation was confirmed using a combination of proteolytic and chemical digestion coupled with MS$^2$ to precisely identify $V_HH$ peptide fragments harboring the introduced disulfide bond. The mutant antibodies were compared to their wild-type counterparts with respect to yield, solubility, affinity for TcdA, thermal unfolding at neutral and acidic pH and protease resistance. Mutant $V_HHs$ were found to be soluble, non-aggregating monomers, possessing similar affinity constants to that of WT $V_HHs$. SPR binding experiments revealed most mutant $V_HHs$ possessed 1- to 5-fold weaker affinity constants relative to wild-type, which is consistent with other reports in the art.

CD spectroscopy was used to compare wild-type and mutant $V_HH$ secondary structure, tertiary structure, thermal stability ($T_m$ and $T_{onset}$), and thermal refolding efficiency (TRE). Comparisons of $V_HH$ secondary and tertiary structure with far-UV and near-UV CD spectroscopy strongly suggested structural differences between wild-type and mutants, at both neutral and acidic pH. For all mutants, peak intensity and selective peak minima shifts were observed, although the overall spectral profiles remained very similar in all wild type/mutant pairs. More specifically, mutants consistently showed rightward peak shifts in the peak range of 230 nm-235 nm (far-UV CD spectra) and around 297 nm (near-UV CD spectra) compared to wild type $V_HHs$. Such patterns may be used as signatures that could be used to quickly identify $V_HHs$ containing a properly formed non-canonical disulfide bond, as could SDS-PAGE motility values since, compared to wild type $V_HHs$, mutants consistently moved slower in SDS-PAGE gels. Thus, the far- and near-UV CD spectral data suggests the introduced disulfide bond changes the structure of $V_HHs$. This is consistent with the observed perturbations in affinities and specificities and increased GI protease resistance of the mutant $V_HHs$ compared to the wild types.

CD spectroscopy thermal denaturation experiments were performed to show a profound and significant (p<0.05) increase in the $T_m$s and $T_{onset}$s of mutant $V_HHs$ at both neutral and acidic pH. Increases in midpoint temperature of unfolding ($T_m$) ranging from ~4 to ~12° C. were observed for all mutants, at both neutral and acidic pH. Without wishing to be bound by theory, for the mutant $V_HHs$ with a higher thermostability gain, the non-canonical disulfide linkage may have been a better fit to overall fold. For example, A19.2m and A24.1m showed the lowest thermostability gains and this would explain why they were transformed into non-specific binders upon mutation. For A4.2m on the other hand, the non-canonical disulfide linkage seems to be a natural fit, as it increased its $T_m$ the most (by almost 12° C.) and significantly improved GI protease resistance (with the highest increase in pepsin resistance), all without adversely affecting the $K_D$.

Digestion of the $V_HHs$ with major gastrointestinal proteases at biologically relevant concentrations revealed a significant (p<0.05) increase in pepsin resistance for all mutants; however, increases in resistance profiles to chymotrypsin and trypsin were not as universal. Each wild-type and mutant $V_HH$ pair possessed an identical number of theoretical protease cleavage sites (data not shown); thus it seems that the added disulfide bond leads to a more compact and thermodynamically stable $V_HH$ structure, preventing pepsin and chymotrypsin from accessing proteolytic cleavage sites. $V_HH$ refolding was also examined using CD spectroscopy. While wild-type refolding was better than mutant $V_HH$ refolding at neutral pH the reverse was true under stringent conditions (acidic pH). At acidic pH, 5 of 6 mutant $V_HHs$ possessed greater refolding efficiency than wild-type after complete thermal denaturation with the majority essentially showing reversible thermal unfolding.

The introduction of the Cys54/Cys78 disulfide linkage into $V_HHs$ led to increases in both $T_m$ and thermodynamic stability. Proteins with higher $T_n$, are also less likely to unfold [62]. These may be the reasons why the present mutants were more resistant to acid-induced unfolding at 37° C., supported by the higher $T_{onset}$s and pepsin resistance of the mutant $V_HHs$. This benefit is not realized for mutants against trypsin, possibly because their cleavage sites are at hydrophilic residues (Lys or Arg), which may be in more exposed regions of the $V_HH$, possibly located in the CDR regions. Further, these regions would not be protected by stabilizing the core of the structure. An increase in $T_{onset}$ temperatures for mutants at the physiological condition representative of the stomach (pH 2.0 and 37° C.) to values significantly above 37° C. ($T_{onsets}$ from 45° C.-53° C.) was observed. This indicates that the mutants should remain fully folded at 37° C. in the stomach, hence resisting pepsin degradation (and denaturation) to a higher extent than wild type $V_HHs$, which is supported by the pepsin digestion experiments herein.

The toxin A neutralizing efficacy of the disulfide bond mutant $V_HHs$ was 3-4 fold weaker compared to the wild-type $V_HHs$ in toxin A neutralization in cell-based assays, presumably a reflection in the reduced affinities of 3 of 4 $V_HHs$ for the toxin. Under stringent conditions in vivo, the lower affinity mutants may actually be more efficacious than the higher affinity wild-type $V_HHs$ due to their greater stability.

It is presently shown that the introduction of a second disulfide bond into the hydrophobic core of a panel of llama $V_HHs$ increased thermal stability and GI protease resistance; the approach is both effective and general. While affinity, specificity, and expression yield may be reduced, the mutants comprising additional disulfide bond outperformed the wild-type $V_HHs$ under more stringent physiological conditions; this far outweighs the reductions in affinity.

Protein-based oral therapeutics have several conceived advantages over systemic administration: convenience, patience compliance, lower cost, pain-free administration, drug purity, flexibility in production source (i.e., bacterial, plant, etc.), and fewer concerns over immunogenicity. Despite the many advantages of orally administering protein therapeutics, few successes have been realized due to the destabilizing environment of the GI tract. Of the major GI proteases, pepsin is considered the primary cause of antibody degradation and hence a major obstacle facing orally-delivered antibody therapeutics. The introduction of an additional disulfide bond in the hydrophobic core of the anti-TcdA $V_HHs$ not only increased thermal stability at neutral pH, but also represents a generic strategy to increase antibody stability at low pH and impart pepsin resistance which is desirable for protein-based oral therapeutics.

Additional aspects and advantages of the present invention will be apparent in view of the following description. The detailed description and examples, while indicating preferred embodiments of the invention, are given by way of illustration only, as various changes and modifications within the scope of the invention will become apparent to those skilled in the art in light of the teachings of this invention.

BRIEF DESCRIPTION OF THE DRAWINGS

These and other features of the invention will now be described by way of example, with reference to the appended drawings, wherein:

FIG. 1A is a schematic representation of native TcdA/B and recombinant fragments of the cell receptor-binding domain (TcdA-RBD-f1 and TcdB-RBD-f1) used for llama immunization and library panning. Numbers represent the amino acid residues of each toxin, labelled from the N-termini (1) to C-termini (2710/2366 for TcdA and TcdB, respectively). Drawings are not to scale. GT=glucosyltransferase domain; CP=cysteine protease domain; HR=hydrophobic membrane insertion domain; RBD=cell-receptor binding domain. FIG. 1B is an SDS-PAGE profile of the purified *C. difficile* toxins (3 μg per lane; from *C. difficile* strain 10463) used herein. The upper arrow shows full-length TcdA (308 kDa) and TcdB (269 kDa). FIG. 1C shows ELISA results demonstrating a total llama serum response for the recombinant RBD fragments. Serum was prepared from llama blood drawn 57 days after the initial immunization. Immune (A): immune serum against TcdA-RBD-f1; Immune (B): immune serum against TcdB-RBD-f1; Pre-Immune: pre-immune serum against TcdA-RBD-f1. FIG. 1D shows ELISA results demonstrating the llama heavy-chain IgG (HCAb) GI fraction response was specific for the recombinant RBD fragments. Serum was fractionated from llama blood drawn 84 days after the initial immunization and the GI fraction shown did not recognize PEB3 or CPS, two unrelated antigens. FIG. 1E shows the SDS-PAGE profile of purified $V_HHs$ (2 μg per lane) isolated from the hyperimmunized llama phage display library. Molecular weight markers (M) are given in kDa. NR: non-reducing.

FIG. 2 is an amino acid sequence alignment of the anti-TcdA/B $V_HHs$ isolated. Framework regions, FRs, and complementarity-determining regions, CDRs (shaded in grey), are grouped according to the IMGT numbering system (http://imgt.cines.fr/). Hallmark positions, 42, 49, 50 and 52, where $V_HHs$ can be distinguished from $V_H$ based on amino acid identity are illustrated with asterisks. $V_Hs$ generally have V, G, L and W at positions 42, 49, 50 and 52, respectively; in many $V_HHs$, the aforementioned residues are replaced with F/Y, E/Q/R, R and F/L, as shown.

FIG. 3 describes the construction, expression and functional characterization of pentameric versions of monomeric anti-TcdA $V_HHs$. FIG. 3A is a schematic diagram of a $V_HH$ pentamer. $V_HH$ monomers expressed as fusions to the verotoxin B (VTB) subunit self-assembly into pentameric structures in *E. coli*. FIG. 3B shows an SDS-PAGE gel containing eluted IMAC fractions of purified $V_HH$ pentamers A5.1p and A20.1p. Molecular weight markers (M) are given in kDa. NR: non-reducing. Arrows indicate the location of purified VTB-$V_HH$ monomers. FIG. 3C shows ELISA results comparing the functional activity of $V_HH$ monomers (A5.1 and A20.1) and $V_HH$ pentamers (A5.1p and A20.1p) to wells coated with TcdA. Equimolar concentrations of monomer/pentamer were used in the assay relative to the $V_HH$ monomer. Monomer/pentamer binding was detected with rabbit anti-His$_6$ IgG-HRP and absorbances were read at 450 nm.

FIG. 4 depicts the toxin binding characteristics of $V_HHs$. ELISA demonstrating the anti-TcdA $V_HHs$ (FIG. 4A) and anti-TcdB V$_H$Hs (FIG. 4B) recognize native toxins and recombinant RBD fragments. Wells were coated with molar equivalent concentrations. FIG. 4C and FIG. 4D shows binding of various concentrations of V$_H$Hs to immobilized TcdA or TcdB, respectively.

FIGS. 8C-E show neutralization of TcdA-induced cell rounding with V$_H$Hs at 24 h post addition of 100 ng/ml TcdA. The final concentration of V$_H$Hs in each assay well were 1000 nM (FIG. 8C), 10 nM (FIG. 8D) and 0.1 nM (FIG. 8E) and V$_H$Hs were added as singles, pairs, or triplet combinations. White bars represent single V$_H$Hs or PBS control, grey bars represent paired combinations and black bars represent triplet combinations. Combinations of V$_H$Hs (i.e., pairs and triples) increased toxin neutralizing efficacy. FIG. 8F shows representative photographs of TcdA neutralization with 1000 nM V$_H$H were taken 24 h post toxin addition. The black bar represents 100 µm.

FIG. 9A shows ELISA results on TcdA treated with various temperatures for 30 min before probing with V$_H$Hs. At treatment temperatures above the TcdA midpoint unfolding temperature (T$_m$), binding of 4 out of 5 TcdA-specific V$_H$Hs was abolished. The dotted line represents the TcdA T$_m$ of ~55° C. FIG. 9B shows Western blots (reducing/denaturing) probed with His-tagged anti-TcdA V$_H$Hs or control mouse anti-TcdA IgG (PCG-4). Binding was detected with nickel-AP or goat anti-mouse IgG-AP, respectively. Of the V$_H$Hs tested, only A19.2 recognized denatured TcdA and the secondary conjugates did not bind denatured TcdA. FIG. 9C shows Western blots (native-PAGE) probed with anti-TcdA V$_H$Hs or control PCG4. V$_H$Hs and PCG4 bound TcdA. The goat anti-mouse IgG-AP conjugates strongly cross-reacted with TcdA in the absence of PCG4.

FIG. 12A shows the responses of A26.8 binding TcdA, CD-grease binding TcdA and co-injection of A26.8 and CD-grease. FIG. 12B shows the responses of A26.8 binding TcdA, Le$^X$-AmHex binding TcdA and co-injection of A26.8 and Le$^X$-AmHex. FIGS. 12C and 12D show subtraction of the response generated from either trisaccharide binding to TcdA from co-injection experiments reveals a near identical response to that of A26.8 alone, an indication that V$_H$H binding to TcdA is not inhibited by the trisaccharides. In all experiments, V$_H$Hs were used at their K$_D$ concentrations and trisaccharides at their apparent K$_D$ (2 mM).

FIG. 13A shows the injection of A20.1 (A, grey and dashed lines), followed by injection of A20.1 (B, dashed line) or A20.1+CD-grease (B, grey line), and finally injection of Biacore buffer (C, grey and dashed lines). FIG. 13B shows the injection of A26.8 (A, grey and dashed lines), followed by injection of A26.8 (B, dashed line) or co-injection of A26.8+CD-grease (B, grey line), and finally injection of Biacore buffer (C, grey and dashed lines). These results suggest V$_H$H binding is not at or in the carbohydrate binding site on TcdA-RBD.

FIG. 14 shows the alignment and comparison of wild-type and mutant V$_H$H amino acid sequences. Wild-type V$_H$H sequences are shown with a single disulfide bond between Cys$^{23}$ and Cys$^{104}$. A second disulfide bond was introduced through mutation of Ala$^{54}$/Gly$^{54}$ and Ile$^{78}$ to Cys$^{54}$ and Cys⁷⁸ in framework region (FR) 2 and FR3, respectively. Disulfide bonds are shown as black lines. Bolded residues illustrate the disulfide bond-linked peptides identified by nanoRPLC-ESI-MS analysis on CNBr and trypsin digested mutant $V_HH$s. Amino acid numbering and CDR designation is based on the IMGT system.

FIG. 16 confirms the disulfide bond formation between residues Cys⁵⁴ and Cys⁷⁸ by MS².

FIG. 17 shows the characterization of mutant anti-TcdA $V_HH$s which possessed a second disulfide bond in the hydrophobic core that were introduced by mutation of two amino acids to cysteine. FIG. 17A shows a comparison of the Size exclusion chromatography (SEC) analysis of wild-type (WT) anti-TcdA $V_HH$s (top) and mutant anti-TcdA $V_HH$s (bottom) obtained from a Superdex™ 75 column. Similar size exclusion profiles were obtained for mutant and wild-type, indicating the second disulfide bond does not promote the formation of interdomain disulfide-bonds or multimeric mutant $V_HH$s. The elution volumes ($V_e$s) of SEC molecular weight standards are shown with arrows and are aligned relative to the A4.2 and A4.2m chromatograms. a: ovalbumin (MW=43.0 kDa, $V_e$=8.90 ml); b: carbonic anhydrase (MW=30.0 kDa, $V_e$=9.71 ml); c: typsin inhibitor (MW=20.1 kDa, $V_e$=11.06 ml); d: α-lactalbumin (MW=14.4 kDa, $V_e$=11.97 ml); e: vitamin B (MW=1.3 kDa, $V_e$=18.7 ml). The equation of the line of a standard curve generated from these standards was $LOG_{10}MW=-0.1539V_e+2.9949$ ($r^2$=0.9995). From this equation the $V_HH$ apparent MWs ranged from 9.8-13.6 kDa, indicating monomeric $V_HH$s. FIG. 17B shows surface plasmon resonance (SPR) sensorgrapms for four mutant $V_HH$s binding to immobilized TcdA. Grey lines represent raw data measurements and black lines represent fitted curves. Kinetic and affinity constants are given in Table 4. Binding of A19.2m and A24.1m to TcdA was non-specific, and the kinetic and affinity constants could not be determined. The binding shows mutant $V_HH$s with a second disulfide bond retain high-affinity binding to TcdA.

FIG. 20A shows CD spectra collected on equilibrated $V_HH$s (50 µg/ml) at 25° C. before heat treatment (scan 1, solid lines), after exposure to 96° C. for 20 min (scan 2, dotted lines), and after cooling to 25° C. for 3 h (scan 3, dashed lines). Scans are an average of 4 data accumulations. FIG. 20B shows a summary of thermal refolding efficiencies at pH 7.3 and pH 2.0, calculated using Equation 2 and following the changes in ellipticity at 215 nm. Dots represent the mean thermal refolding efficiency (TRE) of individual $V_HH$s from two independent experiments with 4 data accumulations in each experiment. Bars represent the mean TRE of each group of $V_HH$s.

FIGS. 21B and 21C show a summary of the $V_HH$ $T_m$s and $T_{onset}$s, respectively. Each dot represents individual $V_HH$ and the bar represents the mean $T_n$, or $T_{onset}$ value in each group. P-values were determined using the unpaired two-tailed t-test The $T_m$ values are summarized in Table 6.

FIG. 22A is a representative SDS-PAGE gel comparing the profiles of WT and mutant A5.1 $V_HH$ after no treatment or digestion with various ratios of pepsin for 1 h at 37° C. $V_HH$ epitope tags ("tag"), consisting of c-Myc and His₆, were preferentially cleaved by all proteases (confirmed by mass spectrometry analysis—data not shown). Densitometric analysis of SDS-PAGE gels allowed for the determination of a percent of retained $V_HH$ structure, which was denoted percent resistance. FIG. 22B-D summarizes the percent resistance of WT and mutant $V_HH$s to pepsin, trypsin, and chymotrypsin after digestion for 1 h at 37° C. using a protease concentration of 100 µg/ml (1:2.4 ratio of protease:$V_HH$). Error bars represent the SEM obtained from 3 independent digestions for each $V_HH$. FIG. 22E shows a summary of the $V_HH$ resistance to each protease. Dots represent the mean (n=3) protease resistance profile of each $V_HH$ relative to undigested controls and the black bars represent the median resistance of each group. P-values were determined using the unpaired two-tailed Mann-Whitney U test. WT: wild-type $V_HH$; Mut: mutant $V_HH$; Chymo: chymotrypsin. The percent $V_HH$ resistance to each protease is given in Table 8. In A, 1:240 and 1:24 ratios correspond to pepsin concentrations of 1 µg/ml and 10 µg/ml, respectively, in reaction mixtures.

FIG. 23A is a graph showing linear regression between $V_HH$ pepsin resistance and $V_HH$ $T_m$ at pH 2.0. Boxes show the wild-type (WT) and mutant (Mut) $V_HH$s, respectively. Linear regression analysis gave a correlation coefficient of $r^2$=0.735 and a significantly non-zero slope of the line (p=0.0004). FIG. 23B is a graph showing linear regression between wild-type $V_HH$ pepsin resistance and wild-type $V_HH$ $T_{onset}$ at pH 2.0. The $T_{onset}$ is defined as the temperature at which 5% of the $V_HH$ is unfolded. Linear regression analysis gave a correlation coefficient of $r^2$=0.975 and a significantly non-zero slope of the line (p=0.0002). FIG. 23C shows SPR analysis (bottom) on mutant $V_H$Hs digested with pepsin (100 μg/ml, 1 h, 37° C.). The pepsin-treated $V_H$Hs retained their ability to bind surface-immobilized TcdA. SDS-PAGE gel (top) shows untreated (lanes 1, 3, 5, 7) and pepsin-digested (lanes 2, 4, 6, 8) $V_H$Hs used for SPR. The contents of lanes 1 thru 8 are listed in the box. Normalized $k_{off}$s for pepsin treated $V_H$Hs were similar to the $k_{off}$ of untreated controls (box and Table 2). M: molecular weight markers in kDa; WT: wild-type $V_H$H; Mut: mutant $V_H$H; P: pepsin; R: reducing SDS-PAGE conditions.

DETAILED DESCRIPTION OF THE INVENTION

Figure 1:
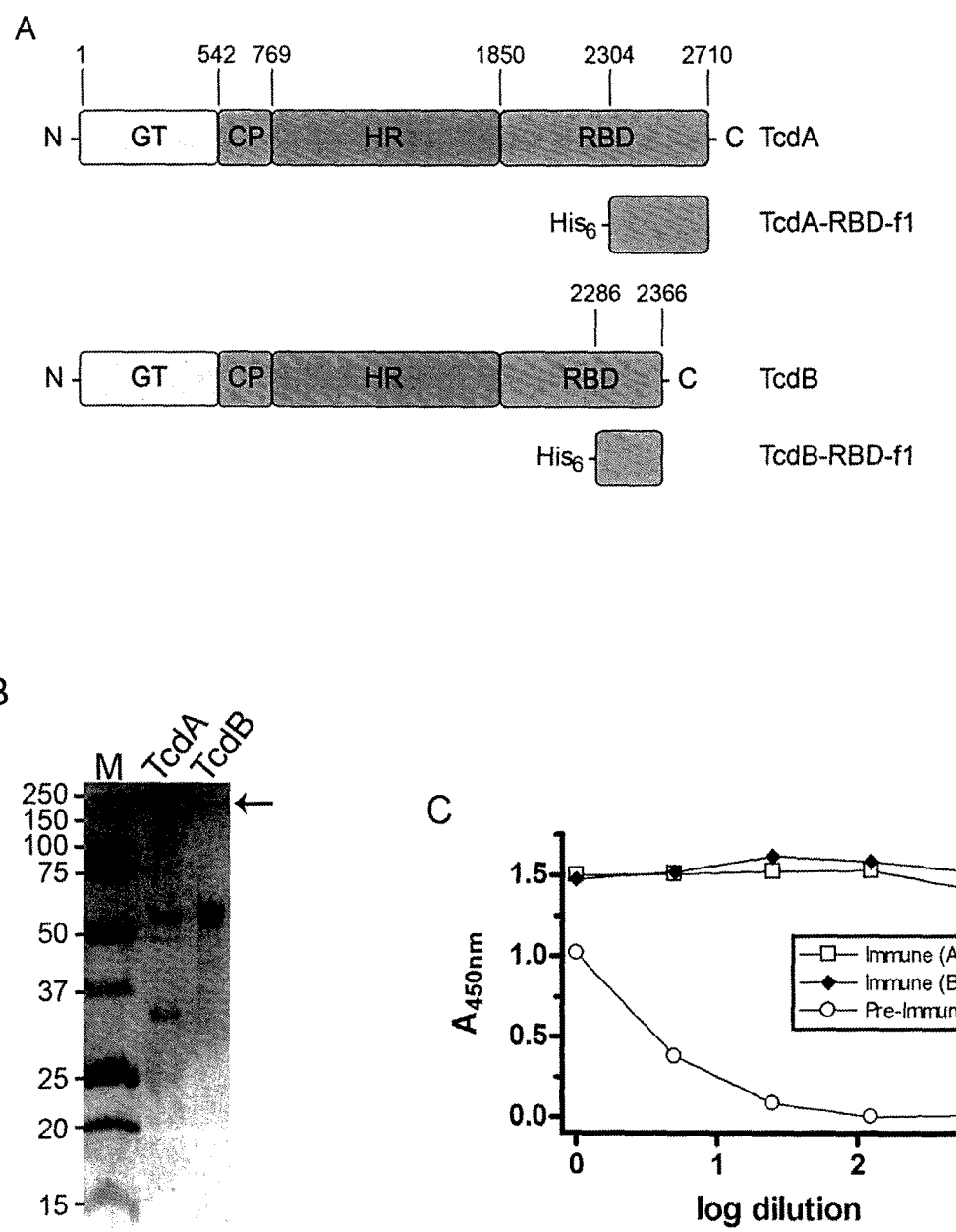
FIG. 1 relates to the isolation of anti-TcdA/B $V_HHs$.

The present invention relates to *Clostridium difficile*-specific antibodies and uses thereof. More specifically, the present invention relates to *Clostridium difficile* toxin-specific antibodies and uses thereof.

The present invention provides isolated llama single-domain antibodies ($V_H$Hs) capable of binding and neutralizing *C. difficile* TcdA and TcdB. Without wishing to be bound by theory, $V_H$Hs targeting the toxin's receptor binding domain (RBD) may block the toxin-receptor interaction, thereby preventing toxin entry into the host cell; this represents a critical initial step in the TcdA/B mechanism of action (Jank and Aktories, 2008).

Thus, the present invention provides an isolated or purified antibody or fragment thereof, comprising
 a sequence of complementarity determining region (CDR) 1 selected from GRTFNTLS (SEQ ID NO:1); GRTFSMYR (SEQ ID NO:2); GRTLSSYI (SEQ ID NO:3); GRTFSMDP (SEQ ID NO:4); IRSFSNRN (SEQ ID NO:5); and ERTFSRYP (SEQ ID NO:6);
 a sequence of CDR2 selected from VSRSGGST (SEQ ID NO:7); ITRNGSST (SEQ ID NO:8); ISRRGGNS (SEQ ID NO:9); GSSTGRTT (SEQ ID NO:10); ISWGGGST (SEQ ID NO:11); and ISSTGTST (SEQ ID NO:12); and
 a sequence of CDR3 selected from AAAATKSNTTAYRLSFDY (SEQ ID NO:13); AATSGSSYLDAAHVYDY (SEQ ID NO:14); AADGSVAGWGRRSVSVSSYDY (SEQ ID NO:15); AAAPYGANWYRDEYAY (SEQ ID NO:16); AAEFGHNIATSSDEYDY (SEQ ID NO:17); and AVNSQRTRLQDPNEYDY (SEQ ID NO:18),
wherein the antibody or fragment thereof is specific for TcdA. The isolated or purified antibody or fragment thereof as just described may comprise
 a sequence of CDR 1 of GRTFNTLS (SEQ ID NO:1); CDR2 of VSRSGGST (SEQ ID NO:7); and CDR3 of AAAATKSNTTAYRLSFDY (SEQ ID NO:13);
 a sequence of CDR 1 of GRTFSMYR (SEQ ID NO:2); CDR2 of ITRNGSST (SEQ ID NO:8); and CDR3 of AATSGSSYLDAAHVYDY (SEQ ID NO:14);
 a sequence of CDR 1 of GRTLSSYI (SEQ ID NO:3); CDR2 of ISRRGGNS (SEQ ID NO:9); and CDR3 of AADGSVAGWGRRSVSVSSYDY (SEQ ID NO:15);
 a sequence of CDR 1 of GRTFSMDP (SEQ ID NO:4); CDR2 of GSSTGRTT (SEQ ID NO:10); and CDR3 of AAAPYGANWYRDEYAY (SEQ ID NO:16);
 a sequence of CDR 1 of IRSFSNRN (SEQ ID NO:5); CDR2 of ISWGGGST (SEQ ID NO:11); and CDR3 of AAEFGHNIATSSDEYDY (SEQ ID NO:17); or
 a sequence of CDR 1 of ERTFSRYP (SEQ ID NO:6); CDR2 of ISSTGTST (SEQ ID NO:12); and CDR3 of AVNSQRTRLQDPNEYDY (SEQ ID NO:18).

The present invention also provides an isolated or purified antibody or fragment thereof, comprising
 a sequence of complementarity determining region (CDR) 1 selected from GNIFSINT (SEQ ID NO:19); GRTASGYG (SEQ ID NO:20); GRTFSSGV (SEQ ID NO:21); GLSRYA (SEQ ID NO:22); and GSISRIST (SEQ ID NO:23);
 a sequence of CDR2 selected from ITSGGTT (SEQ ID NO:24); ISRSGAGT (SEQ ID NO:25); ITTGGST (SEQ ID NO:26); TNWSSGNT (SEQ ID NO:27); and ISTGGTT (SEQ ID NO:28); and
 a sequence of CDR3 selected from NTVKVVGGRLDNPDY (SEQ ID NO:29); VARPTKVDRDYATRREMYNY (SEQ ID NO:30); NSVAVVGGVIKSPDY (SEQ ID NO:31); AARKLDVPSRYSQHYDY (SEQ ID NO:32); and AAGWKVVRGSLEYEY (SEQ ID NO:33),
wherein the antibody or fragment thereof is specific for TcdB. The isolated or purified antibody or fragment thereof as just described may comprise
 a sequence of CDR 1 of GNIFSINT (SEQ ID NO:19); CDR2 of ITSGGTT (SEQ ID NO:24); and CDR3 of NTVKVVGGRLDNPDY (SEQ ID NO:29);
 a sequence of CDR 1 of GRTASGYG (SEQ ID NO:20); CDR2 of ISRSGAGT (SEQ ID NO:25); and CDR3 of VARPTKVDRDYATRREMYNY (SEQ ID NO:30);
 a sequence of CDR 1 of GRTFSSGV (SEQ ID NO:21); CDR2 of ITTGGST (SEQ ID NO:26); and CDR3 of NSVAVVGGVIKSPDY (SEQ ID NO:31);
 a sequence of CDR 1 of GLSRYA (SEQ ID NO:22); CDR2 of TNWSSGNT (SEQ ID NO:27); and CDR3 of AARKLDVPSRYSQHYDY (SEQ ID NO:32); or
 a sequence of CDR 1 of GSISRIST (SEQ ID NO:23); CDR2 of ISTGGTT (SEQ ID NO:28); and CDR3 of AAGWKVVRGSLEYEY (SEQ ID NO:33).

The term "antibody", also referred to in the art as "immunoglobulin" (Ig), used herein refers to a protein constructed from paired heavy and light polypeptide chains; various Ig isotypes exist, including IgA, IgD, IgE, IgG, and IgM. When an antibody is correctly folded, each chain folds into a number of distinct globular domains joined by more linear polypeptide sequences. For example, the immunoglobulin light chain folds into a variable ($V_L$) and a constant ($C_L$) domain, while the heavy chain folds into a variable ($V_H$) and three constant ($C_H$, $C_{H2}$, $C_{H3}$) domains. Interaction of the heavy and light chain variable domains ($V_H$ and $V_L$) results in the formation of an antigen binding region (Fv). Each domain has a well-established structure familiar to those of skill in the art.

The light and heavy chain variable regions are responsible for binding the target antigen and can therefore show significant sequence diversity between antibodies. The constant regions show less sequence diversity, and are responsible for binding a number of natural proteins to elicit important biochemical events. The variable region of an antibody contains the antigen binding determinants of the molecule, and thus determines the specificity of an antibody for its target antigen. The majority of sequence variability occurs in six hypervariable regions, three each per variable heavy ($V_H$) and light ($V_L$) chain; the hypervariable regions combine to form the antigen-binding site, and contribute to binding and recognition of an antigenic determinant. The specificity and affinity of an antibody for its antigen is determined by the structure of the hypervariable regions, as well as their size, shape and chemistry of the surface they present to the antigen. Various schemes exist for identification of the regions of hypervariability, the two most common being those of Kabat and of Chothia and Lesk. Kabat et al (1991) define the "complementarity-determining regions" (CDR) based on sequence variability at the antigen-binding regions of the $V_H$ and $V_L$ domains. Chothia and Lesk (1987) define the "hypervariable loops" (H or L) based on the location of the structural loop regions in the $V_H$ and $V_L$ domains. As these individual schemes define CDR and hypervariable loop regions that are adjacent or overlapping, those of skill in the antibody art often utilize the terms "CDR" and "hypervariable loop" interchangeably, and they may be so used herein. For this reason, the regions forming the antigen-binding site are presently referred to herein as CDR L1, CDR L2, CDR L3, CDR H1, CDR H2, CDR H3 in the case of antibodies comprising a $V_H$ and a $V_L$ domain; or as CDR1, CDR2, CDR3 in the case of the antigen-binding regions of either a heavy chain or a light chain. The CDR/loops are referred to herein according to the IMGT numbering system (Lefranc, M.-P. et al., 2003), which was developed to facilitate comparison of variable domains. In this system, conserved amino acids (such as Cys23, Trp41, Cys104, Phe/Trp118, and a hydrophobic residue at position 89) always have the same position. Additionally, a standardized delimitation of the framework regions (FR1: positions 1 to 26; FR2: 39 to 55; FR3: 66 to 104; and FR4: 118 to 128) and of the CDR (CDR1: 27 to 38, CDR2: 56 to 65; and CDR3: 105 to 117) is provided.

An "antibody fragment" as referred to herein may include any suitable antigen-binding antibody fragment known in the art. The antibody fragment may be a naturally-occurring antibody fragment, or may be obtained by manipulation of a naturally-occurring antibody or by using recombinant methods. For example, an antibody fragment may include, but is not limited to a Fv, single-chain Fv (scFv; a molecule consisting of $V_L$ and $V_H$ connected with a peptide linker), Fab, F(ab')$_2$, single domain antibody (sdAb; a fragment composed of a single $V_L$ or $V_H$), and multivalent presentations of any of these.

In a non-limiting example, the antibody fragment may be an sdAb derived from naturally-occurring sources. Heavy chain antibodies of camelid origin (Hamers-Casterman et al, 1993) lack light chains and thus their antigen binding sites consist of one domain, termed $V_HH$. sdAb have also been observed in shark and are termed $V_{NAR}$ (Nuttall et al, 2003). Other sdAb may be engineered based on human Ig heavy and light chain sequences (Jespers et al, 2004; To et al, 2005). As used herein, the term "sdAb" includes those sdAb directly isolated from $V_H$, $V_HH$, $V_L$, or $V_{NAR}$ reservoir of any origin through phage display or other technologies, sdAb derived from the aforementioned sdAb, recombinantly produced sdAb, as well as those sdAb generated through further modification of such sdAb by humanization, affinity maturation, stabilization, solubilization, e.g., camelization, or other methods of antibody engineering. Also encompassed by the present invention are homologues, derivatives, or fragments that retain the antigen-binding function and specificity of the sdAb.

A person of skill in the art would be well-acquainted with the structure of a single-domain antibody (see, for example, 3DWT, 2P42 in Protein Data Bank). An sdAb comprises a single immunoglobulin domain that retains the immunoglobulin fold; most notably, only three CDR/hypervariable loops form the antigen-binding site. However, and as would be understood by those of skill in the art, not all CDR may be required for binding the antigen. For example, and without wishing to be limiting, one, two, or three of the CDR may contribute to binding and recognition of the antigen by the sdAb of the present invention. The CDR of the sdAb or variable domain are referred to herein as CDR1, CDR2, and CDR3, and numbered as defined by Lefranc, M.-P. et al. (2003).

As previously stated, the antibody or fragment thereof may be an sdAb. The sdAb may be of camelid origin or derived from a camelid $V_HH$, and thus may be based on camelid framework regions; alternatively, the CDR described above may be grafted onto $V_{NAR}$, $V_HH$, $V_H$ or $V_L$ framework regions. In yet another alternative, the hypervariable loops described above may be grafted onto the framework regions of other types of antibody fragments (Fv, scFv, Fab). The present embodiment further encompasses an antibody fragment that is "humanized" using any suitable method know in the art, for example, but not limited to CDR grafting and veneering. Humanization of an antibody or antibody fragment comprises replacing an amino acid in the sequence with its human counterpart, as found in the human consensus sequence, without loss of antigen-binding ability or specificity; this approach reduces immunogenicity of the antibody or fragment thereof when introduced into human subjects. In the process of CDR grafting, one or more than one of the heavy chain CDR defined herein may be fused or grafted to a human variable region ($V_H$, or $V_L$), or to other human antibody fragment framework regions (Fv, scFv, Fab). In such a case, the conformation of said one or more than one hypervariable loop is preserved, and the affinity and specificity of the sdAb for its target (i.e., toxins A and B) is also preserved. CDR grafting is known in the art and is described in at least the following: U.S. Pat. Nos. 6,180,370, 5,693,761, 6,054,297, 5,859,205, and European Patent No. 626390. Veneering, also referred to in the art as "variable region resurfacing", involves humanizing solvent-exposed positions of the antibody or fragment; thus, buried non-humanized residues, which may be important for CDR conformation, are preserved while the potential for immunological reaction against solvent-exposed regions is minimized. Veneering is known in the art and is described in at least the following: U.S. Pat. Nos. 5,869,619, 5,766,886, 5,821,123, and European Patent No. 519596. Persons of skill in the art would also be amply familiar with methods of preparing such humanized antibody fragments and humanizing amino acid positions.

In a specific, non-limiting example, the antibody or fragment thereof that is specific for TcdA may comprise a sequence selected from the group consisting of:

(SEQ ID NO: 34)
QVKLEESGGGLVQAGGSLRLSCAASGRTFNTLSMGWFRQAPGKEREFVAAVSRSGGSTYY

ADSVKGRFTISRDNAKNTVYLQMNSLKPEDTAVYYCAAAATKSNTTAYRLSFDYWGQGTQVT

VSS,
referred to herein as A4.2;

(SEQ ID NO: 35)
QVKLEESGGGLVQAGGSLRLSCAASGRTFSMYRMGWFRQAPGKEREFVGVITRNGSSTYYA

DSVKGRFTISRDNAKNTVYLQMNSLKPEDTALYYCAATSGSSYLDAAHVYDYWGQGTQVTVS

S,
referred to herein as A5.1;

(SEQ ID NO: 36)
QVKLEESGGGLVQPGGSLRLSCAASGRTLSSYIVAWFRQAPGKEREFVAGISRRGGNSAYV

ESVKGRFTISRDNAKNTVYLQMNSLKPEDTAVYYCAADGSVAGWGRRSVSVSSYDYWGQG

TQVTVSS,
referred to herein as A19.2;

(SEQ ID NO: 37)
QVQLVESGGGLAQAGGSLRLSCAASGRTFSMDPMAWFRQPPGKEREFVAAGSSTGRTTYY

ADSVKGRFTISRDNAKNTVYLQMNSLKPEDTAVYYCAAAPYGANWYRDEYAYWGQGTQVTV

SS,
referred to herein as A20.1;

(SEQ ID NO: 38)
QVQLVESGGGLVQAGGSLRLSCAASIRSFSNRNMGWFRQPPGKEREFVAGISWGGGSTRY

ADSVKGRFTISRDNAKKTVYLQMNSLKPEDTAVYYCAAEFGHNIATSSDEYDYWGQGTQVTV

SS,
referred to herein as A24.1;
and (SEQ ID NO: 39)
QVKLEESGGGLVQAGGSLRLSCAASERTFSRYPVAWFRQAPGAEREFVAVISSTGTSTYYAD

SVKGRFTISRDNAKVTVYLQMNNLKREDTAVYFCAVNSORTRLQDPNEYDYWGQGTQVTVS

S,
referred to herein as A 26.8,

40 or a sequence substantially identical thereto.

In a specific, non-limiting example, the antibody or fragment thereof that is specific for TcdB may comprise a sequence selected from the group consisting of:

(SEQ ID NO: 40)
QVQLVESGGGLVQPGGSLRLSCAASGNIFSINTMGWYRQAPGKQLELVAAITSGGTTSYTDS

VEGRFTISRDNAKNAVYLQMNSLKAEDTAVYYCNTVKVVGGRLDNPDYWGQGTQVTVSS,
referred to herein as B5.2;

(SEQ ID NO: 41)
QVKLEESGGGLVQPGGSLRLSCAASGRTASGYGMGWFRQAPGKEREFVAAISRSGAGTLN

ADFVKGRFTISRDNAKNTVYLQMNSLKPEDTAVYYCVARPTKVDRDYATRREMYNYWGQGT

QVTVSS,
referred to herein as B7.3;

(SEQ ID NO: 42)
QVKLEESGGGLVQAGGSLRLSCSASGRTFSSGVMGWFRQAPGKQRELVAAITTGGSTSYTD

SVKGRFTISRDNAKNIVYLQMNSLKPEDTAVYYCNSVAVVGGVIKSPDYWGQGTQVTVSS,
referred to herein as B13.6;

(SEQ ID NO: 43)
QVQLVESGGGSVQAGGSLRLSCAASGLSRYAMAWFRQGTGKEREFVASTNWSSGNTPYAD

```
SVKGRFIISRDNAKNTVYLQMNSLKPGDTAIYYCAARKLDVPSRYSQHYDYWGQGTQVTVSS,
referred to herein as B15.3;
and
```

(SEQ ID NO: 44)
```
QVQLVESGGDLVQAGGSLRLSCAASGSISRISTMGWYRQAPGKQRELVATISTGGTTNYAES

VKGRFTVSRDNAKNTMYLQMNSLKPEDTAVYYCAAGWKVVRGSLEYEYSGQGTQVTVSS,
referred to herein as B15.5,
``` or a sequence substantially identical thereto

A substantially identical sequence may comprise one or more conservative amino acid mutations. It is known in the art that one or more conservative amino acid mutations to a reference sequence may yield a mutant peptide with no substantial change in physiological, chemical, physicochemical or functional properties compared to the reference sequence; in such a case, the reference and mutant sequences would be considered "substantially identical" polypeptides. Conservative amino acid mutation may include addition, deletion, or substitution of an amino acid; a conservative amino acid substitution is defined herein as the substitution of an amino acid residue for another amino acid residue with similar chemical properties (e.g. size, charge, or polarity).

In a non-limiting example, a conservative mutation may be an amino acid substitution. Such a conservative amino acid substitution may substitute a basic, neutral, hydrophobic, or acidic amino acid for another of the same group. By the term "basic amino acid" it is meant hydrophilic amino acids having a side chain pK value of greater than 7, which are typically positively charged at physiological pH. Basic amino acids include histidine (His or H), arginine (Arg or R), and lysine (Lys or K). By the term "neutral amino acid" (also "polar amino acid"), it is meant hydrophilic amino acids having a side chain that is uncharged at physiological pH, but which has at least one bond in which the pair of electrons shared in common by two atoms is held more closely by one of the atoms. Polar amino acids include serine (Ser or S), threonine (Thr or T), cysteine (Cys or C), tyrosine (Tyr or Y), asparagine (Asn or N), and glutamine (Gln or Q). The term "hydrophobic amino acid" (also "non-polar amino acid") is meant to include amino acids exhibiting a hydrophobicity of greater than zero according to the normalized consensus hydrophobicity scale of Eisenberg (1984). Hydrophobic amino acids include proline (Pro or P), isoleucine (Ile or I), phenylalanine (Phe or F), valine (Val or V), leucine (Leu or L), tryptophan (Trp or W), methionine (Met or M), alanine (Ala or A), and glycine (Gly or G). "Acidic amino acid" refers to hydrophilic amino acids having a side chain pK value of less than 7, which are typically negatively charged at physiological pH. Acidic amino acids include glutamate (Glu or E), and aspartate (Asp or D).

Sequence identity is used to evaluate the similarity of two sequences; it is determined by calculating the percent of residues that are the same when the two sequences are aligned for maximum correspondence between residue positions. Any known method may be used to calculate sequence identity; for example, computer software is available to calculate sequence identity. Without wishing to be limiting, sequence identity can be calculated by software such as NCBI BLAST2 service maintained by the Swiss Institute of Bioinformatics (and as found at http://ca.expasy.org/tools/blast/), BLAST-P, Blast-N, or FASTA-N, or any other appropriate software that is known in the art.

The substantially identical sequences of the present invention may be at least 65% identical; in another example, the substantially identical sequences may be at least 65, 70, 85, 90, 95, 96, 97, 98, 99, or 100% identical, or any percentage therebetween, at the amino acid level to sequences described herein. Importantly, the substantially identical sequences retain the activity and specificity of the reference sequence. In a non-limiting embodiment, the difference in sequence identity may be due to conservative amino acid mutation(s). By way of example only, and without wishing to be limiting in any manner, the $V_H$Hs of the present invention have between about 66% and 82% sequence identity (see Tables 5 and 6). In another non-limiting example, the present invention may be directed to an antibody or fragment thereof comprising a sequence at least 98% identical to that of the $V_H$Hs described herein.

A substantially identical sequence as defined by the present invention also includes a mutation to introduce an additional non-canonical disulfide bond. For example, and without wishing to be limiting, the non-canonical disulfide bond may be introduced between framework region (FR) 2 and FR3. In a specific, non-limiting example, the mutation may be Ala/Gly$^{54}$→Cys$^{54}$ and/or Val/Ile$^{78}$→Cys$^{78}$ mutation (based on IMGT numbering). In a further specific example, the antibody or fragment thereof that is specific for TcdA may comprise a sequence selected from the group consisting of:

(SEQ ID NO: 45)
```
QVKLEESGGGLVQAGGSLRLSCAASGRTFNTLSMGWFRQAPGKEREFVΣAVSRSGGSTYY

ADSVKGRFTΣSRDNAKNTVYLQMNSLKPEDTAVYYCAAAATKSNTTAYRLSFDYWGQGTQV

TVSS,
referred to herein as A4.2m;
```

(SEQ ID NO: 46)
```
QVKLEESGGGLVQAGGSLRLSCAASGRTFSMYRMGWFRQAPGKEREFVΣVITRNGSSTYYA

DSVKGRFTΣSRDNAKNTVYLQMNSLKPEDTALYYCAATSGSSYLDAAHVYDYWGQGTQVTV

SS,
referred to herein as A5.1m;
```

-continued (SEQ ID NO: 47)
QVKLEESGGGLVQPGGSLRLSCAASGRTLSSYIVAWFRQAPGKEREFVXGISRRGGNSAYV

ESVKGRFTXSRDNAKNTVYLQMNSLKPEDTAVYYCAADGSVAGWGRRSVSVSSYDYWGQG

TQVTVSS,
referred to herein as A19.2m;

(SEQ ID NO: 48)
QVQLVESGGGLAQAGGSLRLSCAASGRTFSMDPMAWFRQPPGKEREFVXAGSSTGRTTYY

ADSVKGRFTXSRDNAKNTVYLQMNSLKPEDTAVYYCAAAPYGANWYRDEYAYWGQGTQVT

VSS,
referred to herein as A20.1m;

(SEQ ID NO: 49)
QVQLVESGGGLVQAGGSLRLSCAASIRSFSNRNMGWFRQPPGKEREFVXGISWGGGSTRY

ADSVKGRFTXSRDNAKKTVYLQMNSLKPEDTAVYYCAAEFGHNIATSSDEYDYWGQGTQVT

VSS,
referred to herein as A24.1m;

(SEQ ID NO: 50)
QVKLEESGGGLVQAGGSLRLSCAASERTFSRYPVAWFRQAPGAEREFVXVISSTGTSTYYAD

SVKGRFTXSRDNAKVTVYLQMNNLKREDTAVYFCAVNSQRTRLQDPNEYDYWGQGTQVTV

SS,
referred to herein as A26.8m;

(SEQ ID NO: 51)
QVQLVESGGGLVQPGGSLRLSCAASGNIFSINTMGWYRQAPGKQLELVXAITSGGTTSYTDS

VEGRFTXSRDNAKNAVYLQMNSLKAEDTAVYYCNTVKVVGGRLDNPDYWGQGTQVTVSS,
referred to herein as B5.2m;

(SEQ ID NO: 52)
QVKLEESGGGLVQPGGSLRLSCAASGRTASGYGMGWFRQAPGKEREFVXAISRSGAGTLN

ADFVKGRFTXSRDNAKNTVYLQMNSLKPEDTAVYYCVARPTKVDRDYATRREMYNYWGQG

TQVTVSS,
referred to herein as B7.3m;

(SEQ ID NO: 53)
QVKLEESGGGLVQAGGSLRLSCSASGRTFSSGVMGWFRQAPGKQRELVXAITTGGSTSYTD

SVKGRFTXSRDNAKNTVYLQMNSLKPEDTAVYYCNSVAWGGVIKSPDYWGQGTQVTVSS,
referred to herein as B13.6m;

(SEQ ID NO: 54)
QVQLVESGGGSVQAGGSLRLSCAASGLSRYAMAWFRQGTGKEREFVXSTNWSSGNTPYAD

SVKGRFIXSRDNAKNTVYLQMNSLKPGDTAIYYCAARKLDVPSRYSQHYDYWGQGTQVTVS

S,
referred to herein as B15.3m;
and (SEQ ID NO: 55)
QVQLVESGGDLVQAGGSLRLSCAASGSISRISTMGWYRQAPGKQRELXATISTGGTTNYAES VKGRFTXSRDNAKNTMYLQMNSLKPEDTAVYYCAAGWKVVRGSLEYEYSGQGTQVTVS,
referred to herein as B15.5m, or a sequence substantially identical thereto, with the proviso that the substantially identical sequence retains the non-canonical disulfide bond.

The isolated or purified antibody or fragment thereof of the present invention may bind to a conformational or linear epitope. A conformational epitope is formed by amino acid residues that are discontinuous in sequence, but proximal in the three-dimensional structure of the antigen. In contrast, a linear epitope (also referred to in the art as a "sequential epitope") is recognized by its linear amino acid sequence, or primary structure. The conformational and linear epitopes of the antibodies or fragments thereof of the present invention recognize conformational and linear epitopes located in the region of TcdA responsible for cell-receptor binding.

The antibody or fragment thereof of the present invention may also comprise additional sequences to aid in expression, detection or purification of a recombinant antibody or fragment thereof. Any such sequences or tags known to those of skill in the art may be used. For example, and without wishing to be limiting, the antibody or fragment thereof may comprise a targeting or signal sequence (for example, but not limited to ompA), a detection/purification tag (for example, but not limited to c-Myc or a $His_6$ or $His_6$), or a combination thereof. In another example, the additional sequence may be a biotin recognition site such as that described by Cronan et al in WO 95/04069 or Voges et al in WO/2004/076670. As is also known to those of skill in the art, linker sequences may be used in conjunction with the additional sequences or tags, or may serve as a detection/purification tag.

The antibody or fragment thereof of the present invention may also be in a multivalent display format, also referred to herein as multivalent presentation. Multimerization may be achieved by any suitable method of know in the art. For example, and without wishing to be limiting in any manner, multimerization may be achieved using self-assembly molecules as described in Zhang et al (2004a; 2004b) and WO2003/046560. The described method produces pentabodies by expressing a fusion protein comprising the antibody or fragment thereof of the present invention and the pentamerization domain of the B-subunit of an $AB_5$ toxin family (Merritt & Hol, 1995); the pentamerization domain assembles into a pentamer, through which a multivalent display of the antibody or fragment thereof is formed. Each subunit of the pentamer may be the same or different, and may have the same or different specificity. Additionally, the pentamerization domain may be linked to the antibody or antibody fragment using a linker; such a linker should be of sufficient length and appropriate composition to provide flexible attachment of the two molecules, but should not hamper the antigen-binding properties of the antibody.

Other forms of multivalent display are also encompassed by the present invention. For example, and without wishing to be limiting, the antibody or fragment thereof may be presented as a dimer, a trimer, or any other suitable oligomer. This may be achieved by methods known in the art, for example direct linking connection (Nielson et al, 2000), c-jun/Fos interaction (de Kruif & Logtenberg, 1996), "Knob into holes" interaction (Ridgway et al, 1996). Another method known in the art for multimerization is to dimerize the antibody or fragment thereof using an Fc domain, e.g., human Fc domains. The Fc domains may be selected from various classes including, but not limited to, IgG, IgM, or various subclasses including, but not limited to IgG1, IgG2, etc. In this approach, the Fc gene in inserted into a vector along with the sdAb gene to generate a sdAb-Fc fusion protein (Bell et al, 2010; Iqbal et al, 2010); the fusion protein is recombinantly expressed then purified. For example, and without wishing to be limiting in any manner, multivalent display formats may encompass chimeric formats of anti-TcdA $V_H$Hs linked to an Fc domain, or bi- or tri-specific antibody fusions with two or three anti-TcdA $V_H$Hs recognizing unique epitopes. Enhanced toxin neutralizing efficacy may also be obtained using various techniques, including PEGylation, fusion to serum albumin, or fusion to serum albumin-specific antibody fragments; these approaches increase their blood circulation half lives, size and avidity.

The present invention also encompasses nucleic acid sequences encoding the molecules as described herein. The nucleic acid sequence may be codon-optimized for expression in various micro-organisms. The present invention also encompasses vectors comprising the nucleic acids as just described. Furthermore, the invention encompasses cells comprising the nucleic acid and/or vector as described.

The present invention further encompasses the isolated or purified antibody or fragments thereof immobilized onto a surface using various methodologies; for example, and without wishing to be limiting, the antibody or fragment may be linked or coupled to the surface via His-tag coupling, biotin binding, covalent binding, adsorption, and the like. Immobilization of the antibody or fragment thereof of the present invention may be useful in various applications for capturing, purifying or isolating proteins. The solid surface may be any suitable surface, for example, but not limited to the well surface of a microtiter plate, channels of surface plasmon resonance (SPR) sensorchips, membranes, beads (such as magnetic-based or sepharose-based beads or other chromatography resin), glass, plastic, stainless steel, a film, or any other useful surface such as nanoparticles, nanowires and cantilever surfaces.

Thus, the present invention also provides a method of capturing *Clostridium difficile* toxins, comprising contacting a sample (such as, but not limited to *C. difficile* culture supernatant, human/animal intestinal/colonic fluid, or any other suitable sample) with one or more than one isolated or purified antibody or fragment thereof of the present invention. The isolated or purified antibody or fragments thereof may be immobilized onto a surface. The toxin(s) then bind to the isolated or purified antibody or fragment thereof and are thus captured. The toxins may then optionally be identified by mass spectrometric methods and/or released or eluted from their interaction with the antibody or fragment thereof; methods for releasing or eluting bound molecules are well-known to those of skill in the art (for example but not limited to heat elution steps), as are spectrometric methods capable of detecting and identifying the toxin. The isolated or purified antibody or fragment thereof of the present invention provide particularly robust affinity purification reagents due to their resistance to acidic and heat elution steps.

The invention also encompasses the antibody or fragment thereof as described above linked to a cargo molecule. The cargo molecule may be any suitable molecule. For example, and without wishing to be limiting in any manner, the cargo molecule may be a detectable agent, a therapeutic agent, a drug, a peptide, an enzyme, a protease, a carbohydrate moiety, a cytotoxic agent, one or more liposomes loaded with any of the previously recited types of cargo molecules, or one or more nanoparticle, nanowire, nanotube, or quantum dots. For example, and without wishing to be limiting in any manner, the cargo molecule may be a protease that may digest the *C. difficile* toxin; in a further non-limiting example, the protease may be linked to a $V_H$H such as a mutant $V_H$H that is protease resistant. In yet another non-limiting example, the cargo molecule may be a cytotoxic agent that may be antibacterial or toxic towards host cells "infected" with *C. difficile* toxins. In a further non-limiting example, the cargo molecule is a liposome, which makes the construct well-suited as a delivery agent for mucosal vaccines. The cargo molecule may be linked to the antibody or fragment thereof by any suitable method known in the art. For example, and without wishing to be limiting, the cargo molecule may be linked to the peptide by a covalent bond or ionic interaction. The linkage may be achieved through a chemical cross-linking reaction, or through fusion using recombinant DNA methodology combined with any peptide expression system, such as bacteria, yeast or mammalian cell-based systems. Methods for linking an antibody or fragment thereof to a therapeutic agent or detectable agent would be well-known to a person of skill in the art.

The present invention also encompasses an antibody or fragment thereof linked to a detectable agent. For example, the TcdA- or TcdB-specific antibody or fragment thereof may be linked to a radioisotope, a paramagnetic label, a fluorophore, an affinity label (for example biotin, avidin, etc), fused to a detectable protein-based molecule, nucleotide, quantum dot, nanoparticle, nanowire, or nanotube or any other suitable agent that may be detected by imaging methods. In a specific, non-limiting example, the antibody or fragment thereof may be linked to a fluorescent agent such as FITC or may genetically be fused to the Enhanced Green Fluorescent Protein (EGFP). The antibody or fragment thereof may be linked to the detectable agent using any method known in the art (recombinant technology, chemical conjugation, etc.).

Thus, the present invention further provides a method of detecting *Clostridium difficile* toxins, comprising contacting a sample (such as, but not limited to *C. difficile* culture supernatant, human/animal intestinal/colonic fluid, or any other suitable sample) with one or more than one isolated or purified antibody or fragment thereof of the present invention. The isolated or purified antibody or fragments thereof may be linked to a detectable agent. The toxin(s) can then be detected using detection and/or imaging technologies known in the art, such as, but not limited to mass spectrometric or immunoassay methods.

For example, and without wishing to be limiting in any manner, the isolated or purified antibody or fragment thereof linked to a detectable agent may be used in immunoassays (IA) including, but not limited to enzyme IA (EIA), ELISA, "rapid antigen capture", "rapid chromatographic IA", and "rapid EIA". (For example, see Planche et al, 2008; Sloan et al, 2008; Rüssmann et al, 2007; Musher et al, 2007; Turgeon et al, 2003; Fenner et al, 2008)

The present invention also encompasses the isolated or purified antibody or fragment thereof for detection of toxins in neutralized cell toxicity assays; methods for cell toxicity assays, also referred to herein as cytotoxicity assays, are known in the art and include, but are not limited to those described by Planche et al (2008); Musher et al (2007); Turgeon et al (2003); and Fenner et al (2008). Cell cytotoxicity assays involve incubating samples (for example, but not limited to patient stool samples) with cultured cells (for example, but not limited to fibroblasts) alone, or with the addition of a neutralizing agent, in this case, the isolated or purified antibody or fragment thereof as described herein. If the presence of the neutralizing agent reduces or eliminates cell toxicity observed with the cultured cells alone, presence of the toxins in the sample is confirmed. This type of assay is the practical gold standard for CDAD detection in hospital diagnostic laboratories.

The present invention also encompasses a composition comprising one or more than one isolated or purified antibody or fragment thereof as described herein. The composition may comprise a single antibody or fragment as described above, or may be a mixture of antibodies or fragments. Furthermore, in a composition comprising a mixture of antibodies or fragments of the present invention, the antibodies may have the same specificity, or may differ in their specificities; for example, and without wishing to be limiting in any manner, the antibodies or fragments may be specific to TcdA or TcdB, or a portion of the antibodies may be specific to TcdA while the other portion is specific to TcdB.

The composition may also comprise a pharmaceutically acceptable diluent, excipient, or carrier. The diluent, excipient, or carrier may be any suitable diluent, excipient, or carrier known in the art, and must be compatible with other ingredients in the composition, with the method of delivery of the composition, and is not deleterious to the recipient of the composition. The composition may be in any suitable form; for example, the composition may be provided in suspension form, powder form (for example, but limited to lyophilised or encapsulated), capsule or tablet form. For example, and without wishing to be limiting, when the composition is provided in suspension form, the carrier may comprise water, saline, a suitable buffer, or additives to improve solubility and/or stability; reconstitution to produce the suspension is effected in a buffer at a suitable pH to ensure the viability of the antibody or fragment thereof. Dry powders may also include additives to improve stability and/or carriers to increase bulk/volume; for example, and without wishing to be limiting, the dry powder composition may comprise sucrose or trehalose. In a specific, non-limiting example, the composition may be so formulated as to deliver the antibody or fragment thereof to the gastrointestinal tract of the subject. Thus, the composition may comprise encapsulation, time-release, or other suitable technologies for delivery of the antibody or fragment thereof. It would be within the competency of a person of skill in the art to prepare suitable compositions comprising the present compounds.

The present invention also comprises a method of treating a *Clostridium difficile* infection, comprising administering the isolated or purified antibody or fragment thereof of the present invention, or a composition comprising the antibody or fragment thereof, to a subject in need thereof. Any suitable method of delivery may be used. For example, and without wishing to be limiting in any manner, the antibody or fragment thereof, or the composition, may be delivered systemically (orally, nasally, intravenously, etc.) or may be delivered to the gastrointestinal tract. Those of skill in the art would be familiar with such methods of delivery.

The present invention will be further illustrated in the following examples. However, it is to be understood that these examples are for illustrative purposes only and should not be used to limit the scope of the present invention in any manner.

EXAMPLE 1

Purification of Toxins and Recombinant Fragments

*C. difficile*-associated diseases (CDAD) are caused by two high-molecular weight toxins composed of enzymatic, translocation, and cell-receptor binding domains (RBD; FIG. 1A). TcdA and TcdB toxins were purified from natural sources, and recombinant fragments thereof were prepared.

TcdA and TcdB were isolated from *Clostridium difficile* strain 10463 (ATCC, Manassas, Va.) as described previously (Keel and Songer, 2007) and were stored in 50 mM Tris-HCl buffer pH 7.5 at 4° C. The SDS-PAGE profile of the purified *C. difficile* toxins (3 µg per lane; from strain 10463) used is shown in FIG. 1B.

Recombinant fragments of TcdA (amino acid residues 2304-2710) and TcdB (amino acid residues 2286-2366), which are fragments of the RBD, were cloned (as a BamHI-HindIII fragment for tcdA and a BamHI-EcoRI fragment for tcdB) into pTrcHisB (Invitrogen, Carlsbad, Calif.), transforming *E. coli* DH5aMCR. Expression was induced by IPTG, cells harvested and lysed in a French pressure cell, and proteins TcdA-RBD-f1 and TcdB-RBD-f1 purified by immobilized metal-affinity chromatography (IMAC). Recombinant RBD fragments were dialyzed into phosphate-buffered saline (PBS) pH 7.3 and stored at 4° C.

EXAMPLE 2

Llama Immunization and Serum Response

To isolate $V_H$Hs which target the RBD of toxin A (TcdA) and toxin B (TcdB), a llama was immunized with recombinant RBD fragments TcdA-RBD-f1 and TcdB-RBD-f1 (FIG. 1A) obtained in Example 1.

One male llama (*Lama glama*) was immunized by subcutaneous, lower-back injection of TcdA-RBD-f1 and TcdB-RBD-f1 antigens. On Day 1, 200 µg of each antigen diluted in PBS to 1 ml was injected with 1 ml of Freund's Complete Adjuvant (Sigma, St. Louis, Mo.). Three more injections of 100 µg of each antigen+Freund's Incomplete Adjuvant (Sigma) were performed on Days 22, 36, and 50. A final injection of 100 µg of each antigen with no adjuvant was performed on Day 77. Pre-immune blood was drawn before the first injection on Day 1 and served as a negative control. Blood (10-15 ml) was collected on Days 29, 43, 57and 84. Pre-immune and post-immune total serum was analyzed for a specific response to TcdA-RBD-f1 and TcdB-RBD-f1 by ELISA on Day 57 (see below). Llama sera from Day 84 were fractionated as previously described (Doyle et al, 2008). The resulting fractions, A1 (HCAb), A2 (HCAb), G1 (HCAb) and G2 (cIgG) were analyzed for specific binding to TcdA-RBD-f1 and TcdB-RBD-f1 by ELISA. Briefly, 5 µg of TcdA-RBD-f1 or TcdB-RBD-f1 diluted in PBS was coated overnight (100 µl/well, 18 h, 4° C.) in 96 well MAXISORP plates (Nalge Nunc International, Rochester, N.Y.). Plates were blocked with bovine serum albumin (BSA), washed with PBS-T (PBS+0.05% (v/v) Tween-20), and serial dilutions of pre-immune total serum, post-immune total serum (Day 57) and fractionated serum (Day 84) applied. After incubation at room temperature for 1.5 h and washing with PBS-T, goat anti-llama IgG (1:1,000 in PBS) was added for 1 h at 37° C. After washing with PBS-T, pig anti-goat IgG-HRP conjugate (1:3,000 in PBS) was added for 1 h at 37° C. A final PBS-T wash precluded the addition of 100 µl/well TMB substrate (KPL, Gaithersburg, Md.) for 10 min. The reaction was stopped with 100 µl/well 1 M $H_3PO_4$ and read on a BioRad plate reader (Hercules, CA) at 450 nm.

An ELISA conducted on total serum from Day 57 clearly showed a specific immune response for TcdA-RBD-f1 and TcdB-RBD-f1 compared to pre-immune sera collected before immunization on Day 0 (FIG. 1C). A second ELISA performed on fractionated sera from Day 84 indicated the heavy-chain IgG (HCAb) and conventional IgG (cIgG) serum fractions recognized TcdA-RBD-f1 and TcdB-RBD-f1. For example, the G1 HCAb fraction was shown to specifically recognize both recombinant fragments and did not bind to two unrelated proteins PEB3 or CPS (FIG. 1D).

EXAMPLE 3

Library Construction and Selection of Toxin-binding $V_H$Hs

A hyperimmunized llama $V_H$H library was constructed based on RNA isolated from the serum collected in Example 2.

Library construction and panning was performed essentially as previously described (Arbabi-Ghahroudi et al, 2009c, 2009b; Tanha et al, 2003). Total RNA was isolated from approximately 5×10$^6$ lymphocytes collected on day 84 post-immunization using the QIAAMP RNA Blood Mini Kit (QIAGEN, Mississauga, ON, Canada). About 5 µg of total RNA was used as template for first strand cDNA synthesis with oligo dT primers using the First-Strand cDNA Synthesis Kit (GE Healthcare, Baie-d'Urfé, QC, Canada). The cDNA was amplified by an equimolar mix of three variable region-specific sense primers:

MJ1:

(SEQ ID NO: 56)
5'-GCCCAGCCGGCCATGGCCSMKGTGCAGCTGGTGGAKTCTGGGGG
A-3'

MJ2:

(SEQ ID NO: 57)
5'-CAGCCGGCCATGGCCCAGGTAAAGCTGGAGGAGTCTGGGGGA-3'

MJ3:

(SEQ ID NO: 58)
5'-GCCCAGCCGGCCATGGCCCAGGCTCAGGTACAGCTGGTGGAGTC
T-3', and two antisense $CH_2$-specific primers:

$CH_2$:

(SEQ ID NO: 59)
5'-CGCCATCAAGGTACCAGTTGA-3'

$CH_2b_3$:

(SEQ ID NO: 60)
5'-GGTACCTGTCATCCACGGACCAGCTGA-3'.

Briefly, the PCR reaction mixture was set up in a total volume of 50 µl with the following components: 1-3 µl cDNA, 5 pmol of MJ1-3 primer mixture, 5 pmol of $CH_2$ or $CH_2b_3$ primers, 5 µl of 10× reaction buffer, 1 µl of 10 mM dNTP, 2.5 unit of Taq DNA polymerase (Hoffmann-La Roche, Mississauga, ON, Canada). The PCR protocol consisted of an (i) initial step at 94° C. for 3 min, (ii) followed by 30 cycles of 94° C. for 1 min, 55° C. for 30 s, 72° C. for 30 s and (iii) a final extension step at 72° C. for 7 min. The amplified PCR products were run in a 2% agarose gel and two major bands were observed: a band of about 850 bp, corresponding to conventional IgG, and a second band of around 600 bp, corresponding to heavy chain antibodies. The smaller bands were cut and purified using the QIA-QUICK Gel Extraction Kit (QIAGEN) and reamplified in a second PCR in a total volume of 50 µl using 1 µl of DNA template, 5 pmol of each of MJ7 primer (5'-CATGTGTA-GACTCGCG GCCCAGCCGGCCATGGCC-3' SEQ ID NO:61) and MJ8 primer (5'-CATGTGTAGATTCCTGGC-CGGCCTGGCCTGAGGAGACGGTGACCTGG-3' SEQ ID NO:62), 5 µl of 10× reaction buffer, 1 µl of 10 mM dNTP, 2.5 unit of Taq DNA polymerase. The PCR protocol consisted of (i) an initial step at 94° C. for 3 min, (ii) followed by 30 cycles of 94° C. for 30 s, 57° C. for 30 s and 72° C. for 1 min and (iii) a final extension step at 72° C. for 7 min. The amplified PCR products, ranging between 340 bp and 420 bp and corresponding to $V_H$H fragments of heavy chain antibodies, were purified using the QIAQUICK PCR Purification Kit (QIAGEN), digested with SfiI restriction enzyme (New England BioLabs, Pickering, ON, Canada) and re-purified using the same kit.

Eighty micrograms of pMED1 phagemid (Arbabi-Ghahroudi et al, 2009c) was digested with SfiI overnight at 50° C. To minimize self-ligation, 20 units of XhoI and PstI restriction enzymes were added and the digestion reaction was incubated for an additional 2 h at 37° C. Sixty micrograms of digested phagemid DNA was ligated with 6 µg of digested $V_H$H fragments for 3 h at room temperature using LigaFast Rapid DNA Ligation System (Promega, Madison, Wis.) and its protocol. The ligated materials were purified using the QIAQUICK PCR Purification Kit in a final volume of 100 µl and electroporated in 5 µl portions into commercial electrocompetent TG1 *E. coli* cells (Stratagene, La Jolla, Calif.) as described (Arbabi-Ghahroudi et al, 2009c). The size of the library was determined (Arbabi-Ghahroudi et al, 2009c) to be 5×10⁷. Colony-PCR and sequencing involving 20 colonies showed all tested clones had unique $V_H$Hs (Arbabi-Ghahroudi et al, 2009c). The library was grown for 2 h at 37° C., 250 rpm in the presence of 2% (w/v) glucose. The bacterial cells were pelleted, resuspended in 2×YT/Amp/Glu (2×YT medium with 100 µg/ml ampicillin and 2% (w/v) glucose) with 35% (v/v) glycerol and stored at −80° C. in small aliquots.

Panning experiments were essentially performed as described (Arbabi et al, 1997). Five milliliters of the library (1.5×10⁸ cells) was thawed on ice and grown in 2×YT/Amp/Glu for about 2 h at 37° C. ($A_{600}$=0.4-0.5). Cells were subsequently infected with 20× excess M13KO7 helper phage (New England Biolabs) for 1 h at 37° C. The culture was then centrifuged at 4° C. and infected cell pellets were resuspended in 200 ml of 2×YT/Amp with 50 µg/ml kanamycin and incubated at 37° C. and 250 rpm. The phage particles in culture supernatant were incubated with ⅕ volume of 20% PEG 6000/2.5M NaCl on ice for 1 h and centrifuged at 10,000 rpm for 15 min. The phage pellets were resuspended in 1.5 ml of sterile PBS, titrated and used as input phage for panning. For panning, 96-well MAXISORP plates were coated with 20 µg of TcdA-RBD-f1 or TcdB-RBD-f1 overnight at 4° C. The wells were rinsed with PBS and blocked with PBS/1% (w/v) casein for 2 h at 37° C. Approximately 10¹² phage was added to the blocked wells and incubated for 2 h at 37° C. After 10× washing with PBS/0.1% (v/v) TWEEN 20, the bound phage was eluted with 0.1 M triethylamine, neutralized and mixed with exponentially growing TG1 cells. Titration of eluted phage was performed and infected bacterial cells were superinfected with M13 K07 and grown overnight at 37° C. The purified phage from the overnight culture was used as the input for the next round of panning. The panning was continued for three more rounds following the same procedure except that the amount of coated RBD-fragments was reduced to 15 µg, 10 µg and 5 µg for the second, third and fourth rounds of panning, respectively.

Individual TG1 colonies obtained after round four of panning were subjected to phage ELISA screening, essentially as described elsewhere (Doyle et al, 2008), with the exception that 5 µg/ml of toxin (TcdA and TcdB) and recombinant fragments (TcdA-RBD-f1 and TcdB-RBD-f1) were coated onto microtiter plates. All positive clones were sent for DNA sequencing. Unique clones that gave high phage ELISA signals were selected for large-scale expression and purification. Seven unique TcdA-specific and 7 unique TcdB-specific binders, all determined to be $V_H$Hs based on the presence of characteristic amino acids at positions 42, 49, 50 and 52 (FIG. 2), were selected.

EXAMPLE 4

Expression and Purification of Selected $V_H$Hs

The unique TcdA-specific and TcdB-specific binders of Example 3 were sub-cloned into expression plasmids for protein expression and purification.

Phagemid vectors containing the DNA of selected $V_H$H clones were purified using the QIAPREP MiniPrep Kit, Of the 14 $V_H$Hs, 11 clones were PCR amplified from the pMED1 phagemid vector with either BbsI1-$V_H$H (5'-TATGAAGACACCAGGCCCAGGTAAAGCTGGAG-GAGTCT-3' SEQ ID NO:63) or BbsI2-$V_H$H (5'-TATGAAGACACCAGGCCCAGGTGCAGCTGGTGGAGTCT-3' SEQ ID NO:64) sense primers and BamHI-$V_H$H (5'-TTGT-TCGGATCCTGAGGAGACGGTGACCTG-3' SEQ ID NO:65) antisense primer. These PCR fragments were digested with BbsI and BamHI restriction enzymes and ligated into the similarly digested pSJF2H expression vector (Arbabi-Ghahroudi et al, 2009b). Three of the 14 clones contained internal BbsI or BamHI sites and were cloned into the pMED2 expression vector via digestion with SfiI. The vector pMED2 is a modified version of pSJF2H which contains SfiI restriction enzyme sites in its multiple cloning site. Since $V_H$H sequences in pMED1 are flanked with SfiI restriction sites, no PCR amplification was required for sub-cloning. Upon ligation, all plasmids were transformed into electro-competent TG1 *E. coli* and selected on LB agar plates+100 µg/ml ampicillin. Colonies were screened by colony PCR for inserts and the DNA sequenced.

$V_H$Hs were expressed using the 5-day M9 minimal media method (Arbabi-Ghahroudi et al, 2009c). After induction of protein expression, cell cultures were harvested at 6,000 rpm×30 min (4° C.), the supernatant decanted, and the periplasmic contents extracted from the cell pellet. Briefly, each pellet was resuspended in 30 ml of ice-cold TES buffer (0.2 M Tris-HCl buffer pH 8.0, 20% (w/v) sucrose, 0.5 mM EDTA) and incubated on ice for 30 min. Next, 40 ml of ice-cold 1/8 TES was added, incubated an additional 30 min on ice and the slurry centrifuged at 12,000 rpm for 30 min (4° C.). The resulting supernatant was dialysed overnight into IMAC buffer A (10 mM HEPES buffer pH 7.0, 500 mM NaCl) and purified as previously described (Hussack et al, 2009). Eluted fractions were analyzed by SDS-PAGE and Western blotting before being dialysed into PBS. $V_H$H concentrations were determined by absorbance measurements at 280 nm using theoretical MW and extinction coefficients calculated with the ExPASy ProtParam Tool (http://expasy.org/tools/protparam.html) (Pace et al, 1995).

The expression of the anti-TcdA and anti-TcdB $V_H$H was targeted to the periplasm of TG1 *E. coli* and purified (FIG. 1E) with yields ranging from 1.2-72.3 mg/l bacterial culture (Table 1, Example 7).

EXAMPLE 5

Pentabody Expression and Purification

Two TcdA-specific pentameric $V_H$Hs (pentabodies) were constructed as previously described (Zhang et al, 2004b), using the vector pVT2 which contains the verotoxin B (VTB) subunit pentamerization domain. Pentabodies were expressed in TG1 *E. coli*, as described in Example 4, the cells were lysed and processed as previously described (Hussack et al, 2009), and proteins purified with HITRAP IMAC columns using an imidazole gradient (0-500 mM) for elution. The pentabodies were constructed base on the highest affinity anti-TcdA $V_H$Hs, A5.1 and A20.1 (FIG. 3). The resulting pentabodies are referred to hereafter as A5.1p and A20.1p.

EXAMPLE 6

Enzyme-Linked Immunosorbant Assay (ELISA)

ELISA experiments were used to characterize the binding of $V_H$H monomers and pentamers of Examples 4 and 5, as well as their ability to recognize natural and recombinant antigen.

ELISA was used to determine if the purified anti-toxin $V_H$H monomers recognized native TcdA or TcdB and recombinant TcdA-RBD-f1 or TcdB-RBD-f1 fragments.

Equivalent molar concentrations of proteins (BSA, TcdA, TcdB, TcdA-RBD-f1, and TcdB-RBD-f1) were coated overnight in 96 well microtiter plates at 4° C. The next day, wells were blocked with 3% (w/v) skim milk diluted in PBS-T. After washing with PBS-T, purified $V_H$Hs at concentrations as high as 10 µg/ml were added to wells with the various coated antigens for 1 h at 37° C. Wells were washed with PBS-T, rabbit anti-His$_6$ IgG conjugated with HRP (1:2,500 in PBS) added for 1 h at room temperature and the wells were washed an additional 5× with PBS-T. Rabbit anti-His$_6$ IgG-HRP did not recognize the N-terminal His$_6$ epitope tags on recombinant RBD fragments (data not shown). Binding was detected with TMB substrate (KPL), the reactions were stopped with 1 M H$_3$PO$_4$ and absorbance read at 450 nm. All conditions were performed in triplicate and the reported values are representative of two independent experiments.

ELISA demonstrated that 6 of 7 anti-TcdA $V_H$Hs recognized native TcdA and TcdA-RBD-f1 and that none of the $V_H$Hs cross-reacted with TcdB or TcdB-RBD-f1 (FIG. 4A). Of the 7 anti-TcdB $V_H$Hs tested, 4 recognized TcdB and TcdB-RBD-f1 and one clone (B5.2) also recognized TcdA (FIG. 4B). ELISA experiments were also performed by coating 5 µg/ml of TcdA in microtiter wells and serially diluting $V_H$Hs from 10 µg/ml to 1 ng/ml (FIGS. 4C-D). The remaining detection steps were performed as described above. With this ELISA, which was performed at a higher $V_H$H concentration, a fifth $V_H$H, B15.3, was shown to bind to TcdB.

A second ELISA was used to compare the activities of monomeric and pentameric $V_H$Hs for TcdA. TcdA (5 µg/ml) was coated overnight in 96 well microtiter plates and blocked with 3% milk, before addition of equivalent molar concentrations of $V_H$H monomers and pentamers. $V_H$H binding to TcdA was detected with HRP-labelled rabbit-anti-His$_6$ IgG and TMB substrate. Binding of the pentamers to immobilized TcdA by ELISA was similar to monomeric versions of the same $V_H$Hs (FIG. 3).

EXAMPLE 7

Size Exclusion Chromatography and Surface Plasmon Resonance Analysis

The affinity of the TcdA- and TcdB-specific $V_H$Hs of Example 4 to their respective antigens was determined by surface plasmon resonance (SPR).

Figure 5:
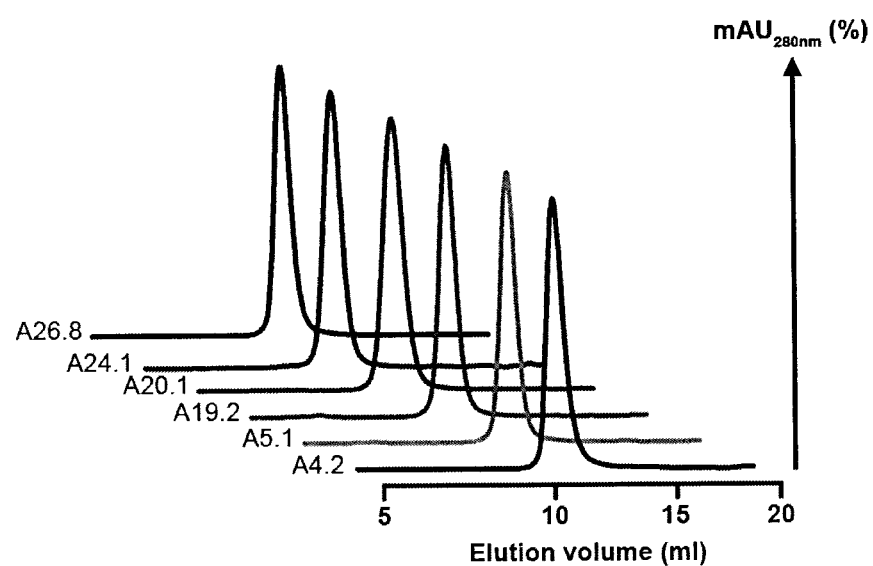
FIG. 5 shows the gel filtration profiles of anti-TcdA V$_H$Hs obtained from a Superdex™ 75 column. The single peak for all WT V$_H$Hs suggests all are non-aggregating monomeric species.

Size exclusion chromatography was performed on all purified $V_H$Hs using a SUPERDEX 75 size exclusion column (GE Healthcare) as previously described (To et al, 2005) under the control of an AKTA FPLC. Briefly, $V_H$Hs were applied at concentrations ranging from 0.75-1 mg/ml (≅45-60 µM) with a flow rate of 0.5 ml/min in a mobile phase that consisted of HBS-EP running buffer (10 mM HEPES, pH 7.4, 150 mM NaCl, 3 mM EDTA, and 0.005% (v/v) P20 surfactant). As expected, all were non-aggregating monomers (FIG. 5).

Fractions from the size exclusion column were then used for affinity measurements. The binding kinetics for the interaction of anti-toxin $V_H$Hs and TcdA or TcdB were determined by surface plasmon resonance using a BIA-CORE 3000 biosensor system (GE Healthcare). A total of 10,377 resonance units (RUs) of TcdA and 5,980 RUs of mouse IgG 13D9 control (Liu et al, 2000) were immobilized on a CM5 sensor chip (GE Healthcare). Anti-TcdA $V_H$H affinity measurements were carried out in HBS-EP running buffer (10 mM HEPES pH 7.4, 150 mM NaCl, 3 mM EDTA and 0.005% (v/v) P20 surfactant) at a flow rate of 40 µl/min. Surfaces were regenerated by washing with either running buffer or 10 mM glycine pH 2.0. Initial attempts to immobilize TcdB directly onto a CM5 sensor chip were unsuccessful due to the toxin's low pI (theoretical pI=4.42). TcdB was therefore biotinylated with the EZ-LINK Sulfo-NHS-LC-LC-Biotin kit from Pierce (Rockford, Ill.) and 825 RUs were immobilized onto a streptavidin-coated CM5 sensor chip. However, due to the size difference of TcdB-biotin (269 kDa) compared to streptavidin (53 kDa), not all streptavidin sites were occupied and roughly 1 TcdB-biotin was immobilized for every 7 streptavidin molecules. Furthermore, no binding was observed between the anti-TcdB $V_H$Hs and immobilized TcdB-biotin. Data on the $V_H$H-TcdB-RBD-f1 interaction was collected by immobilizing TcdB-specific $V_H$Hs onto the CM5 sensor chip (RUs ranging from 215 to 1209) and injecting TcdB-RBD-f1 at 20 µl/min. The IgG 13D9 or human single-domain antibody HVHP420 (To et al, 2005) served as controls. In all cases, data were analyzed with BIAevaluation 4.1 software (GE Healthcare).

Figure 6:
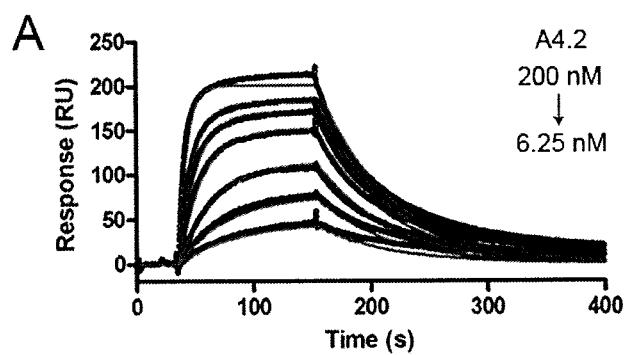
FIG. 6 shows surface plasmon resonance analysis of anti-TcdA/B V$_H$Hs. Sensorgrams of TcdA-specific V$_H$Hs A4.2, A5.1, A19.2, A20.1, A24.1 and A26.8 binding to immobilized TcdA (FIGS. 6A-F) and TcdB-RBD-f1 (FIG. 1) binding to immobilized TcdB-specific V$_H$Hs B5.2, B13.6 and B15.5 (FIGS. 6G-I) are shown. In experiments involving TcdA-specific V$_H$Hs, TcdA was immobilized on CM5-dextran chips and monomeric V$_H$Hs were passed over at concentration ranges noted on each sensorgram, giving affinity constants ranging from 2 nM to 290 nM. In experiments involving TcdB-specific V$_H$Hs, antibodies were immobilized on CM5-dextran chips and TcdB-RBD-f1 ranging in concentration from 2 µM to 200 nM was passed over, giving affinity constants ranging from 100 nM to 400 nM. Black lines represent raw data measurements and grey lines represent fitted curves. All data presented here showed acceptable fitting to a 1:1 binding model. Rate and affinity constants are shown in Table 1.
Figure 6:
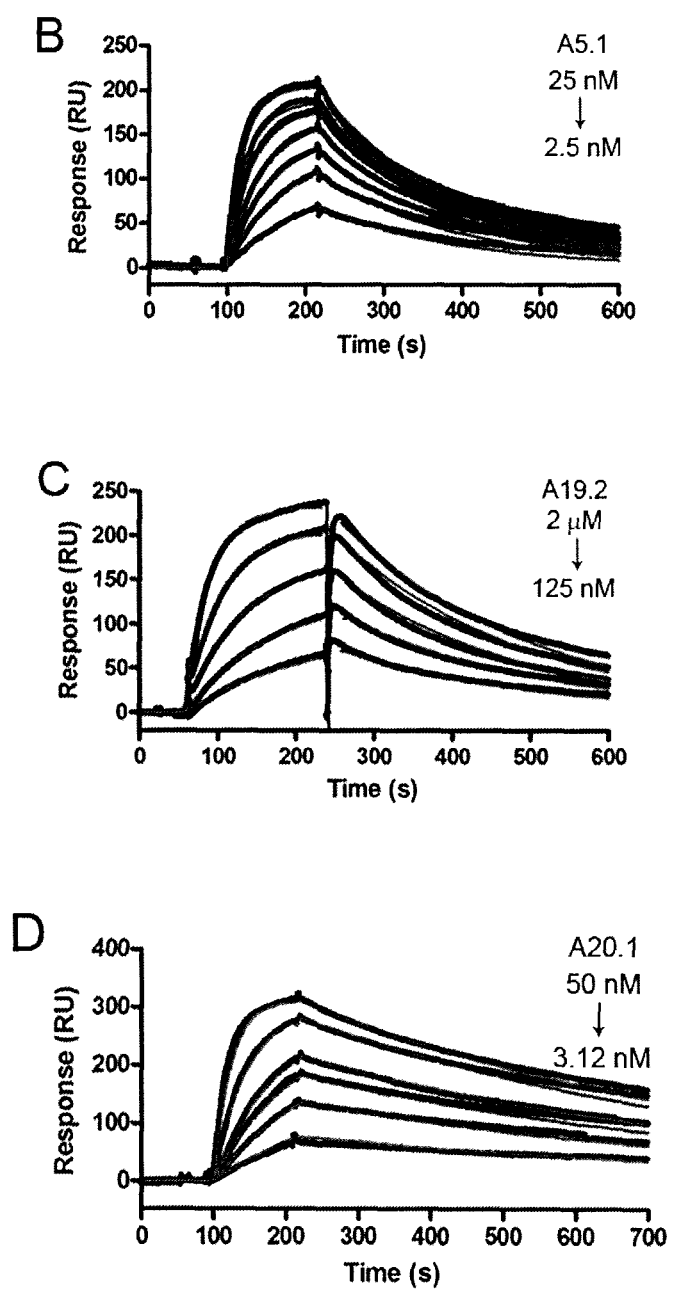
Figure 6:
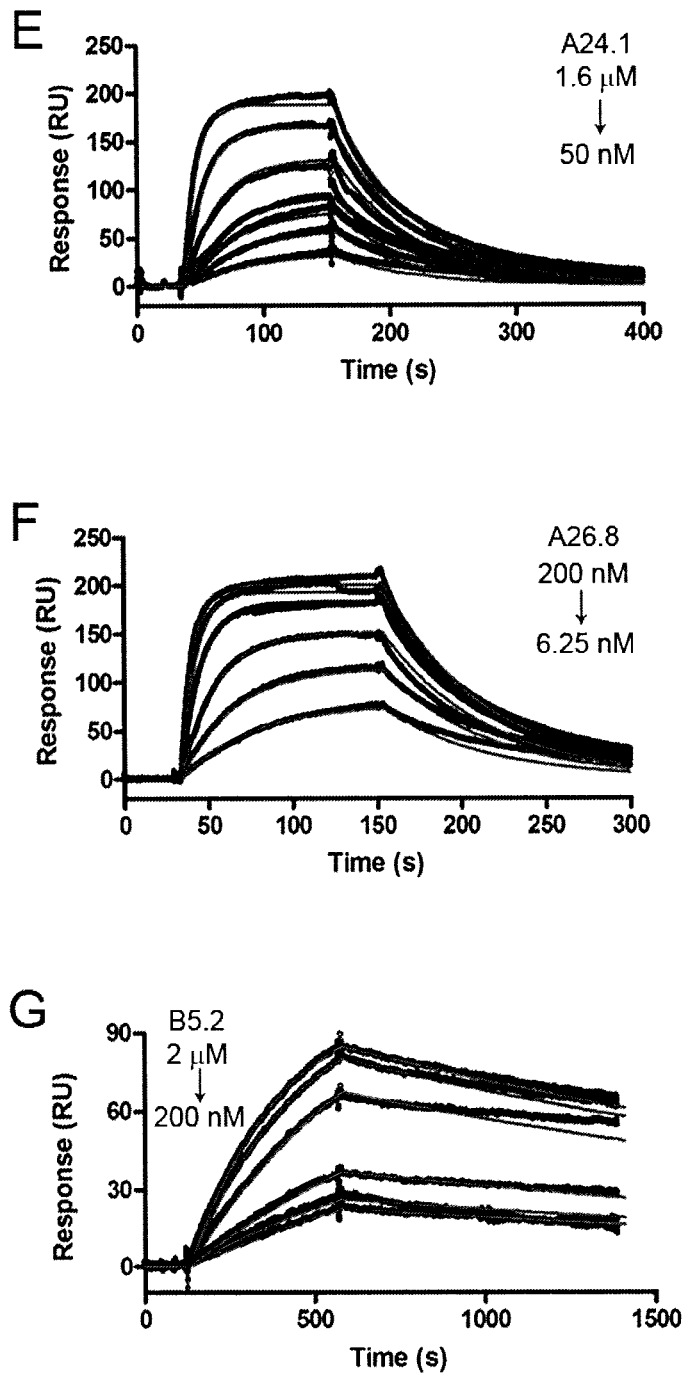
Figure 6:
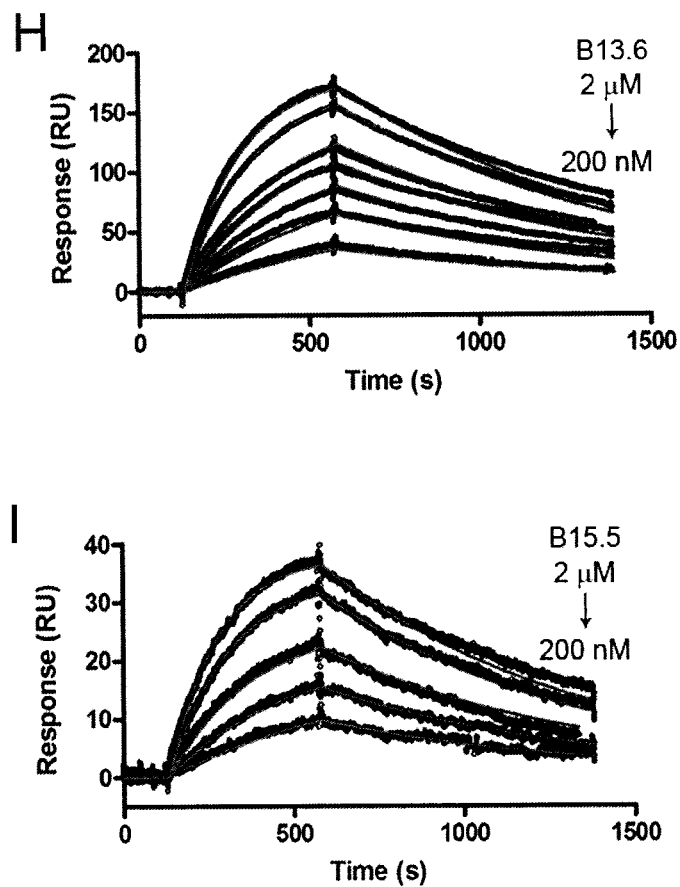

Surface plasmon resonance (SPR) analysis revealed 6 of 7 anti-TcdA $V_H$Hs specifically bound TcdA with equilibrium dissociation constants ranging from 290 nM for A19.2 to 2 nM for A20.1 (FIG. 6). Observed $V_H$H affinities for TcdA were strong, with four of the clones having $K_D$ values ranging from 2 to 24 nM (Table 1). The anti-TcdA $V_H$Hs isolated here are among the highest affinity proteinaceous toxin-binding single-domain antibodies characterized to date (Stewart et al, 2007; Goldman et al, 2006; Liu et al, 2007a; Hmila et al, 2008; Goldman et al, 2008; Anderson et al, 2008).

Figure 7:
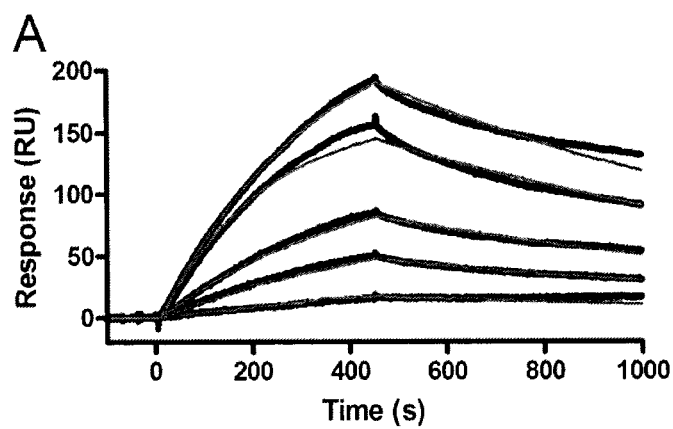
FIG. 7 shows a subset of TcdB-specific V$_H$Hs with complex binding to recombinant TcdB-RBD. Surface plasmon resonance sensorgrams for V$_H$Hs that showed binding to TcdB-RBD-f1, but whose data was non analyzable. The recombinant TcdB-RBD-f1 fragment (2 µM→200 nM) was passed over immobilized V$_H$Hs (526-1209 RUs). (A) B7.3, (B) B13.2, (C) B13.3, and (D) B15.3.
Figure 7:
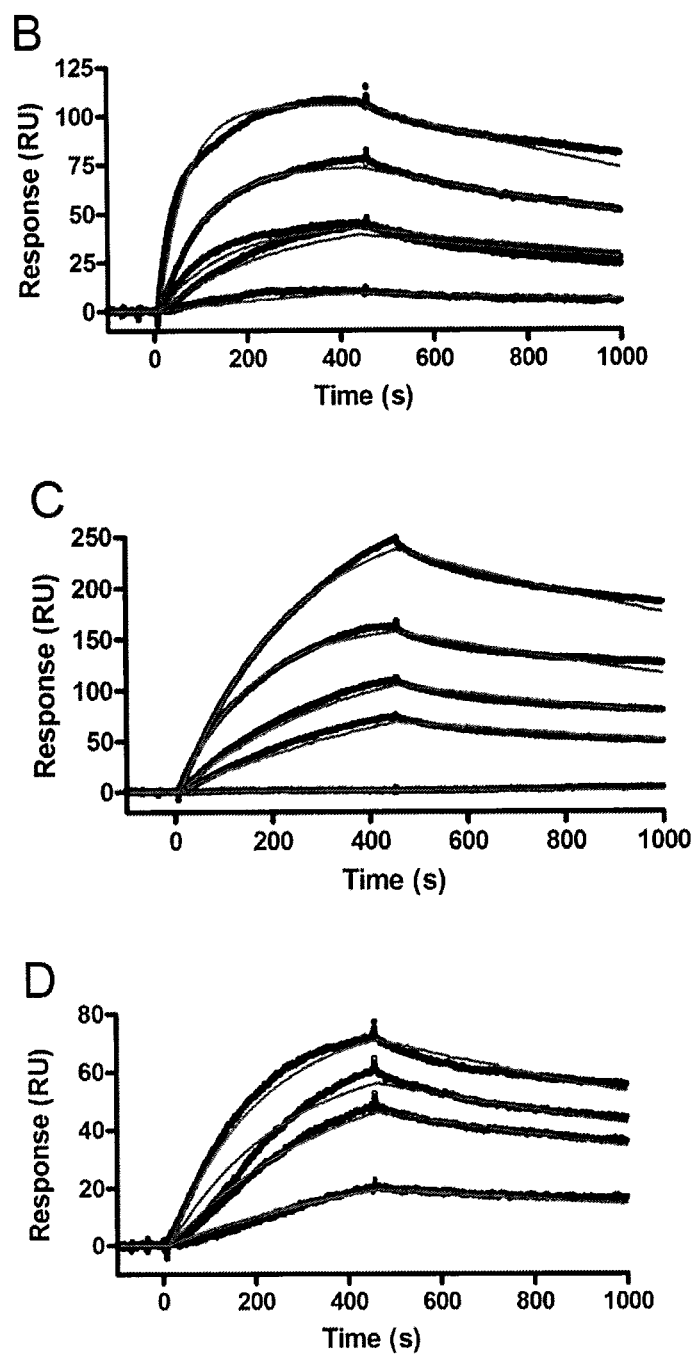

Analyzing the TcdB-binding $V_H$Hs by SPR was more challenging. Initial attempts to immobilize TcdB onto the CM5 dextran biosensor chip may have been hindered by the low theoretical pI of TcdB. An attempt to biotinylate TcdB for immobilization on a streptavidin-coated biosensor chip was equally as unsuccessful. To circumvent this problem, anti-TcdB $V_H$Hs were immobilized directly onto the CM5 dextran chips and data collected using various concentrations of TcdB-RBD-f1. Analyzable data could only be collected for 3 of 7 anti-TcdB $V_H$Hs, with affinity constants ranging from 100 nM to 400 nM (FIG. 6; Table 1). Specific binding was detected for the other 4 anti-TcdB $V_H$Hs, however, the data was non-analyzable (FIG. 7).

TABLE 1

Properties of anti-*C. difficile* toxin A and B $V_H$H single-domain antibodies.

| $V_H$H | MW (kDa) | pI[a] | Expression Yield (mg/l) | $k_{on}$ (M$^{-1}$s$^{-1}$) | $k_{off}$ (s$^{-1}$) | $K_D$ (nM) | Neutralizing? |
|---|---|---|---|---|---|---|---|
| A1.3 | 16.75 | 6.71 | 1.4 | NB | NB | NB | No[b] |
| A4.2 | 15.73 | 8.59 | 31.3 | $6.7 \times 10^5$ | $1.6 \times 10^{-2}$ | 24 | Yes |
| A5.1 | 15.80 | 6.71 | 55.5 | $1.6 \times 10^6$ | $5.0 \times 10^{-3}$ | 3 | Yes |
| A19.2 | 16.01 | 8.61 | 3.8 | $1.4 \times 10^4$ | $3.9 \times 10^{-3}$ | 290 | Yes |

TABLE 1-continued

Properties of anti-*C. difficile* toxin A and B $V_HH$ single-domain antibodies.

| $V_HH$ | MW (kDa) | pI[a] | Expression Yield (mg/l) | $k_{on}$ (M$^{-1}$s$^{-1}$) | $k_{off}$ (s$^{-1}$) | $K_D$ (nM) | Neutralizing? |
|---|---|---|---|---|---|---|---|
| A20.1 | 16.61 | 6.64 | 72.3 | $8.2 \times 10^6$ | $1.6 \times 10^{-3}$ | 2 | Yes |
| A24.1 | 16.71 | 6.71 | 8.5 | $6.0 \times 10^4$ | $1.6 \times 10^{-2}$ | 260 | Yes |
| A26.8 | 16.02 | 6.65 | 64.9 | $1.4 \times 10^6$ | $1.6 \times 10^{-2}$ | 12 | Yes |
| B5.2 | 15.11 | 6.04 | 6.7 | $2.0 \times 10^3$ | $2.0 \times 10^{-4}$ | 100 | No[b] |
| B7.3 | 16.13 | 8.93 | 1.5 | NB | NB | NB | NA |
| B13.2 | 15.79 | 7.98 | 4.0 | NB | NB | NB | NA |
| B13.3 | 15.62 | 8.00 | 1.6 | NB | NB | NB | NA |
| B13.6 | 15.01 | 8.00 | 3.6 | $2.5 \times 10^3$ | $1.0 \times 10^{-3}$ | 400 | No[b] |
| B15.3 | 15.58 | 8.59 | 1.2 | NB | NB | NB | NA |
| B15.5 | 15.23 | 7.18 | 4.6 | $2.8 \times 10^3$ | $1.0 \times 10^{-3}$ | 357 | No[b] |

[a] Theoretical pI calculated using the ExPASy ProtParam tool (expasy.ch/tools/protparam.html).
[b] Not neutralizing at concentration as high as 1 μM.
NB: no binding detected by Biacore.
NA: not attempted.

EXAMPLE 8

In Vitro Toxin Neutralization Assay

The human lung fibroblast (HLF) cell cytotoxicity assay is routinely used for analyzing the presence of *C. difficile* toxins in biological samples (Babcock et al, 2006). The assay was used here to determine if anti-toxin $V_HHs$ of Example 4 or 5 could neutralize the cytopathic effects of TcdA and TcdB.

HLF cells (ATCC#CCL-186) were purchased from ATCC (Manassas, Va.) and maintained in Eagle's minimal medium (Invitrogen, Carlsbad, Calif.) supplemented with 10% fetal bovine serum (Invitrogen) at 37° C. with 5% $CO_2$. Cells were seeded in sterile 96 well microtiter plates ($2 \times 10^4$ cells 200 μl$^{-1}$ well$^{-1}$) for 20 h, allowing for the formation of confluent monolayers.

Initially, a dose-response experiment was conducted to find the minimum concentration of TcdA and TcdB which induced 100% HLF cell rounding after 24 h post toxin addition. To do so, 10 μl of sterile filtered TcdA or TcdB were added to wells containing confluent monolayers, giving final toxin concentrations ranging from 500 ng/ml to 0.5 ng/ml. Each concentration was performed in triplicate and the assay performed twice. HLF cells were scored visually for rounding at various time points over 24 h. For all subsequent assays, 100 ng/ml of TcdA and 20 ng/ml of TcdB were used.

For experiments involving $V_HHs$, 20 μl of purified and sterile filtered monomeric or pentameric $V_HHs$ were added to HLF cells with 10 μl TcdA/B or 10 μl PBS. For experiments involving combinations of 2 or 3 $V_HHs$, the concentration of each $V_HH$ was reduced by 1/2 and 1/3, respectively, giving the same final concentrations as experiments involving a single $V_HH$. Importantly, $V_HHs$ and toxin were not pre-incubated; rather, each was added directly to HLF monolayers at time=0 h; this was more representative of in vivo scenarios and did not bias the in vitro results by pre-incubating. HLF cells containing PBS, $V_HH$, toxin, or $V_HH$+toxin were scored visually for cell rounding using a confocal microscope at 8 h and 24 h post antibody/toxin addition. Assays were performed in triplicate and repeated twice. Each assay was performed on fresh preparations of HLF cells (passage 3-5) and $V_HHs$ were from separate purifications. The purified TcdA and TcdB stock remained the same for all assays.

Figure 8:
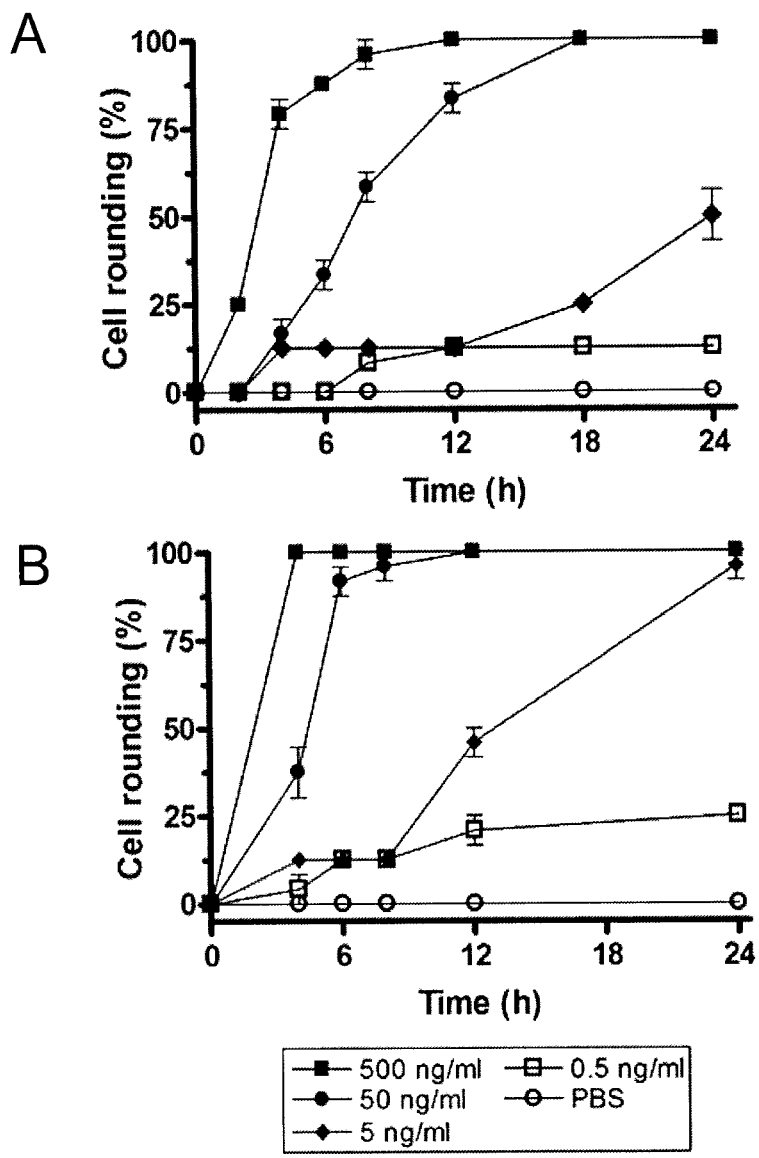
FIG. 8 shows the in vitro neutralization of TcdA cytotoxicity with anti-TcdA V$_H$Hs. Dose-response curves of TcdA (FIG. 8A) and TcdB (FIG. 8B) on monolayers of IMR-90 human lung fibroblast (HLF) cells. The percentage of cell rounding was scored from 0% to 100% of the cells affected.

Human lung fibroblast (HLF) cytotoxicity assays were used to determine whether $V_HHs$ could neutralize TcdA- or TcdB-induced HLF cell rounding. Dose-response experiments with TcdA (FIG. 8A) and TcdB (FIG. 8B) determined the minimum toxin concentrations capable of 100% cell rounding after 24 h to be 50 ng/ml and 5 ng/ml, respectively. For all subsequent experiments, 2× this minimum concentration was used (i.e., 100 ng/ml of TcdA and 10 ng/ml of TcdB). $V_HHs$ had no effect on HLF cells when incubated in the absence of toxin A (FIG. 8F). When $V_HHs$ and TcdA were added simultaneously to HLF cells, 6 of 7 anti-TcdA $V_HHs$ inhibited TcdA-induced cell rounding in a dose-dependent manner at 8 h (data not shown) and 24 h post TcdA addition (FIG. 8C-F). The neutralizing capacity of the 4 strongest monomeric $V_HHs$ (A4.2, A5.1, A20.1 and A26.8) was similar at all concentrations tested, reflective of their close range of $K_D$'s (2-24 nM). The weakest neutralizers, A19.2 and A24.1, also possessed the weakest affinity constants of 290 and 260 nM, respectively. The non-binding A1.3 $V_HH$ did not inhibit cell rounding.

Figure 9:
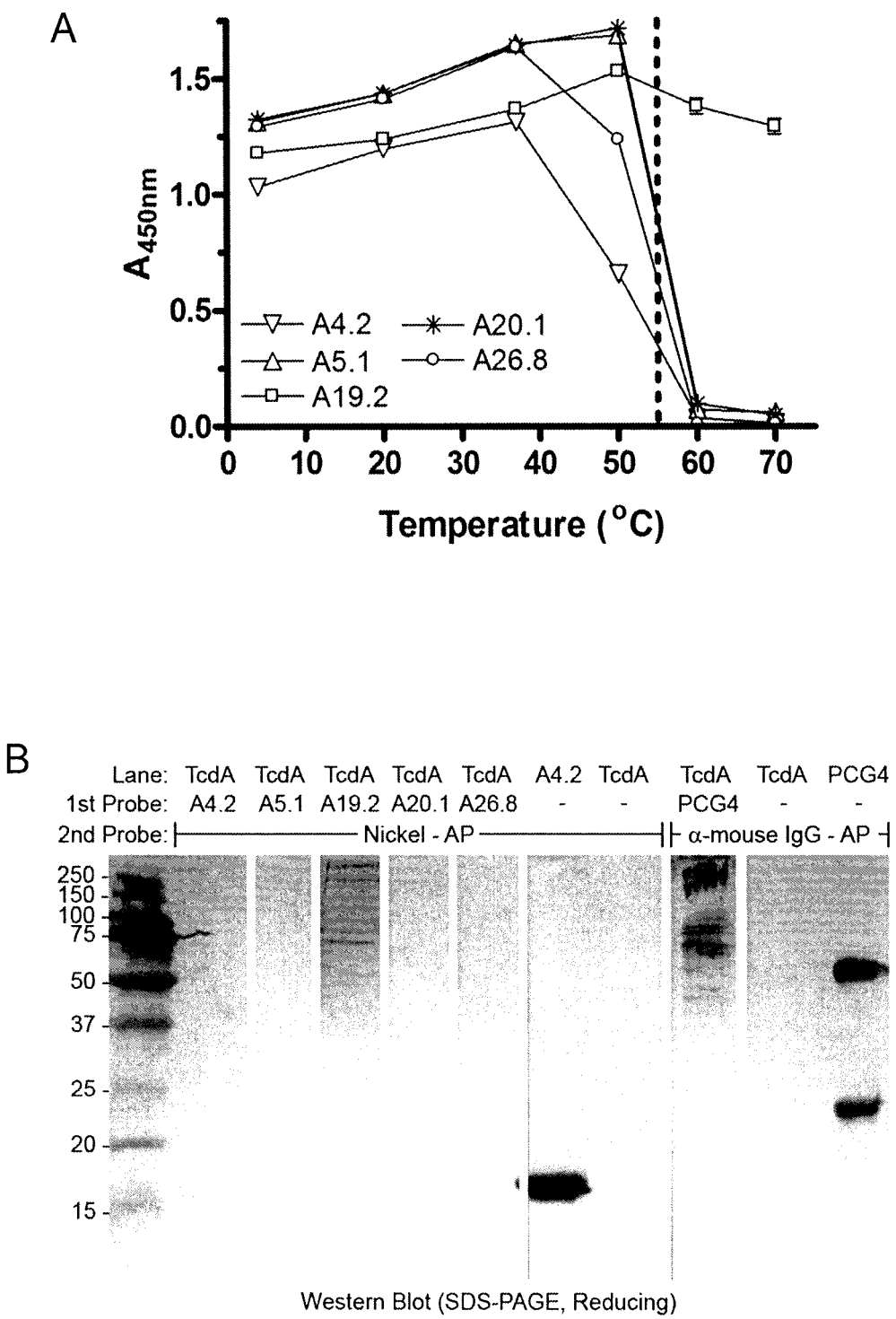
FIG. 9 shows results of epitope typing experiments. Anti-toxin V$_H$Hs recognize conformational (A4.2, A5.1, A20.1, A26.8) and linear (A19.2) epitopes on native C. difficile toxin and recombinant fragments of the cell receptor-binding domain.
Figure 9:
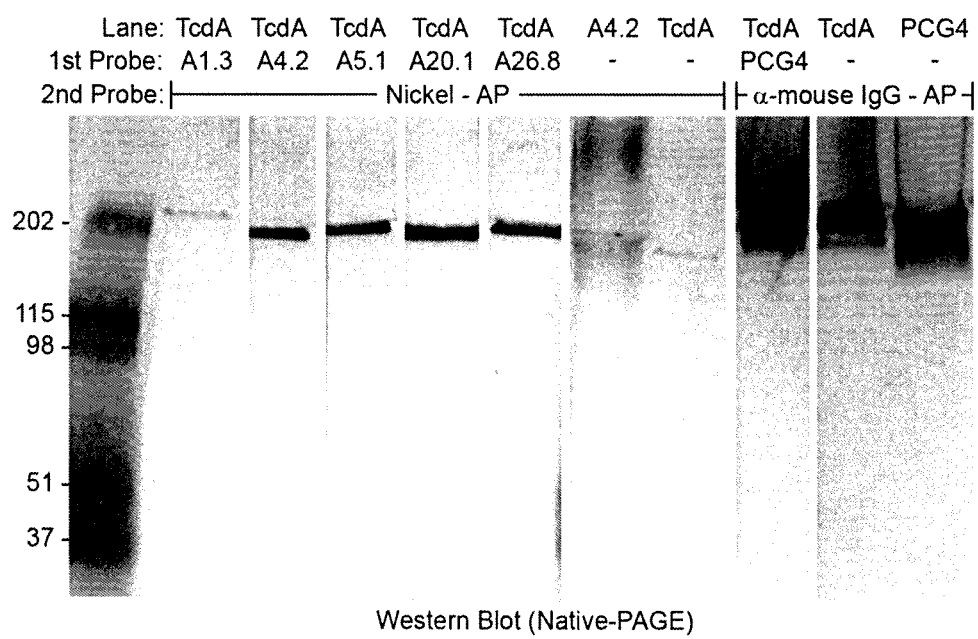
Figure 10A:
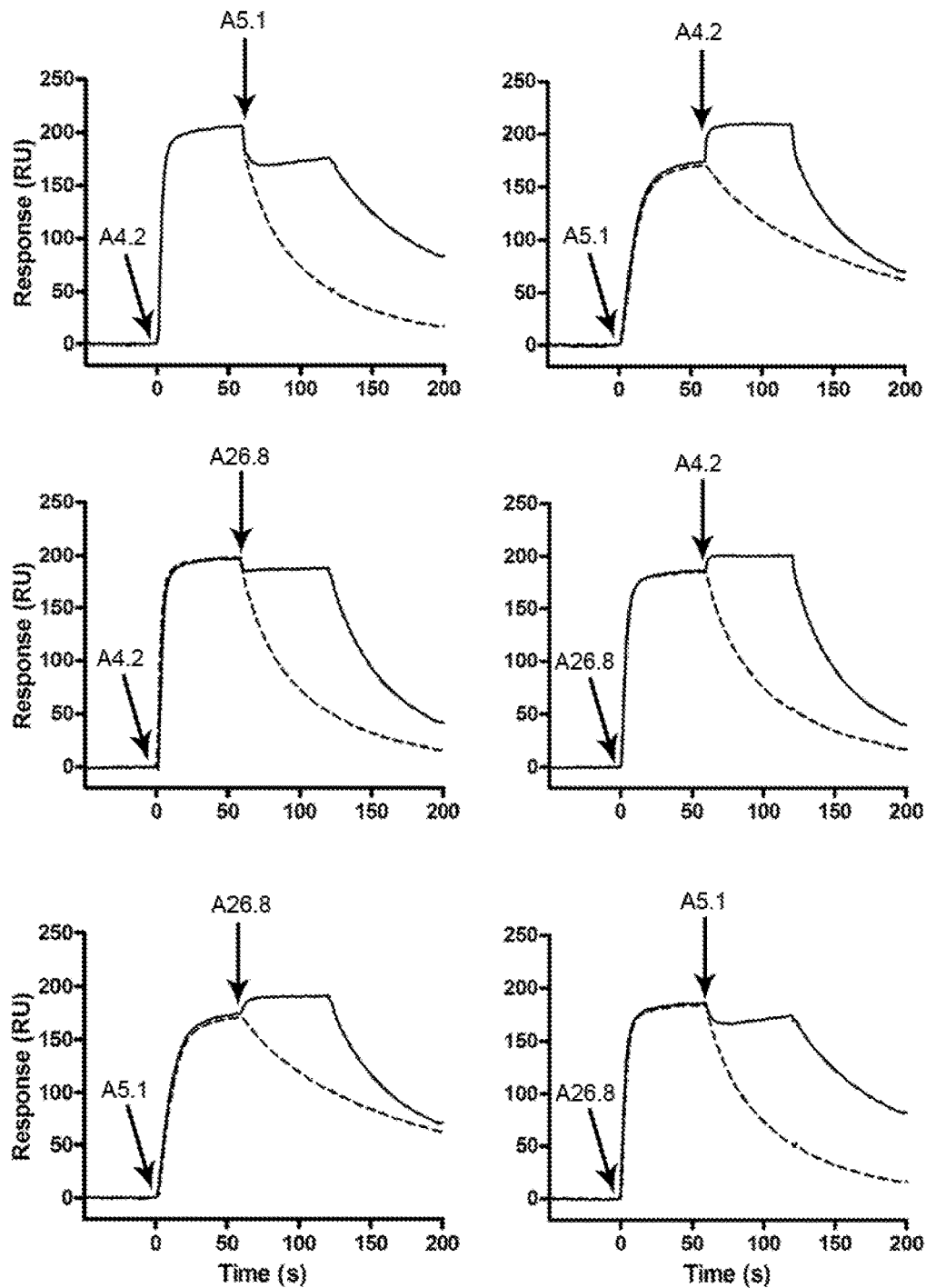
FIG. 10 shows results of Biacore co-injection experiments, which were used to determine if pairs of V$_H$Hs could bind TcdA simultaneously. The Biacore sensorgrams in FIG. 10A and FIG. 10B of all of the possible paired combinations of A4.2, A5.1, A20.1 and A26.8, in both orientations, are shown. Dashed lines represent injection of a single V$_H$H followed by injection of buffer. Solid lines represent co-injections of the first V$_H$H followed by injection of a second V$_H$H. For all experiments, 80 µl of each V$_H$H at a concentration 20× its K$_D$ was injected over 10,287 RUs of immobilized TcdA at 40 µl/min. In general, A4.2, A5.1 and A26.8 appeared to share an overlapping epitope as no significant increase in response was found upon injection of the second species. Conversely, A20.1 appeared to bind a distinct, non-overlapping epitope.
Figure 10B:
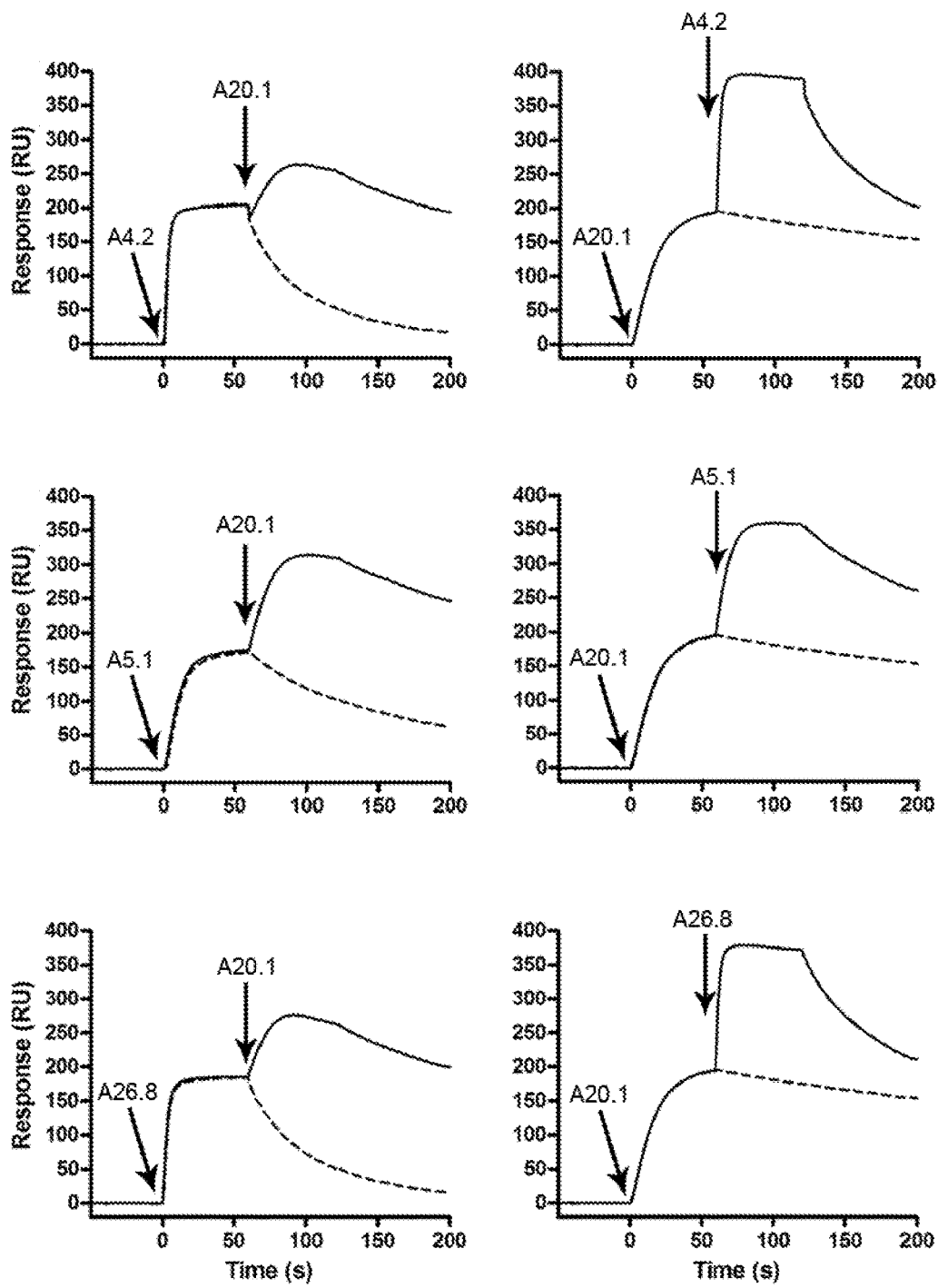

The toxin neutralizing efficacy of various combinations of $V_HHs$ was tested. All possible pair-wise and triplet combinations were tested. When various combinations of A4.2, A5.1, A20.1 and A26.8 were tested, their TcdA neutralizing efficacy was greater than any of the $V_HHs$ alone. These observations suggested the $V_HHs$ recognized distinct epitopes on TcdA, which was subsequently confirmed for A20.1 by co-injection BIACORE surface plasmon resonance (SPR) epitope mapping experiments (FIG. 10). In contrast, the other potent neutralizers appeared to bind to overlapping epitopes on TcdA. These data explain the increased neutralizing capacity seen for pairs and triplet combinations containing A20.1, but do not explain why some pairs (i.e., A5.1/A26.8) or triplet combinations (i.e., A4.2/A5.1/A26.8) show greater efficacy than the individual $V_HHs$. The SPR data indicated a 1:1 binding stoichiometry, which is difficult to reconcile with the observation of enhanced neutralizing efficacy with mixed $V_HHs$ binding to overlapping epitopes. The binding stoichiometry determination assumes a mainly active toxin surface, which may not be the case since the toxin preparations showed breakdown products (FIG. 1B and FIG. 9B/C).

Pentabodies A5.1p and A20.1p, were also tested for toxin neutralizing efficacy. Surprisingly, the pentabodies showed similar neutralizing efficacy to their monomeric counterparts at the same concentration (data not shown). While it is possible that size effects increased the hindrance of TcdA binding to cell receptors, this effect on neutralizing potency may have been offset with a reduction in effective $V_HH$ concentration. For example, if only 1 of 5 $V_HH$ molecules could bind TcdA, the number of total $V_HH$s available for TcdA binding would be reduced by 5-fold.

The neutralizing capacity of the anti-TcdB $V_HH$s was also tested. None of the 3 TcdB-specific $V_HH$s were capable of TcdB neutralization, even at a concentration of 1 µM (data not shown). It is not clear whether the $V_HH$ affinity was insufficient for neutralization, or if the epitopes these $V_HH$s were raised against was not capable of preventing TcdB binding to fibroblast cell receptors. SPR Data was only collected for the TcdB-RBD-f1-$V_HH$ interaction; it is possible that the $V_HH$ affinities for TcdB may be considerably lower and this could account for poor neutralization.

The structure of TcdA-RBD contains 7 putative carbohydrate binding sites (Greco et al, 2006; Ho et al, 2005), which are thought to interact with epithelial cell surface receptors to mediated endocytosis (Florin and Thelestam, 1983). Due to geometric constraints, all 7 sites cannot access the cell-surface receptors simultaneously, although multiple (<7) low affinity interactions are predicted (Greco et al, 2006). As such, avidity appears to be crucial to the strength of toxin binding to its cellular receptors. It was hypothesized that pooling of neutralizing $V_HH$s which recognized distinct epitopes on TcdA-RBD may enhance neutralizing potency through greater hindrance of toxin-cell receptor contacts. When various combinations of A4.2, A5.1, A20.1 and A26.8 were tested, their TcdA neutralizing efficacy was greater than any of the $V_HH$s alone. These observations suggested the $V_HH$s recognized distinct epitopes on TcdA, which was subsequently confirmed for one $V_HH$ (A20.1) by co-injection Biacore epitope mapping experiments (Example 9).

EXAMPLE 9

Epitope Mapping

To gain insight into whether the TcdA-specific $V_HH$s recognized a linear or conformational epitope on TcdA, and whether the $V_HH$s could bind unique, non-overlapping epitopes, a combination of Western blotting, ELISA, and SPR was used.

Western blots using both denaturing SDS-PAGE and native PAGE, and containing TcdA were probed with anti-TcdA $V_HH$s or control anti-TcdA IgG (PCG4; Novus Biologicals, Littleton, Colo.) to determine if the $V_HH$s recognized linear or conformational epitopes. For denaturing SDS-PAGE Western blots, TcdA (0.75 µg/lane), A4.2 $V_HH$ (1 µg/lane) and PCG4 IgG (1 µg/lane) were separated on 12.5% SDS-PAGE gels under reducing conditions and transferred to PVDF membranes at 100 V for 1 h. Membranes were blocked for 1 h with 5% (w/v) BSA diluted in PBS-T followed by probing with various $V_HH$s (25 µg/10 ml blocking buffer) or PCG4 (10 µg/10 ml blocking buffer) for 1 h. Membranes were washed 4× in PBS-T followed by addition of either: (i) mouse anti-His$_6$ IgG-alkaline phosphatase (AP) conjugate (Abcam, Cambridge, Mass.) diluted 1:5,000 in blocking buffer, (ii) HisDetector Nickel-AP conjugate (Mandel Scientific, Guelph, ON, Canada) diluted 1:5,000 in blocking buffer, or (iii) goat anti-mouse IgG-AP conjugate (Cederlane, Burlington, ON, Canada) diluted 1:10,000 in blocking buffer for 1 h. After a final set of 4 washes, membranes were subjected to AP substrate (Bio-Rad, Hercules, Calif.) for 7 min, washing in dH$_2$O and air drying. For native PAGE Western blots, TcdA, $V_HH$ and PCG4 (concentrations as above) were separated on 8% PAGE gels (without SDS) at 100 V for 2 h on ice. Next, gels were transferred to PVDF membranes at 20 V for 14 h at 4° C. Membranes were blocked, probed, washed and detected using the same protocol as for SDS-PAGE Western blots.

Only A19.2 $V_HH$ recognized TcdA run under denaturing/reducing conditions (FIG. 9B). The anti-TcdA mAb PCG4 (Lyerly et al, 1986), which was previously shown to recognize TcdA in Western blots (Ochsner et al, 2009), confirmed that TcdA was transferred to the blot. The weak signal obtained from A19.2 relative to PCG4 was likely due to the low affinity and/or lack of avidity of A19.2 for TcdA. In the absence of primary antibody, the secondary conjugates Nickel-AP and goat anti-mouse IgG-AP did not bind TcdA as expected. The $V_HH$ A4.2 and PCG4 were included to confirm the functionality of the secondary conjugates. Under non-denaturing conditions (native PAGE), $V_HH$ binding to TcdA was originally probed with anti-His$_6$ IgG-AP and this secondary antibody was found to cross-react with TcdA in the absence of $V_HH$ (data not shown). To overcome this, the secondary antibody was replaced with Nickel-AP. Using this secondary conjugate, the $V_HH$s A4.2, A5.1, A20.1 and A26.8 recognized native TcdA while the non-binding A1.3 essentially did not react with TcdA (FIG. 9C). The Nickel-AP secondary conjugate did not bind native TcdA in control blots. The diffuse signal and poor migration pattern of A4.2 $V_HH$ control is likely due to its high pI (theoretical pI: 8.59). To confirm the presence of TcdA on native PAGE blots, PCG4 was used as a control. Just like anti-His$_6$ IgG-AP, the secondary antibody goat anti-mouse IgG-AP also bound TcdA in the absence of the primary probe, PCG4 in this case (FIG. 9C).

To further investigate whether the $V_HH$s recognized linear or conformational epitopes, ELISA was performed with TcdA exposed to various temperature above and below its thermal unfolding midpoint temperature ($T_m$ ~55° C.; Salnikova et al, 2008). Briefly, TcdA (5 µg/ml) was exposed to the following condition for 30 min: 4° C., 20° C., 37° C., 50° C., 60° C. or 70° C. After temperature treatment, 100 µl of TcdA was coated in 96 well microtiter plates overnight at 4° C. and the assay performed essentially as described in Example 6, except that 0.05-1 µg/ml of $V_HH$ was used. All conditions were performed in duplicate and the reported values are representative of two independent experiments.

For 4 of the 5 $V_HH$s, A4.2, A5.1, A20.1 and A26.8, binding to TcdA was completely abolished when TcdA was heated above its $T_m$ (FIG. 9A), confirming the above results that the $V_HH$s recognize a conformational epitope on TcdA. A19.2 was found to bind TcdA with the same strength at all temperature, indicating that this $V_HH$ recognizes a linear epitope. The epitopes must be located in the region of TcdA responsible for cell-receptor binding, since llama immunization and library panning were both performed with TcdA-RBD-f1 and because the $V_HH$s were shown to recognize this recombinant fragment by ELISA (FIG. 4A).

BIACORE surface plasmon resonance (SPR) co-injection experiments were also used to determine if the $V_HH$s could bind unique, non-overlapping epitopes on TcdA. Briefly, 80 µl of the first $V_HH$ diluted in HBS-EP buffer to a concentration of 20× its $K_D$ was injected over 10,287 RUs of immobilized TcdA at 40 µl/min. Following injection of the first $V_HH$, buffer or a second $V_HH$ (80 µl total volume, at 20×$K_D$) was injected at 40 µl/min over the TcdA surface already saturated with the first $V_HH$. Data were collected on all possible paired combinations of A4.2, A5.1, A20.1 and A26.8, in both orientations (i.e., each $V_HH$ acted as the first and second $V_HH$). Data were collected and evaluated as described in Example 7.

Figure 11:
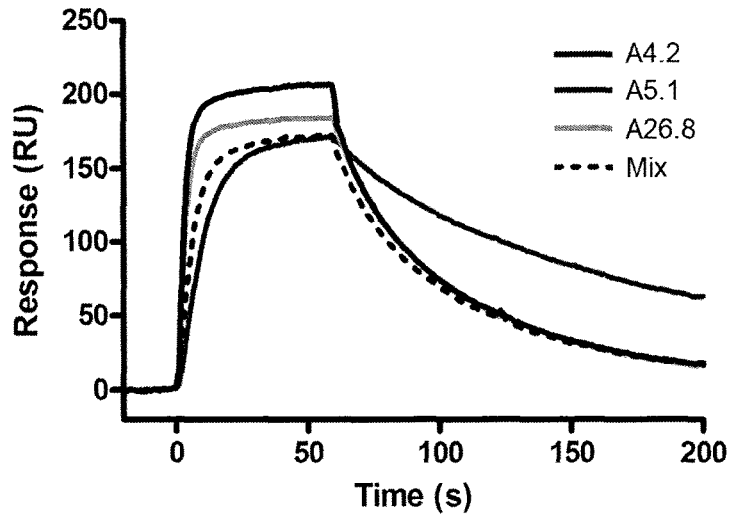
FIG. 11 shows Biacore results indicating that a subset of V$_H$Hs bind TcdA at overlapping epitopes. The three V$_H$Hs suspected of sharing an overlapping epitope (FIG. 7) were injected alone (A4.2, A5.1, or A26.8) and as a triplet mixture ("Mix") over immobilized TcdA. The Biacore sensorgram illustrates similar R$_{max}$ (~160-200 RUs) values for individual V$_H$Hs with no increase in response upon injection of the mixed population, indicating these antibodies recognize an overlapping epitope on TcdA. If the mixture of V$_H$Hs were free to bind at non-overlapping sites, one would expect an R$_{max}$ value for the mixtures to reach the sum of all individual R$_{max}$ values (i.e., ~540 RUs). In all experiments, 80 µl of V$_H$Hs were injected at 40 µl/min and used at 20× their K$_D$ concentrations.

The observation that combining anti-TcdA V$_H$Hs increased TcdA neutralizing efficacy relative to single V$_H$Hs at the same concentration (FIG. 8C-E; Example 8) suggested the antibodies recognized distinct, non-overlapping epitopes. Co-injection BIACORE SPR experiments were performed with pairs of V$_H$Hs, in both orientations, to determine if antibodies could bind TcdA simultaneously (FIG. 10). Of the paired combinations, only those involving A20.1 V$_H$H showed a significant increase in response consistent with theoretical R$_{max}$ values (~160-180 RUs) upon co-injection. This suggests that A20.1 is free to bind TcdA when A4.2, A5.1 or A26.8 are bound at saturating concentrations and also indicates the A20.1 epitope is distinct and does not hinder binding of the other three V$_H$Hs. For A4.2, A5.1 and A26.8, however, only minor changes in response were seen upon co-injection with theoretical R$_{max}$ values not reached, an indication that the V$_H$Hs were binding overlapping epitopes and hindering their binding to TcdA (FIG. 10). This was confirmed by co-injection of all three of these V$_H$Hs simultaneously (FIG. 11).

Taken together, the BIACORE SPR-based epitope mapping studies suggest A20.1 freely binds TcdA at a site that does not overlap with, or is not sterically hindered by, A4.2, A5.1 or A26.8 binding. These latter three V$_H$Hs bind at sites on TcdA that hinder freely accessible binding of the others, suggesting these antibodies share a single epitope, or bind epitopes in such close proximity to one another that it prevents unhindered interaction with TcdA. It is likely that "overlapping" V$_H$Hs recognize repeating epitopes. With mixed V$_H$H, the spatial geometry of binding along the toxin-RBD length at multiple epitope sites is such that it makes them more effective toxin neutralizers than when a single V$_H$H is bound. Thus, despite binding an overlapping epitope, the mixture of V$_H$H geometries would enhance steric effects (and neutralizing capacity) compared to single V$_H$H species which presents a single geometry.

Figure 12:
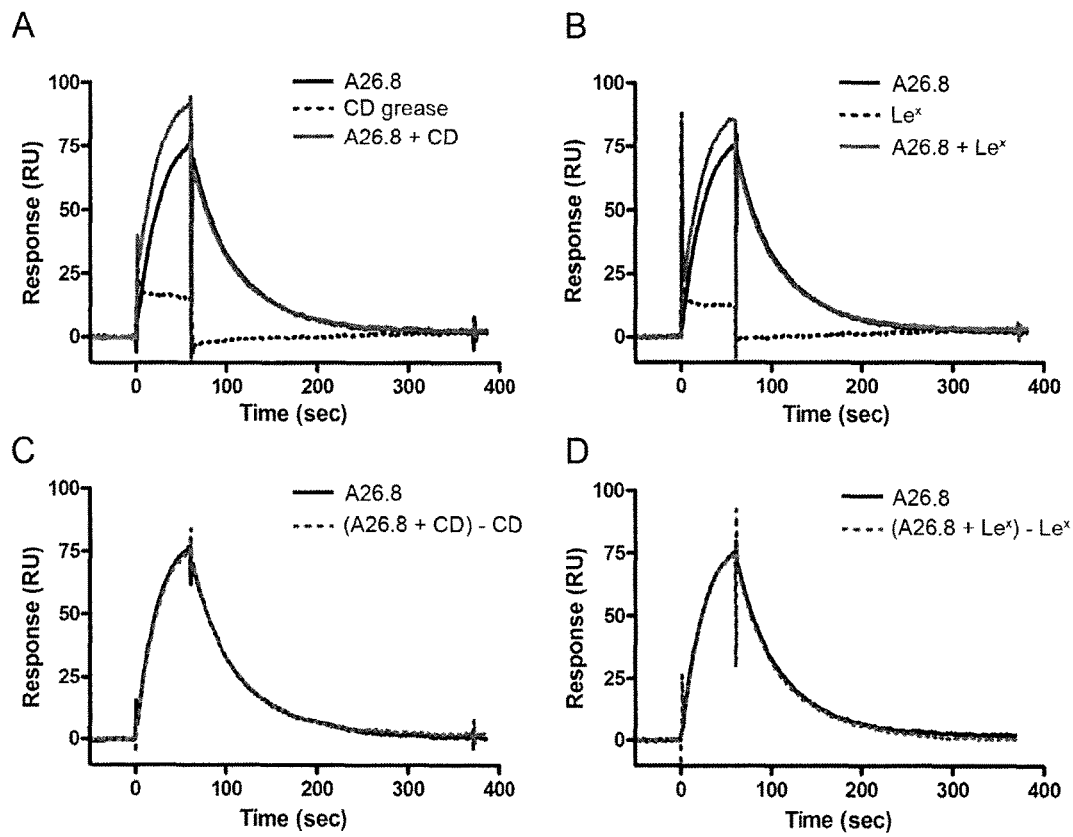
FIG. 12 shows results of Biacore analysis, which revealed that two trisaccharides, CD-grease (CD) and Le$^X$-AmHex (Le$^X$), known to interact at the carbohydrate binding sites of TcdA-RBD, did not inhibit V$_H$H binding to immobilized TcdA. All four neutralizing V$_H$Hs were tested and one representative example is shown.
Figure 13:
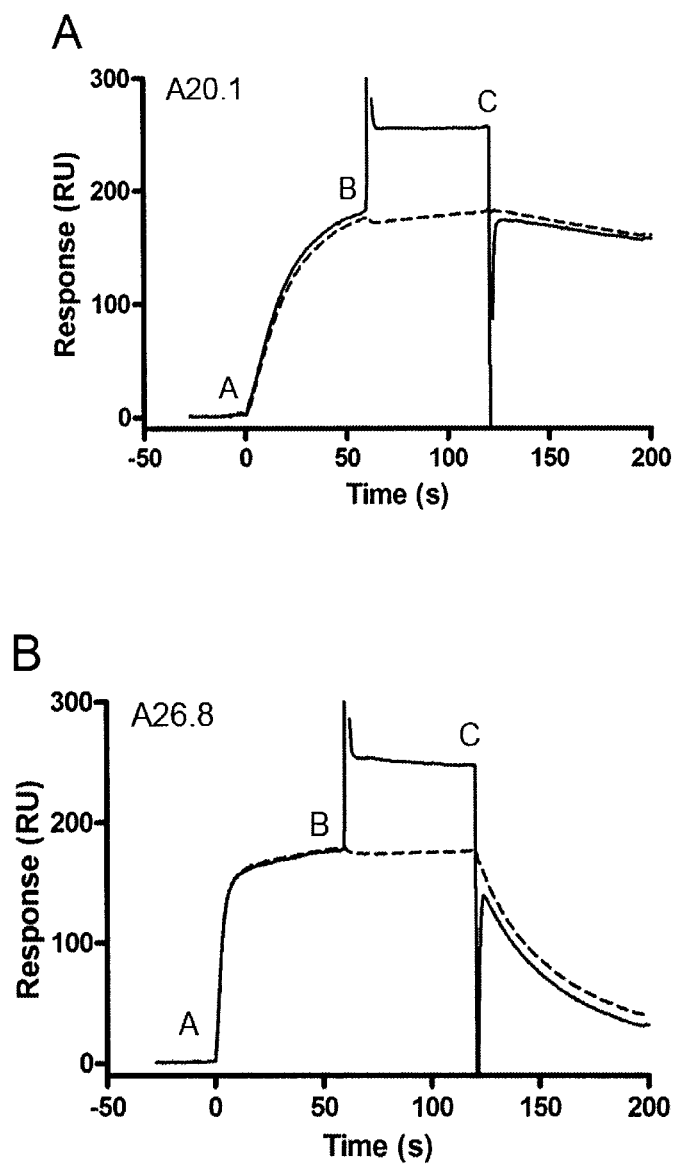
FIG. 13 shows Biacore results indicating V$_H$H binding to TcdA does not impair binding of the trisaccharide CD-grease (CD), which is known to bind TcdA-RBD.

Using BIACORE SPR, inhibition of the V$_H$H-TcdA interaction with two trisaccharides known to bind TcdA-RBD was also attempted, in order to gain insight into the TcdA epitope recognized by the V$_H$Hs. CD-grease ($\alpha$-Gal-(1,3)-$\beta$-Gal-(1,4)-$\beta$-GlcNAcO(CH$_2$)$_8$CO$_2$CH$_3$; Greco et al, 2006) and Le$^x$-AmHex (Gal-$\beta$1,4-(Fuc-$\alpha$1,3)-GlcNAc-(CH$_2$)$_6$—NH$_2$—HOAc; P. Zhang and C. C. Ling, unpublished) are known to interact with the carbohydrate binding pockets of TcdA-RBD (Greco et al, 2006). Briefly, 4 V$_H$Hs (i.e., A4.2, A5.1, A20.1 and A26.8) at K$_D$ concentrations were injected alone or in the presence of trisaccharide (2 mM) over immobilized TcdA (~8000 RUs). The response obtained from the interaction of trisaccharide with TcdA was subtracted from response generated by V$_H$H+trisaccharide co-injection experiments. Then, the response of each V$_H$H to TcdA in the presence of trisaccharide was compared to the response generated by the V$_H$H-TcdA interaction. FIG. 12 shows a representative example in which CD-grease and Le$^x$-AmHex trisaccharides are free to bind TcdA in the presence of A26.8 V$_H$H. We also show in FIG. 13 two examples of CD-grease binding freely to TcdA in the presence of saturating amounts of bound V$_H$Hs A20.1 (FIG. 13A) and A26.8 (FIG. 13B). Collectively, these studies indicate the V$_H$Hs are not binding to TcdA in such a way as to prevent trisaccharide binding. Therefore, the anti-TcdA V$_H$H tested do not bind in the carbohydrate binding pocket, or sufficiently close to it, as they do not inhibit the free trisaccharide from accessing the toxin.

V$_H$Hs have long, flexible CDR3 loop regions that have been shown to form a convex paratope that can extend into clefts or active sites of protein antigens (De Genst et al, 2006). The recently solved crystal structure of TcdA-RBD was shown to contain seven carbohydrate binding pockets thought to be involved in cell receptor binding (Greco et al, 2006). The methods just described were to investigate whether TcdA neutralization was due to V$_H$H binding in the TcdA-RBD carbohydrate-binding pocket. The binding of the neutralizing V$_H$Hs to TcdA was not inhibited in the in co-injection experiments (FIG. 12). Both CD-grease and Le$^x$-AmHex trisaccharides were used at their predicted K$_D$ concentrations and were shown to bind immobilized TcdA by BIACORE SPR, but did not prevent V$_H$H binding to TcdA when the trisaccharide response for TcdA was subtracted from response generated by co-injection experiments (FIG. 12). In additional BIACORE SPR experiments, both of the trisaccharides were found to be free to bind V$_H$H-saturated TcdA (data not shown). Furthermore, V$_H$H binding to TcdA was not inhibited in ELISA with trisaccharide concentrations as high as 10 mM (data not shown). Taken together, these data suggest the present V$_H$Hs do not inhibit free trisaccharides from accessing their binding sites on TcdA-RBD and that the V$_H$Hs are not binding at sites occupied by the trisaccharides.

EXAMPLE 10

Engineering, Expression, and Purification of Mutant V$_H$Hs

The extreme pH and protease-rich environment of the upper gastrointestinal tract is a major obstacle facing orally-administered protein therapeutics, including antibodies. For these reasons, the V$_H$Hs of Example 4 were engineered to improve biophysical properties. The methods used herein are also summarized in Hussack et al (2011).

A panel of *C. difficile* toxin A (TcdA)-specific V$_H$Hs were expressed with an additional disulfide bond by introducing Ala/Gly$^{54}$-Cys$^{54}$ and Ile$^{78}$→Cys$^{78}$ mutations. It was hypothesized that the addition of a disulfide bond in the hydrophobic core of a V$_H$H antibody fragments between framework 2 (FR2) and FR3 would not only increase thermal stability at neutral pH, as previously reported (Hagihara et al, 2007; Saerens et al, 2008), but would also impart resistance to proteolytic degradation and increase antibody stability at low pH. The sequences of the mutant V$_H$Hs are shown in FIG. 14.

To construct mutant V$_H$Hs with a second internal disulfide bond, splice-overlap extension (SOE) PCR was performed essentially as described (Ho et al, 1989; Arbabi et al, 2010) using 4 primers for each V$_H$H and two rounds of PCR. Nucleotides encoding amino acid residues at positions 54 and 78 (IMGT numbering system) were changed to Cys-coding nucleotides through primer-forced mutation. In the first PCR, two mutagenized overlapping sub-fragments were generated for each V$_H$H. The primer pairs used for each V$_H$H were as follows: A4.2m (BbsI-VHH and A4.2mR-Cys, A4.2mF-Cys and BamHI-VHH); A5.1m (BbsI-VHH and A5.1mRCys, A4.2mR-Cys and BamHI-VHH); A19.2m (BbsI-VHH and A19.2mR-Cys, A19.2mF-Cys and BamHI-VHH); A20.1m (A20.1 mSfiI-F and A20.1mR-Cys, A20.1mF-Cys and A20.1 mSfiI-R); A24.1m (A20.1 mSfiI-F and A24.1mR-Cys, A24.1mF-Cys and A20.1 mSfiI-R); A26.8m (BbsI-VHH and A26.8mR-Cys, A26.8mF-Cys and BamHI-VHH). Each sub-fragment was gel purified and spliced with its partner fragment in a second PCR. Briefly, 160 ng of each sub-fragment were added to a 50 μl PCR mixture containing Pfu DNA polymerase, dNTPs and reaction buffer. The reaction was placed in a thermal cycler and the two fragments were spliced together using a program consisting of a preheating step at 94° C. for 5 min and 10 cycles of 94° C. for 30 s, 55° C. for 30 s, and 72° C. for 1 min. To amplify the spliced products, the reaction was heated to 94° C. for 3 min, 5 pmol (0.5 μl) of each primer pair was added (BbsI-VHH and BamHI-VHH for A4.2m, A5.1m, A19.2m, and A26.8m; A20.1 mSfiI-F and A20.1 mSfiI-R for A20.1m and A24.1m), and 35 PCR cycles were performed exactly as described above. The resulting fragments were gel purified, digested with BbsI and BamHI (A4.2m, A5.1m, A19.2m, and A26.8) or SfiI (A20.1m and A24.1m) restriction enzymes and ligated into similarly digested expression vectors (pSJF2H or pMED2). All mutant $V_H$Hs were expressed in the same vectors as their counterpart wild-type $V_H$Hs (see Example 4). For cloning into pSJF2H, mutant $V_H$H DNA were amplified with primers containing 5' BbsI and 3' BamHI restriction sites while cloning into pMED2 required amplification with primers containing both 5' and 3' SfiI restriction sites. The vectors were transformed into TG1 *E. coli* for $V_H$H expression. Positive colonies were identified by colony-PCR and DNA sequencing, using the M13RP and M13FP primers.

TABLE 2

Primers used for construction of disulfide mutant $V_H$Hs. [a]Reverse and forward primers for construction of A4.2m, A5.1m, A19.2m, and A26.8m.

| Primers | Sequence (5' → 3') | Purpose |
| --- | --- | --- |
| M13FP | GTA AAA CGA CGG CCA GT (SEQ ID NO: 66) | Screening |
| M13RP | CAG GAA ACA GCT ATG AC (SEQ ID NO: 67) | Screening |
| BbsI-VHH[a] | TAT GAA GAC ACC AGG CCC AGG TAA AGC TGG AGG AGT CT (SEQ ID NO: 63) | Constructing mutants |
| BamHI-VHH[a] | TTG TTC GGA TCC TGA GGA GAC GGT GAC CTG (SEQ ID NO: 65) | Constructing mutants |
| A4.2mR-Cys | AGT CTG CAT AGT ATG TGC TAC CAC CAC TCC GGC TAA CAG CGC AAA CAA ACT C (SEQ ID NO: 68) | Constructing A4.2m |
| A4.2mF-Cys | TAG CAC ATA CTA TGC AGA CTC CGT GAA GGG CCG ATT CAC CTG CTC CAG AGA C (SEQ ID NO: 69) | Constructing 4.2m/A5.1m |
| A5.1mR-Cys | AGT CTG CAT AGT ATG TGC TAC TAC CAT TCC GGG TAA TAA CGC ATA CAA ACT C (SEQ ID NO: 70) | Constructing A5.1 m |
| A19.2mR-Cys | ACT CTA CAT AGG CAC TAT TAC CAC CAC GCC GGC TAA TAC CGC ATA CAA ACT C (SEQ ID NO: 71) | Constructing A19.2m |
| A19.2mF-Cys | TAA TAG TGC CTA TGT AGA GTC CGT GAA GGG CCG ATT CAC CTG CTC CAG AGA C (SEQ ID NO: 72) | Constructing A19.2m |
| A20.1mSfiI-F | ACC GTT GCG CAG GCC CAG CCG GCC ATG GCC CAG GTA CAG C (SEQ ID NO: 73) | Constructing A20.1m/A24.1m |
| A20.1mR-Cys | TGT CTG CAT AGT ATG TGG TCC GCC CCG TAG AAC TCC CCG CGC ATA CAA ACT C (SEQ ID NO: 74) | Constructing A20.1m |
| A20.1mF-Cys | GAC CAC ATA CTA TGC AGA CAG CGT GAA GGG CCG ATT CAC CTG CTC CAG AGA C (SEQ ID NO: 75) | Constructing A20.1m |
| A20.1mSfiI-R | GTT CGG ATC CCT GGC CGG CCT GGC CTG AGG AGA CGG TGA CC (SEQ ID NO: 76) | Constructing A20.1m/A24.1m |
| A24.1mR-Cys | AGT CTG CAT AGC GTG TGC TAC CTC CAC CCC AGC TAA TAC CGC ATA CAA ACT C (SEQ ID NO: 77) | Constructing A24.1m |
| 424.1mF-Cys | TAG CAC ACG CTA TGC AGA CTC CGT GAA GGG CCG ATT CAC CTG CTC CAG AGA C (SEQ ID NO: 78) | Constructing A24.1m |
| A26.8mR-Cys | AGT CTG CAT AGT ATG TGC TCG TAC CAG TCG AGC TAA TAA CGC ATA CAA ACT C (SEQ ID NO: 79) | Constructing A26.8m |
| A26.8mF-Cys | GAG CAC ATA CTA TGC AGA CTC GGT GAA GGG CCG GTT CAC CTG CTC CAG AGA C (SEQ ID NO: 80) | Constructing A26.8m |

Figure 15:
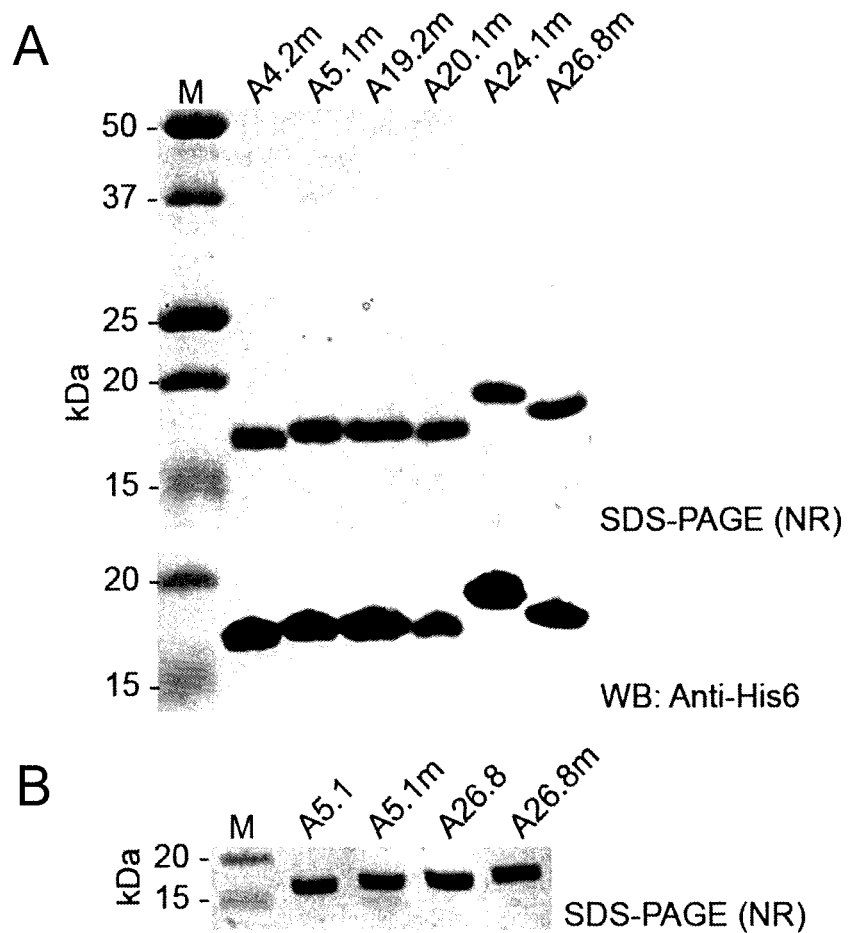
FIG. 15A shows a non-reducing (NR) SDS-PAGE analysis and Western blot (WB) probed with an anti-His₆ IgG on IMAC-purified mutant $V_HH$s. M: molecular weight marker in kDa.
FIG. 15B is a representative SDS-PAGE analysis showing mutant $V_HH$s run slower than the corresponding wild-type $V_HH$s under non-reducing conditions.

Expression and purification of mutant $V_H$Hs was performed as described in Example 4, followed by dialysis into phosphate-buffered saline pH 7.3 (PBS), into distilled, deionized water (ddH$_2$O) for mass spectrometry (MS) analysis, or into 10 mM phosphate buffer pH 7.3 for CD experiments. Soluble mutant $V_H$Hs were extracted from the periplasm of TG1 *E. coli* and purified by immobilized-metal affinity chromatography (IMAC) with purified yields ranging from 3-12 mg/l of bacterial culture. Non-reducing SDS-PAGE and Western blot analysis of the purified products revealed the mutant $V_H$Hs were of high purity and did not form interdomain disulfide bonds (FIG. 15A). On non-reducing SDS-PAGE gels, mutant $V_H$Hs consistently ran slower than their corresponding wild-type $V_H$Hs (FIG. 15B).

Formation of the non-canonical disulfide linkages was confirmed by mass spectrometry analysis on cyanogen bromide+trypsin digested mutant $V_H$Hs by identifying peptides containing the introduced disulfide bond. Briefly, 100 μl reactions containing 50 μg of mutant V$_H$H (diluted in PBS), 10 μl of 1 M HCl and 40 μL of CNBr (10 mg/ml stock prepared in 1 M HCl) were digested for 14 h at ambient temperature in the dark. The next day, 100 μl of 1 M Tris-HCl, pH 8.6, and 60 μl of trypsin (100 μg/ml stock; sequencing grade, Roche, Mississauga, ON, Canada) were added directly to the CNBr reaction mixture and incubated for 2 h at 37° C. Samples were then analyzed by non-reducing SDS-PAGE to ensure digestion prior to MS analysis. An aliquot of the proteolytic digest of each V$_H$H was re-suspended in 0.1% formic acid (aq) and analyzed by nano-flow reversed-phase HPLC mass spectrometry (nanoRPLC-ESI-MS) using a nanoAcquity UPLC system coupled to a Q-TOF ULTIMA hybrid quadrupole/TOF mass spectrometer (Waters, Milford, Mass.) with data dependent analysis (DDA). The peptides were first loaded onto a 180 μm I.D.×20 mm 5 μm SYMMETRY C18 trap (Waters), then eluted to a 100 μm I.D.×10 cm 1.7μm BEH130C18 column (Waters) using a linear gradient from 0% to 36% solvent B (ACN+0.1% formic acid) in 36 min, 36%-90% solvent B for 2 min. Solvent A was 0.1% formic acid in water. The peptide MS$^2$ spectra were searched against the V$_H$H protein sequences using the MASCOT database searching algorithm (Matrix Science, London, UK). The MS$^2$ spectra of the disulphide-linked peptides were deconvoluted using the MaxEnt 3 program (Waters) for de-novo sequencing.

Figure 16A:
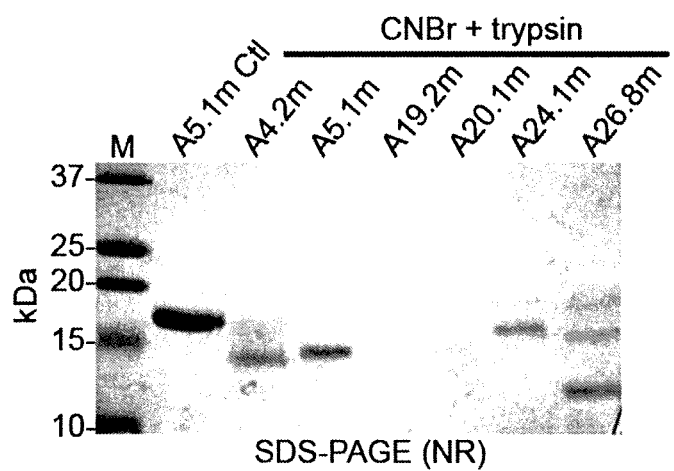
FIG. 16A shows a SDS-PAGE gel under non-reducing (NR) conditions of $V_HH$s (3 µg per lane), which illustrates near-complete digestion with CNBr and trypsin. Untreated A5.1m was added as a control (Ctl). M: molecular weight marker in kDa.
Figure 16B:
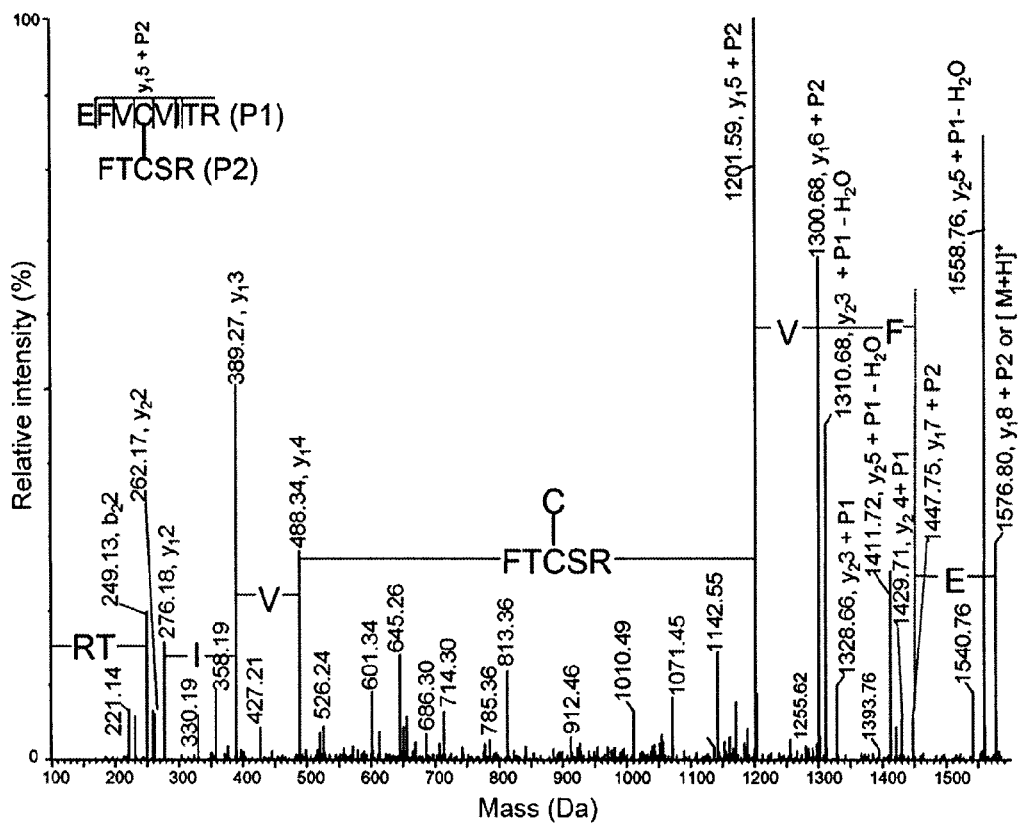
FIG. 16B shows a MaxEnt 3 deconvoluted CID-MS² spectrum of the m/z 526.25 (3+) ion of the disulfide-linked peptide EFVCVITR (P1)-FTCSR (P2), encompassing the Cys⁵⁴-Cys⁷⁸ disulfide bond, from CNBr/trypsin digested A5.1m. Amino acid positions are based on the IMGT numbering system.

To precisely confirm the presence of the introduced disulfide bond, mutant V$_H$Hs were digested with CNBr and trypsin (FIG. 16A) and their digests subjected to MS$^2$ analysis. The identification coverage of the mutant V$_H$Hs from the analysis of their CNBr/trypsin digests using nanoRPLC-ESI-MS with DDA was more than 30%. The disulfide-linked peptide ions appeared prominent in the survey scan of the DDA experiment when the proteins were digested with a combination of CNBr and trypsin. Peptide fragments linked by the engineered Cys$^{54}$-Cys$^{78}$ disulfide bond (shown in bold text in FIG. 14) were positively identified for all mutant V$_H$Hs by manual de-novo sequencing (Table 3). For example, the protein sequence coverage of A5.1m was 43% and a prominent ion at m/z 526.25 (3+) was sequenced as a disulfide-linked peptide EFVCVITR (P1) and FTCSR (P2) as shown (FIG. 16B, FIG. 14, Table 3). An almost complete disulfide-linked y fragment ion series was observed from one peptide with the other peptide attached as a modification via a disulfide bond, which remains intact under collision induced dissociation (CID) [59].

TABLE 3

Disulfide linkage determination of mutant V$_H$Hs by MS$^2$ analysis. Mutant V$_H$Hs were digested with CNBr and trypsin and the peptides analyzed by MS$^2$. The peptides containing the Cys$^{54}$-Cys$^{78}$ disulfide linkage are shown with connecting cysteines bolded. A nearly perfect match between MW$_{for}$ and MW$_{exp}$ equates to the presence of the Cys$^{54}$-Cys$^{78}$ disulfide linkage.

| V$_H$H | CNBr/tryptic peptides | | MW$_{for}$ | MW$_{exp}$ | ΔMW |
|---|---|---|---|---|---|
| A4.2m | EFVCAVSR (SEQ ID NO: 81 and 87) | FTCSR | 1519.69 | 1519.70 | −0.01 |
| A5.1m | EFVCVITR (SEQ ID NO: 82 and 87) | FTCSR | 1575.75 | 1575.76 | −0.01 |
| A19.2m | EFVCGISR (SEQ ID NO: 83 and 87) | FTCSR | 1519.69 | 1519.64 | 0.05 |
| A20.1m | EFVCAGSSTGR (SEQ ID NO: 84 and 87) | FTCSR | 1722.74 | 1722.84 | −0.10 |
| A24.1m | EFVCGISWGGGSTR (SEQ ID NO: 85 and 87) | FTCSR | 2064.91 | 2064.98 | −0.07 |
| A26.8m | EFVCVISSTGTSTYYADSVK (SEQ ID NO: 86 and 87) | FTCSR | 2766.25 | 2766.33 | −0.08 |

MW$_{for}$: formula (expected) molecular weight (Da);
MW$_{exp}$: experimental molecular weight (Da);
ΔMW = MW$_{for}$ − MW$_{exp}$.

EXAMPLE 11

Size Exclusion Chromatography and Affinity Measurements of Wild-Type and Mutant V$_H$Hs Wild-type and mutant V$_H$Hs were passed over a SUPERDEX 75 (GE Healthcare) size exclusion chromatography column as described in Example 7 to determine their aggregation state. Both wild-type and mutant V$_H$Hs were determined to be non-aggregating monomers (FIGS. 5, 17A). Similar size exclusion profiles were obtained for mutant and wild-type, indicating the second disulfide bond does not promote the formation of interdomain disulfide-bonds or multimeric mutant V$_H$Hs. The elution volumes (V$_e$s) of SEC molecular weight standards are shown with arrows in FIG. 17A and are aligned relative to the A4.2 and A4.2m chromatograms. a: ovalbumin (MW=43.0 kDa, V$_e$=8.90 ml); b: carbonic anhydrase (MW=30.0 kDa, V$_e$=9.71 ml); c: typsin inhibitor (MW=20.1 kDa, V$_e$=11.06 ml); d: α-lactalbumin (MW=14.4 kDa, V$_e$=11.97 ml); e: vitamin B (MW=1.3 kDa, V$_e$=18.7 ml). The equation of the line of a standard curve generated from these standards was LOG$_{10}$ MW=−0.1539V$_e$+2.9949 (r$^2$=0.9995). From this equation the V$_H$H apparent MWs ranged from 9.8-13.6 kDa, indicating monomeric V$_H$Hs.

All kinetic rate and equilibrium constants of the mutants were determined as described (Example 7) using a BIACORE 3000 instrument from GE Healthcare and 10,287 RUs of immobilized TcdA. SPR analysis revealed the specific and high-affinity binding of 4 of 6 mutant V$_H$Hs to TcdA (FIG. 17B, Table 4). These four were also the strongest neutralizers (see Example 14). Two mutants (A19.2m and A24.1m) exhibited non-specific binding to reference cell proteins and as a result specific interaction data could not be generated, even at antibody concentrations as high as 3.2 μM. When compared to their wild-type counterparts, the K$_D$s of 3 TcdA-binding mutants were reduced approximately 2-6 fold (Table 4), while the affinity of one V$_H$H was relatively unchanged (K$_D$s of 24 nM and 20 nM for A4.2 and A4.2m, respectively). The K$_D$ reductions were largely a result of faster $k_{off}$ values and to a much lesser extent influenced by slower $k_{on}$ values. Without wishing to be bound by theory, the $Cys^{54}$-$Cys^{78}$ disulfide bond may slightly distort the $V_H$H structure leading to decreases in target binding affinities and decreases in antibody specificity.

TABLE 4

Kinetic and affinity constants of wild-type and mutant $V_H$Hs binding to TcdA.

| $V_H$H | Wild-type | | | Mutant | | | Fold change in |
|---|---|---|---|---|---|---|---|
| | $k_{on}$ (M$^{-1}$s$^{-1}$) | $k_{off}$ (s$^{-1}$) | $K_D$ (nM) | $k_{on}$ (M$^{-1}$s$^{-1}$) | $k_{off}$ (s$^{-1}$) | $K_D$ (nM) | $K_D{}^a$ |
| A4.2/A4.2m | 6.7 × 10$^5$ | 1.6 × 10$^{-2}$ | 24 | 9.3 × 10$^5$ | 1.9 × 10$^{-2}$ | 20 | −1.2 |
| A5.1/A5.1m | 1.6 × 10$^6$ | 5.0 × 10$^{-3}$ | 3 | 9.5 × 10$^5$ | 1.6 × 10$^{-2}$ | 17 | +5.7 |
| A19.2/A19.2m | 1.4 × 10$^4$ | 3.9 × 10$^{-3}$ | 290 | — | — | — | |
| A20.1/A20.1m | 8.2 × 10$^5$ | 1.6 × 10$^{-3}$ | 2 | 6.4 × 10$^5$ | 5.9 × 10$^{-3}$ | 9.2 | +4.6 |
| A24.1/A24.1m | 6.0 × 10$^4$ | 1.6 × 10$^{-2}$ | 260 | — | — | — | |
| A26.8/A26.8m | 1.4 × 10$^6$ | 1.6 × 10$^{-2}$ | 12 | 1.0 × 10$^6$ | 2.8 × 10$^{-2}$ | 28 | +2.3 |

NB: no binding detected by Biacore, at $V_H$H concentrations as high as 3.2 µM.
$^a$Relative to wild-type $V_H$H.

EXAMPLE 12

Circular Dichroism Analysis of Mutant and Wild-type $V_H$Hs

Circular dichroism (CD) experiments were used to examine $V_H$H secondary structure, tertiary structure, thermal refolding efficiency, and thermal stability at both neutral and acidic pH.

Wild-type and mutant $V_H$Hs were analyzed by circular dichroism spectrophotometry using a Jasco J-815 Spectrophotometer (Jasco, Easton, Md.) at pH 7.3 in 10 mM phosphate buffer (PB; 1.4 g/ml Na$_2$HPO$_4$+0.24 g/ml KH$_2$PO$_4$) and at pH 2.0 (10 mM PB+50 mM HCl). For all CD experiments performed at pH 2.0, proteins were equilibrated in the above buffer for a minimum of 2 h before scanning. For far-UV CD secondary structure scans, thermal refolding, and thermal unfolding experiments, a 5 mm cuvette containing 1.5 ml of $V_H$H at 50 µg/ml (3.2 µM; $A_{280}$≅0.1) was used. In these experiments, data were collected for each sample between 190-260 nm with a 1 mm bandwidth, 20 nm/min scan speed and 0.5 nm data pitch. Raw data was smoothed using the Jasco software, exported and converted to mean residue ellipticity, [θ]. Thermal unfolding was followed at 215 nm by far-UV CD, with CD measurements taken every 2° C. from 30° C. to 96° C. with a temperature increase of 1° C./min. Mean residue ellipticities [θ] were used to calculate the fraction of protein folded (FF) which is shown in Equation 1, $$FF=([\theta]-[\theta_U])/([\theta_F]-[\theta_U]) \quad \text{Equation 1}$$

where [θ$_F$] and [θ$_U$] are the molar ellipticities of the folded (30° C.) and unfolded (96° C.) states, respectively. The thermal unfolding midpoint temperature (T$_m$) was obtained by plotting FF against temperature and performing sigmoidal Boltzmann curve fitting in GraphPad Prism (GraphPad Software, Inc., La Jolla, Calif.). For refolding experiments, $V_H$Hs were first scanned (190 nm-260 nm) at 25° C. (folded); heated at 96° C. for 20 min and scanned (unfolded); and equilibrated to 25° C. for 3 h before a third scan (refolded). Raw data was converted as before and thermal refolding efficiencies (TRE) were calculated at 215 nm using Equation 2, $$TRE=(([\theta_U]-[\theta_R])/([\theta_U]-[\theta_F]))\times 100 \quad \text{Equation 2}$$

where [θ$_F$] is the molar ellipticity of the folded state acquired at 25° C., [θ$_U$] is the molar ellipticity of the unfolded state acquired at 96° C., and [θ$_R$] is the molar ellipticity of the refolded state acquired at 25° C. To compare the tertiary structures of wild-type and mutant $V_H$Hs at neutral and acidic pH, near-UV CD experiments were performed in the range of 250 nm-340 nm using the conditions described above with the exception that a 10 mm cuvette containing 2 ml of protein at 250 µg/ml was used. In all cases, the ellipticity of buffer blanks were subtracted from experimental values and the reported data is the average of two independent experiments with 4 data accumulations in each.

Figure 18:
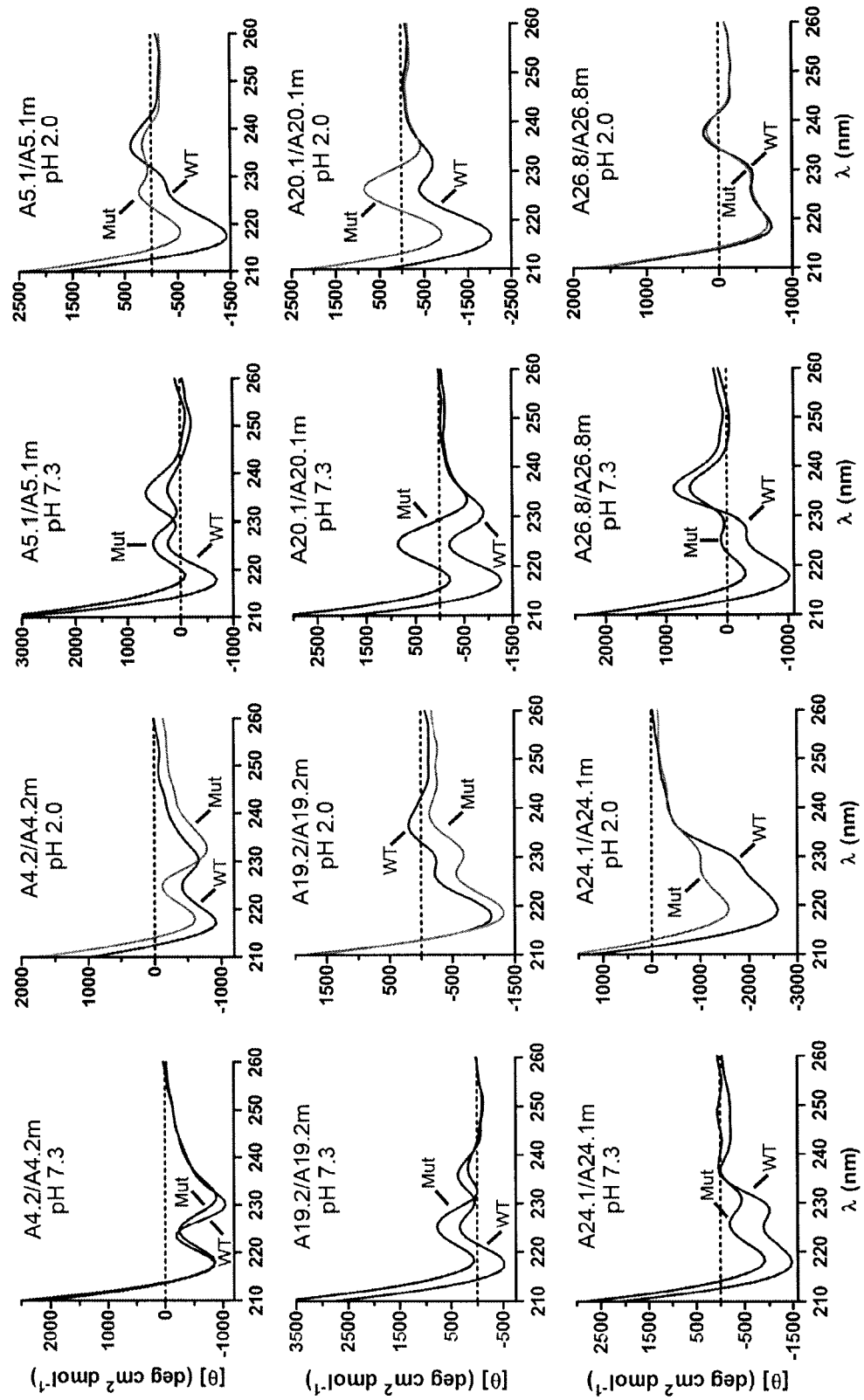
FIG. 18 shows far-UV CD spectra of $V_HH$s at neutral and acidic pH. CD scans (210 nm-260 nm) were performed at 25° C. on $V_HH$s (50 µg/mL) equilibrated for 2 h in 10 mM phosphate buffer (pH 7.3) or 10 mM phosphate buffer+50 mM HCl (pH 2.0). The spectra represent the mean residue ellipticity of 8 data accumulations collected from 2 independent experiments. Black lines: wild-type $V_HH$; grey lines: mutant $V_HH$.

Far-UV CD examined the $V_H$H secondary structure, and results are shown in FIG. 18. Although the overall shape of the far-UV CD spectra from wild-type and mutant $V_H$H pairs was similar at a given pH, spectra intensity shifts were observed for all wild-type/mutant pairs. In general, peak minima were seen at 216 nm-218 nm and at 230 nm-235 nm wavelengths but, in almost all cases, the intensity of the peak at 216 nm-218 nm was lower (decreased negative ellipticity) for mutant $V_H$Hs. Another prominent feature in the far-UV CD spectra was that mutant $V_H$Hs exhibited a near-UV shift in the peak range of 230 nm-235 nm. Wild-type $V_H$Hs possessed peak minima around 230 nm-232 nm whereas mutants displayed peak minima in this region around 232 nm-235 nm. Interestingly, A4.2/A4.2m, which had the most similar CD spectra at neutral pH of all the wild-type/mutant pairs, also had the same binding affinity for TcdA.

Figure 19:
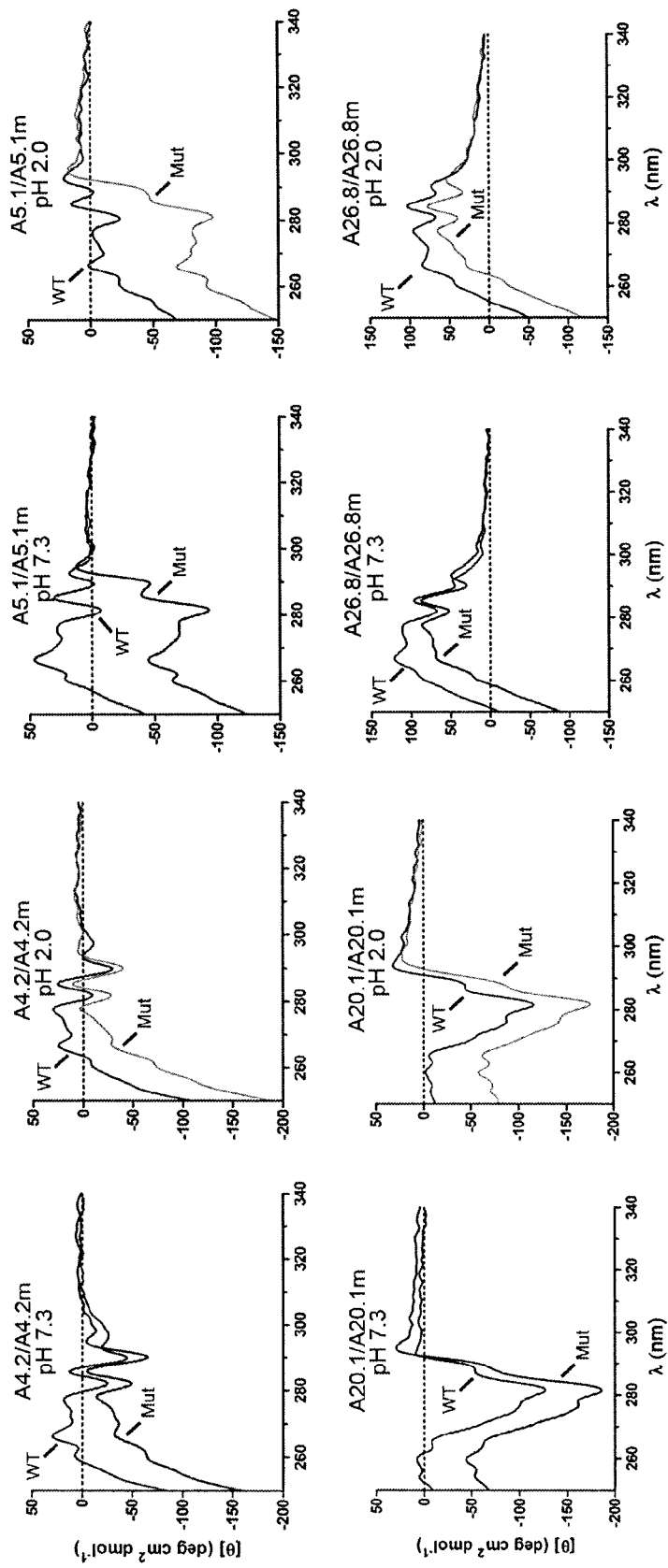
FIG. 19 shows near-UV CD analysis of $V_HH$s at neutral and acidic pH. CD scans (250 nm-340 nm) were performed at 25° C. on $V_HH$s (250 µg/mL) equilibrated for 2 h in 10 mM phosphate buffer (pH 7.3) or 10 mM phosphate buffer+50 mM HCl (pH 2.0). The spectra represent the mean residue ellipticity from 8 data accumulations collected from 2 independent experiments. Black lines: wild-type $V_HH$; grey lines: mutant $V_HH$.

$V_H$H tertiary structures were analyzed with near-UV CD spectroscopy, and results are shown in FIG. 19. Overall, the near-UV spectra profiles were similar between wild-type and mutant $V_H$H pairs. Spectra from wild-type and mutant pairs shared nearly identical peak wavelengths; however, between 250 nm to 295 nm, the ellipticity of mutant $V_H$Hs was consistently more negative than wild-type $V_H$Hs. There were also subtle differences in peaks occurring around 297 nm, with mutant $V_H$Hs exhibiting a minor but consistent shift to the right. Three of the four wild-type/mutant pairs (A4.2/A4.2m, A5.1/A5.1m, and A20.1m/A20.1m) produced predominantly negative ellipticity, whereas the A26.8/A26.8m pair remained positive. The contributions of the second disulfide bond cannot be ruled out as a factor which may augment the contribution of aromatic residues to ellipticity (increasing negatively) of the mutants.

Thermal refolding efficiencies (TREs) of wild-type and mutant $V_H$Hs at neutral and acid pH were also determined by far-UV CD. CD scans were performed at 50 µg/ml concentrations of $V_H$Hs (3.1 µM) at 25° C. (folded), after heating to 96° C. (unfolded), and after cooling for 3 h to 25°

Figure 20:
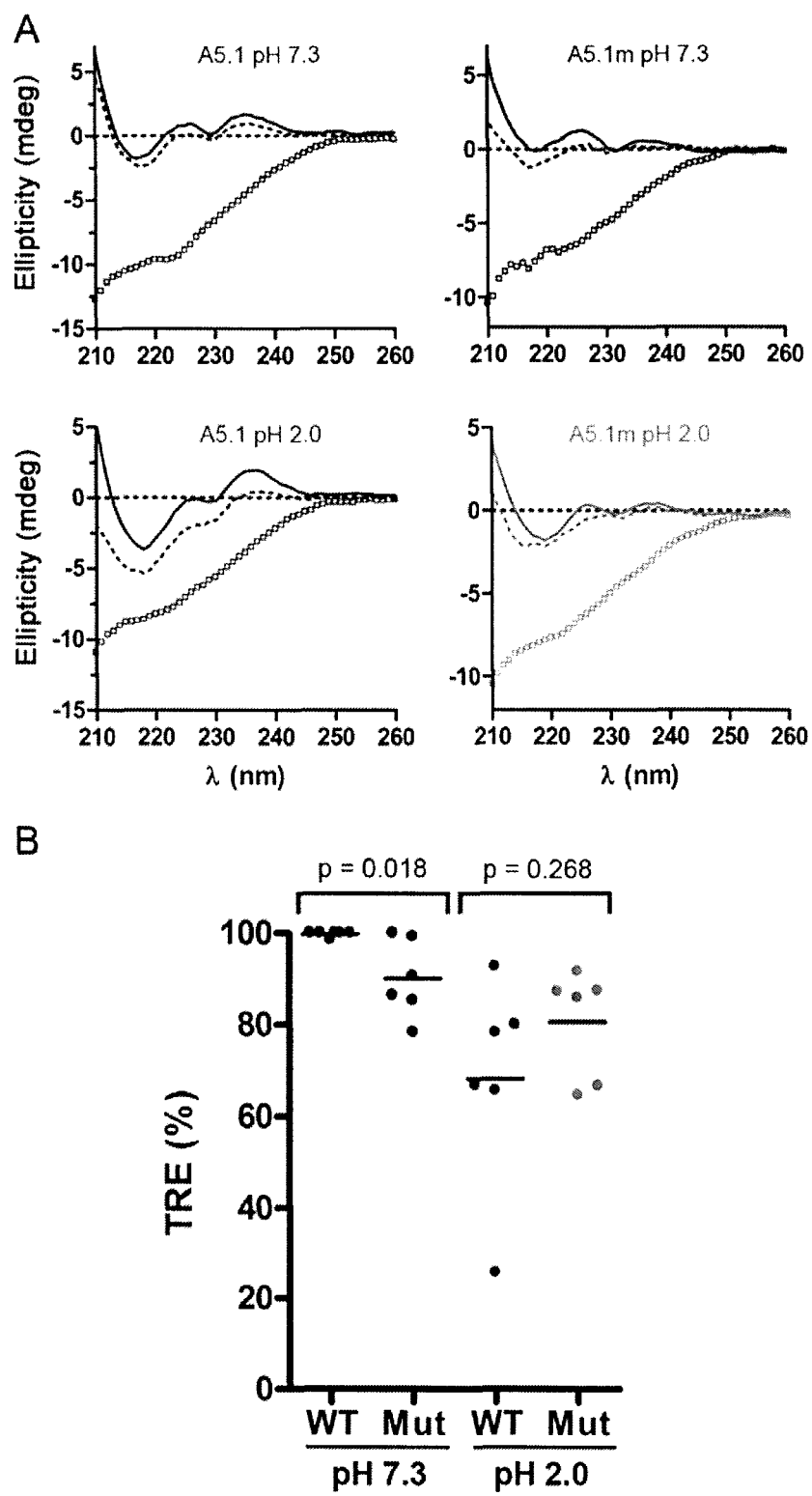
FIG. 20 shows far-UV CD scans used to determine $V_HH$ refolding efficiencies under neutral and acidic pH conditions. A5.1 is shown as a representative example.

C. (refolded). Thermal refolding efficiencies were determined as the extent to which the CD spectrum of the heated-and-cooled $V_HH$ approached that of the folded form. At pH 7.3, the TRE of wild-type $V_H$Hs was essentially 100% and significantly higher than for the mutants (FIG. 20, p=0.018, unpaired two-tailed t-test). Specifically, wild-type $V_H$Hs possessed a mean TRE of 99.7%±0.2% compared to mutant $V_H$Hs with a mean TRE of 90.0%±3.4% (FIG. 20). The ability of $V_H$Hs to refold in acidic conditions was also examined and, in general, mutants showed higher TREs at pH 2.0 (FIG. 20, Table 5). The mean TRE of wild-type $V_H$Hs in acid was 68.2%±9.4% compared to 80.6%±4.8% for mutant TREs in acid (FIG. 20). However, the mutant TREs were not significantly higher (p=0.268, unpaired two-tailed t-test). It should be noted that the TRE of 5 of 6 mutant $V_H$Hs increased in acidic conditions, with the TRE of A26.8m reaching 64.7% compared to only 25.8% for A26.8.

TABLE 5

Thermal refolding efficiencies (TREs) of wild-type and mutant $V_H$Hs at pH 2.0. TRE (%) ± SEM (n = 8).

| $V_HH$ | TRE (%) | $V_HH$ | TRE (%) |
|---|---|---|---|
| A4.2 | 80.0 ± 3.8 | A4.2m | 87.4 ± 1.6 |
| A5.1 | 66.9 ± 4.2 | A5.1m | 87.2 ± 3.1 |
| A19.2 | 78.3 ± 4.9 | A19.2m | 91.6 ± 1.4 |
| A20.1 | 65.7 ± 2.5 | A20.1m | 85.9 ± 2.2 |
| A24.1 | 92.7 ± 0.6 | A24.1m | 66.7 ± 0.3 |
| A26.8 | 25.8 ± 17.6 | A26.8m | 64.7 ± 2.2 |

Figure 21A:
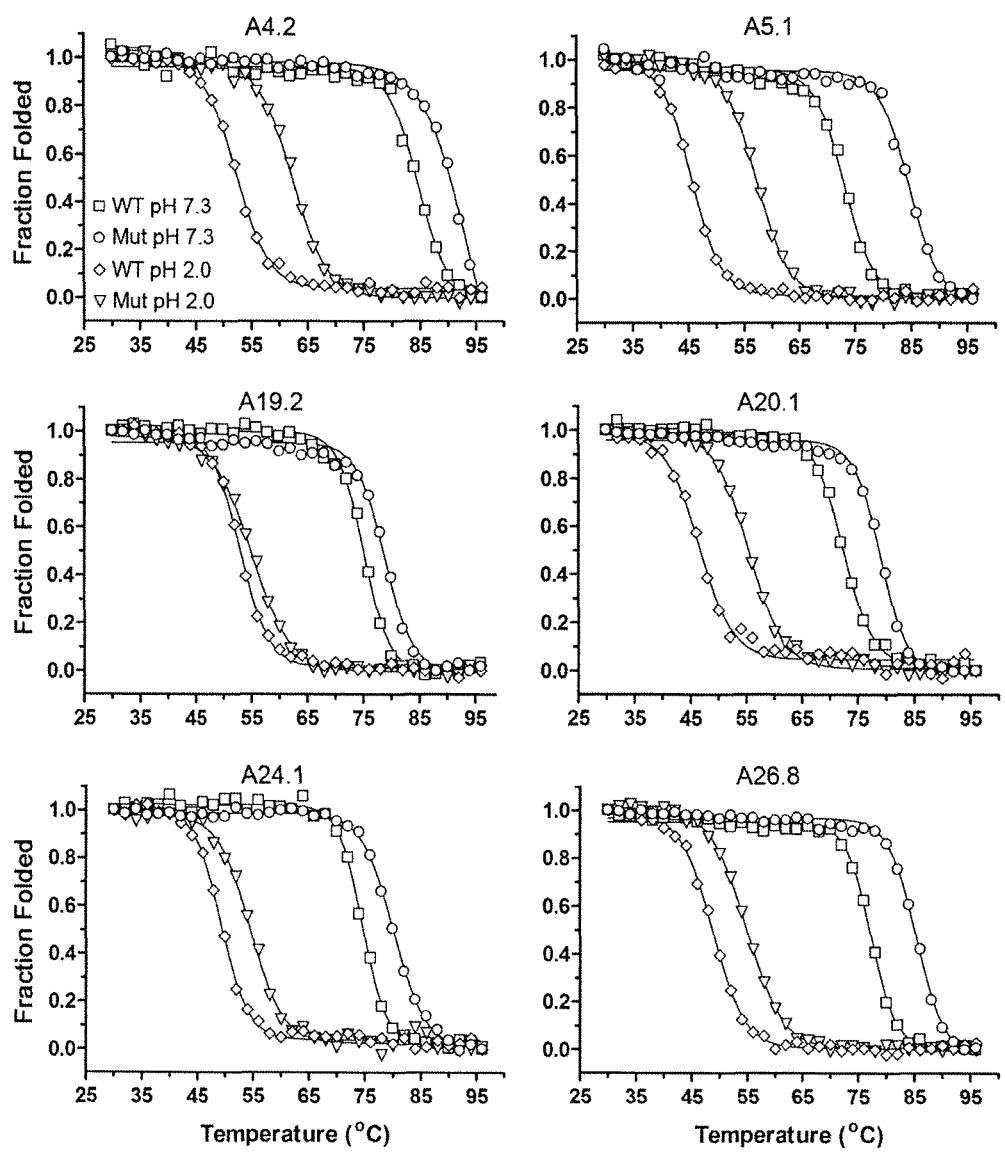
FIG. 21A shows unfolding transition curves for all six WT and mutant anti-TcdA $V_HH$s at neutral pH (7.3) and acidic pH (2). $V_HH$ thermal unfolding midpoint temperatures ($T_m$s) were determined using CD spectroscopy by following antibody unfolding (50 µg/mL) at 215 nm in 10 mM phosphate buffer+/−50 mM HCl. $T_m$ was determined for each curve by Boltzmann non-linear curve fitting analysis in GraphPad Prism. The goodness of curve fit ($r^2$) ranged from 0.9901-0.9995. In the case of $V_HH$s with few lower baseline data points the $T_m$ is a minimal estimate.
Figure 21:
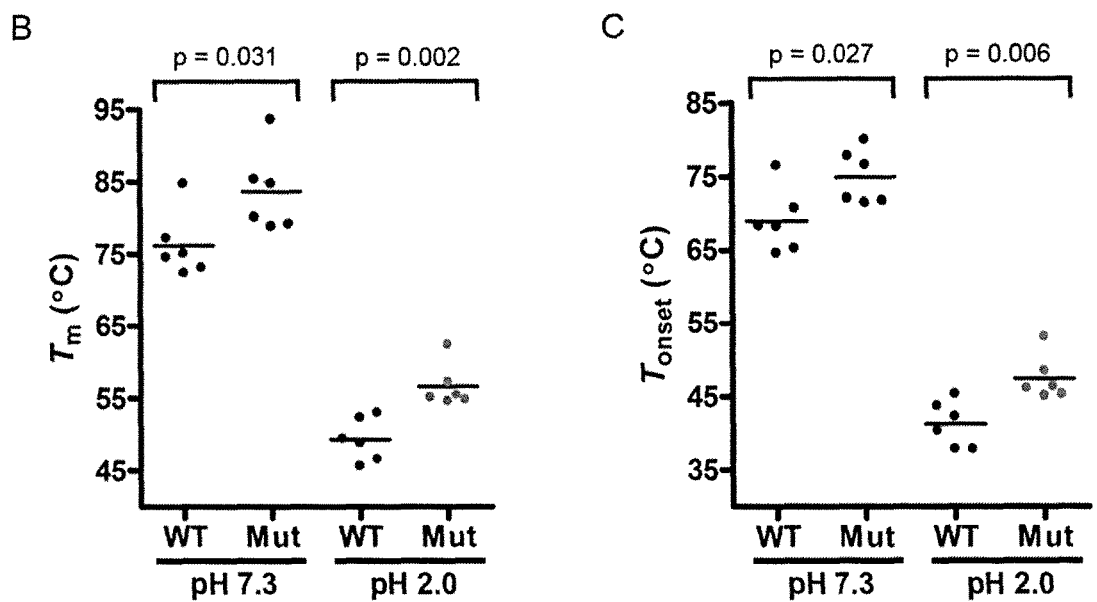
FIG. 21 shows results of circular dichroism analysis for the determination of WT and mutant $V_HH$ melting temperatures at neutral and acidic pH.

Temperature-induced unfolding experiments were conducted in order to determine $V_HH$ $T_m$s and $T_{onset}$s by following changes in $V_HH$ ellipticity at 215 nm (FIG. 21; Tables 6, 7). All $V_H$Hs exhibited sigmoidal melting curves. The wild-type $V_H$Hs have high $T_m$s (as high as 84.7° C.)—significantly higher than those reported for other $V_H$Hs [60]. For all six $V_H$Hs, the mutants possessed higher $T_m$ values, at both neutral and acidic pH (FIG. 21 and Table 6). At neutral pH, the $T_m$ values of mutants ranged from 78.8° C. to 93.6° C., with one mutant, A5.1m, having a $T_m$ 11.6° C. higher than wild-type (A5.1). The increase in mutant $V_HH$ $T_m$s relative to wild-type ranged from 3.7° C. to 11.6° C. Overall, at neutral pH, the mean $T_m$±SEM was 76.2° C.±1.8° C. and 83.6° C.±2.3° C. for wild-type and mutant $V_H$Hs, respectively (FIG. 21B). At acidic pH a considerable reduction in $T_m$ was observed for both wild-type (22.1° C. to 32.4° C.) and mutant $V_H$Hs (23.7° C. to 31.2° C.) when compared to the $T_m$ values recorded at pH 7.3. However, at acidic pH the $T_m$ of all six mutants was still significantly higher than the corresponding wild-type $V_H$Hs (p=0.002, unpaired two-tailed t-test). In acid, the increase in mutant $V_HH$ $T_m$s relative to wild-type ranged from 2.1° C. to 11.6° C., which is a nearly identical spread in temperature increases to that seen at neutral pH. Overall, at pH 2.0, the mean $T_m$±SEM was 49.3° C.±1.2° C. and 56.6° C.±1.2° C. for wild-type and mutant $V_H$Hs, respectively (FIG. 21B). Interestingly, the highest $T_m$ gains at both pH were seen for the four strongest neutralizers. The $T_m$ differences between wild-type/mutant pairs are more significant at acidic pH than neutral pH. Without wishing to be bound by theory, these results (Table 6; FIG. 21) suggest the Cys[54]-Cys[78] disulfide bond may stabilize the $V_H$Hs from acid-induced denaturation.

For example, A5.1 wild-type $V_HH$ had a $T_m$ of 73.1° C. and 45.6° C. at neutral and acidic pH, respectively, while the A5.1 mutant (A5.1m) had a $T_m$ of 84.7° C. and 57.2° C. at neutral and acidic pH, respectively.

TABLE 6

Comparison of wild-type (WT) and mutant (Mut) $V_HH$ thermal unfolding midpoint temperatures ($T_m$) at neutral and acidic pH.

| | $T_m$ (° C.) at pH 7.3 | | | $T_m$ (° C.) at pH 2.0 | | |
|---|---|---|---|---|---|---|
| $V_HH$ | Wild-type | Mutant | $\Delta T_m$ | Wild-type | Mutant | $\Delta T_m$ |
| A4.2/A4.2m | 84.7* | 93.6* | 8.9 | 52.3 | 62.4 | 10.1 |
| A5.1/A5.1m | 73.1 | 84.7* | 11.6 | 45.6 | 57.2 | 11.6 |
| A19.2/A19.2m | 75.1 | 78.8 | 3.7 | 53.0 | 55.1 | 2.1 |
| A20.1/A20.1m | 72.4 | 79.1 | 6.7 | 46.6 | 55.4 | 8.8 |
| A24.1/A24.1m | 74.6 | 80.1 | 5.5 | 49.4 | 54.6 | 5.2 |
| A26.8/A26.8m | 77.2 | 85.3* | 8.1 | 48.8 | 54.8 | 6.0 |

*Minimum estimated $T_m$.

Using the thermal unfolding curves, $V_HH$ $T_{onset}$ temperatures were also identified; this is the temperature at which 5% of the $V_HH$ was unfolded (FIG. 21C; Table 7). The $T_{onset}$ of mutant $V_H$Hs was significantly higher than wild-type $V_H$Hs at both neutral and acidic pH (p=0.027 and p=0.006, respectively, unpaired two-tailed t-test). The $T_{onset}$ differences between wild-type/mutant pairs are more significant at acidic pH than neutral pH. At pH 7.3, the mean $T_{onset}$±SEM was 68.9° C.±1.8° C. and 74.9° C.±1.5° C. for wild-type and mutant $V_H$Hs, respectively. At pH 2.0, the mean $T_{onset}$±SEM was 41.2° C.±1.3° C. and 47.3° C.±1.3° C. for wild-type and mutant $V_H$Hs, respectively. Therefore, the lowest $T_{onset}$ for the mutants was 45.0° C., whereas two of the wild-type $V_H$Hs (A5.1, A20.1) already had $T_{onset}$s of ~37° C. at pH 2.0 (physiological stomach conditions).

TABLE 7

Onset temperatures ($T_{onset}$s) of wild-type and mutant $V_H$Hs. $T_{onset}$ is defined as the temperature at which 5% of the $V_HH$ is unfolded.

| | $T_{onset}$ pH 7.3 (° C.) | | $T_{onset}$ pH 2.0 (° C.) | |
|---|---|---|---|---|
| $V_HH$ | Wild-type | Mutant | Wild-type | Mutant |
| A4.2/A4.2m | 76.5 | 80.0 | 43.7 | 53.1 |
| A5.1/A5.1m | 65.2 | 76.6 | 37.8 | 48.4 |
| A19.2/A19.2m | 68.3 | 71.4 | 45.3 | 45.0 |
| A20.1/A20.1m | 64.6 | 72.0 | 37.8 | 46.3 |
| A24.1/A24.1m | 68.2 | 71.7 | 42.2 | 46.0 |
| A26.8/A26.8m | 70.7 | 77.8 | 40.3 | 45.2 |

EXAMPLE 13

Protease Resistance Profile Analysis of Mutant and Wild-type $V_H$Hs

The sensitivity of wild-type and mutant $V_H$Hs to the three major gastrointestinal proteases pepsin, trypsin, and chymotrypsin, was explored to determine whether the Cys[54]-Cys[78] disulfide bond improved $V_HH$ resistance to proteolytic degradation. The effects of the proteases were analyzed by SDS-PAGE and MS analysis.

All reactions were performed in 20 μl volumes with 4.8 μg of $V_HH$ diluted in PBS pH 7.3. For pepsin digestions, reactions contained 17 μl of $V_HH$, 2 μl of porcine stomach pepsin (460 U/mg; Sigma), and 1 μl of 1 M HCl (final pH=2.0). Final pepsin concentrations in each reaction ranged from 0.1 μg/ml to 100 μg/ml. Digestions were incubated at 37° C. for 60 min and neutralized with 1 μl of 1 M NaOH. For trypsin and chymotrypsin digestions, reactions contained 18 μl of $V_HH$ (diluted in PBS supplemented with 10 mM $CaCl_2$) and 2 μl of either trypsin or chymotrypsin (sequencing grade, Hoffmann-La Roche). Final trypsin/chymotrypsin concentrations ranged from 0.1 µg/ml to 100 µg/ml. Digestions were incubated at 37° C. for 60 min and neutralized with 1 µl of protease inhibitor cocktail (Sigma). All neutralized $V_HH$-protease reactions and controls ($V_HH$s with no protease) were separated by SDS-PAGE, stained with Coomassie and photographed using an ALPHAIMAGER 3400 (Alpha Innotech Corporation, San Leandro, Calif.). To determine the percent of $V_HH$ retained after protease digestions, densitometry analysis was performed using the ALPHAEASE Fc software package (Version 7.0.1, Alpha Innotech Corporation) on control and digested $V_HH$s. A total of three independent digestion reactions were performed on all of the $V_HH$s at each protease concentration and each were run on separate SDS-PAGE gels. Digestions at the highest protease concentration (100 µg/ml) that were not analyzed by SDS-PAGE were buffer exchanged into ddH$_2$O using Millipore BIOMAX 5K MWCO spin columns (Millipore, Billerica, Mass.) and subjected to MS analysis to identify the cleavage products, or analyzed by SPR for TcdA binding activity.

Protease concentrations of 0.1 µg/ml, 1 µg/ml, 10 µg/ml, and 100 µg/ml were explored. When the lowest concentrations of proteases (0.1 µg/ml and 1 µg/ml) were used in digestion reactions, wild-type and mutants appeared similar to undigested controls on SDS-PAGE (data not shown). Similarly, $V_HH$s were only moderately susceptible to protease degradation at 10 µg/ml (data not shown). In order to see clear differences in the proteolytic susceptibility of wild-type and mutant $V_HH$s, all remaining digestions were performed at protease concentrations of 100 µg/ml.

Figure 22:
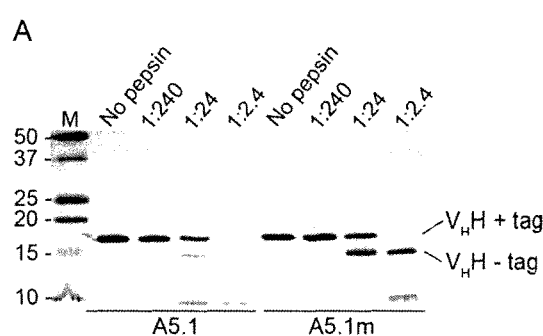
FIG. 22 shows the resistance profiles of WT and mutant $V_HH$s to the major gastrointestinal proteases pepsin, trypsin and chymotrypsin.
Figure 22:
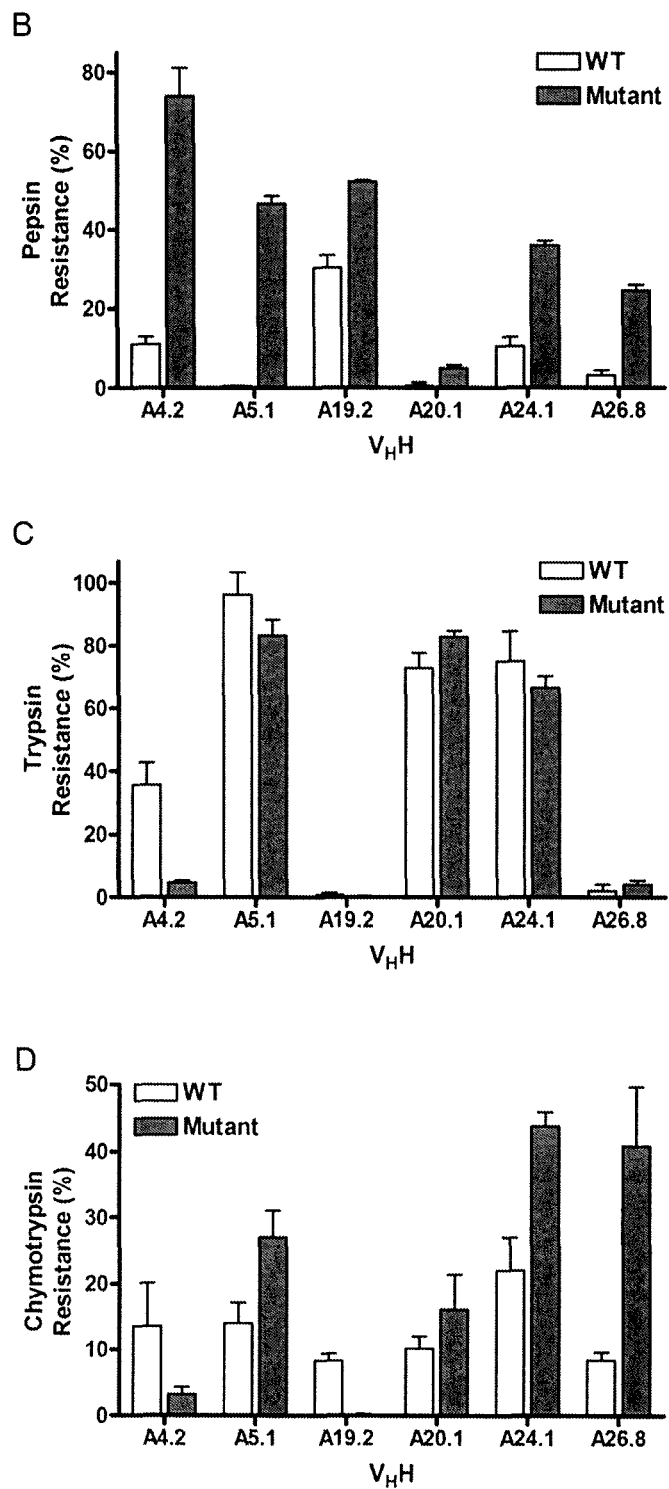
Figure 22:
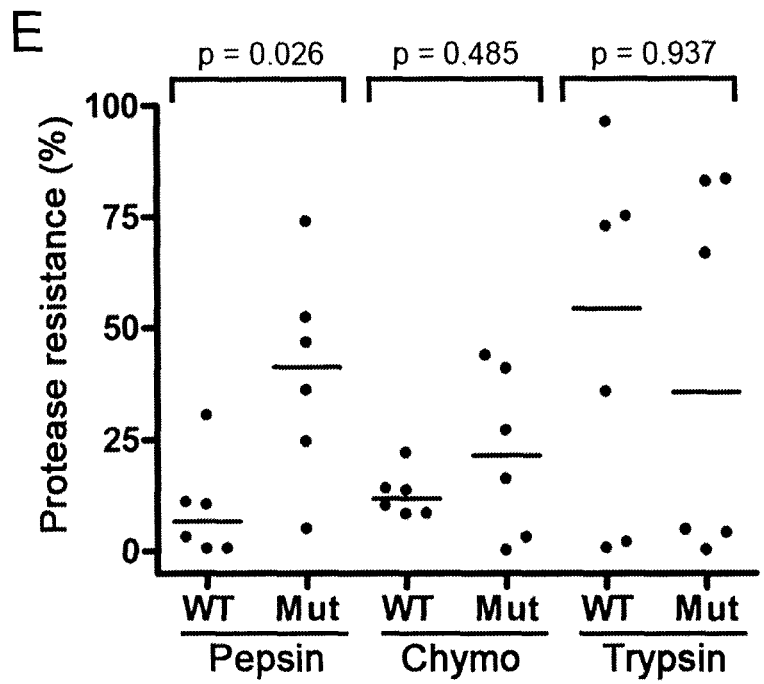

A representative SDS-PAGE gel comparing A5.1 wild-type and mutant $V_HH$ digestion with various concentrations of pepsin is shown in FIG. 22A. A reduction in $V_HH$ size from ~16 kDa (control) to either ~14 kDa, or complete digestion to smaller fragments can be observed. The band at ~14 kDa routinely appeared in digestions with each of the proteases and was shown by MS mass analysis to correspond to cleavage at various positions within the $V_HH$ C-terminal c-Myc epitope tag. Loss of the epitope tag corresponded to reductions of 1641.7 Da, 1754.8 Da, and 1641.7 Da for pepsin, trypsin, and chymotrypsin digested $V_HH$s, respectively (data not shown). Overall, significant increases in pepsin resistance were found for all mutant $V_HH$s compared to their wild-type counterparts (p=0.026, Mann-Whitney U test) (FIG. 22B, E; Table 8). All mutant $V_HH$s were found to possess greater pepsin resistance, a protease that functions at acidic pH, compared to the wild-type $V_HH$s (p=0.026, Mann-Whitney U test) (FIG. 22B, E and Table 8). The increase in mutant $V_HH$ pepsin resistance relative to corresponding wild-type ranged from almost 4.5% to 63% (Table 8). For example, A5.1 was completely degraded after incubation with pepsin, while nearly 50% of A5.1m remained intact (FIG. 22A, B). The biggest increase in pepsin resistance was found for A4.2m, where an almost 63% increase in intact $V_HH$ structure was found relative to A4.2. Interestingly, A4.2m also had the highest $T_m$ and $T_{onset}$ at pH 2.0 (Table 7), the same pH at which the pepsin digestions were performed.

In general, $V_HH$s with a higher $T_m$ at pH 2 correlated with a greater resistance to pepsin degradation (FIG. 23A) ($R^2$=0.735). Thus, while wild type $V_HH$s with lower $T_m$s occupied the low protease resistance region of the graph, the mutants with higher $T_m$s occupied the high protease resistance region of the graph. There was also a moderate correlation between $V_HH$ pepsin resistance and $T_m$s at pH 7.3 ($r^2$=0.500, data not shown). In addition, a strong correlation between wild-type $V_HH$ pepsin resistance and wild-type $V_HH$ $T_{onset}$ at pH 2.0 was noted ($r^2$=0.975, FIG. 23B). No correlation was evident between mutant $V_HH$ pepsin resistance and mutant $V_HH$ $T_{onset}$ at pH 2.0 ($r^2$=0.191, data not shown); without wishing to be bound by theory, this was likely because mutant $V_HH$ $T_{onset}$ temperatures were much higher than the temperature at which pepsin digestions were performed (37° C.).

TABLE 8

Comparison of wild-type (WT) and mutant (Mut) $V_HH$ resistance profiles to the major gastrointestinal proteases. All $V_HH$ digestions were performed at 37° C. for 1 hour in the presence of 100 µg/ml of protease; resistance profiles were obtained by comparing the intensity of protease-digested $V_HH$s relative to untreated controls using SDS-PAGE and imaging software; values represent the mean ± SEM of three independent experiments.

| $V_HH$ | Pepsin Resistance (%) | | Trypsin Resistance (%) | | Chymotrypsin Resistance (%) | |
|---|---|---|---|---|---|---|
| | WT | Mut | WT | Mut | WT | Mut |
| A4.2 | 11.08 ± 1.88 | 73.87 ± 7.23 | 35.72 ± 7.08 | 4.80 ± 0.61 | 13.60 ± 6.50 | 3.18 ± 1.10 |
| A5.1 | 0.53 ± 0.15 | 46.63 ± 1.99 | 96.23 ± 7.09 | 83.30 ± 4.96 | 14.03 ± 3.15 | 27.00 ± 4.05 |
| A19.2 | 30.37 ± 3.16 | 52.27 ± 0.32 | 0.73 ± 0.73 | 0.27 ± 0.27 | 8.30 ± 1.14 | 0.18 ± 0.10 |
| A20.1 | 0.68 ± 0.68 | 5.04 ± 0.76 | 72.77 ± 4.85 | 82.80 ± 1.97 | 10.17 ± 1.85 | 16.17 ± 5.26 |
| A24.1 | 10.45 ± 2.39 | 36.02 ± 1.11 | 75.03 ± 9.63 | 66.50 ± 3.58 | 22.03 ± 5.01 | 43.80 ± 2.08 |
| A26.8 | 3.17 ± 1.24 | 24.56 ± 1.45 | 2.03 ± 2.03 | 4.10 ± 1.27 | 8.40 ± 1.23 | 40.83 ± 8.81 |

The resistance profiles of wild-type and mutant $V_HH$s to trypsin and chymotrypsin, proteases that function at neutral pH, were more varied without a clearly defined trend (FIG. 22C-E and Table 8). 4 of 6 mutant $V_HH$s showed increased resistance to chymotrypsin, with significant increases found in clones A5.1m, A24.1m, and A26.8m (p<0.05) compared to their wild-type counterparts. No statistical differences were found between trypsin digested wild-type and mutant $V_HH$s (FIG. 22C-E; Table 8), except for A4.2m, where trypsin resistance was actually reduced from almost 36% in the wild-type $V_HH$ to almost 5% in the mutant. Both the wild-type and mutant versions of A19.2 and A26.8 were very susceptible to trypsin degradation. No correlation was evident between $V_HH$ trypsin resistance and $T_m$s at pH 7.3 or pH 2.0 ($r^2$=0.138 and $r^2$=0.138, respectively) or between $V_HH$ chymotrypsin resistance and $T_m$s at pH 7.3 or pH 2.0 ($r^2$=0.012 and $r^2$=0.004, respectively).

Figure 23:
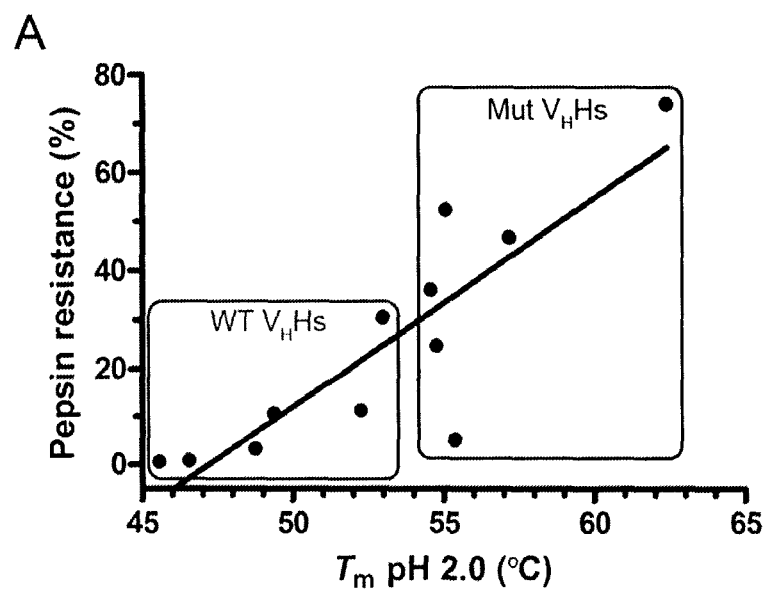
FIG. 23 shows the correlation between $V_HH$ resistance to pepsin and thermal stability at pH 2.
Figure 23:
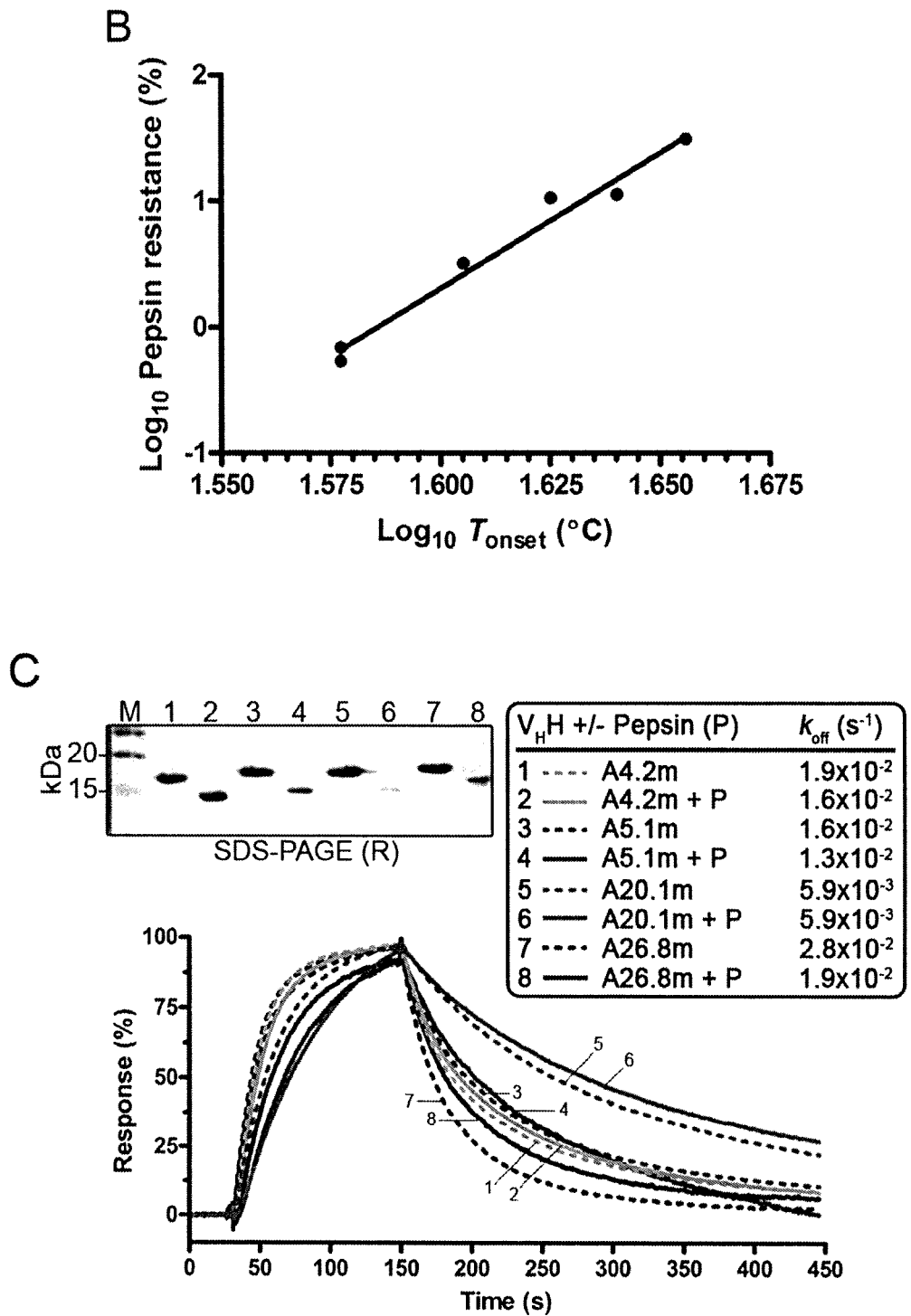

The ability of pepsin-treated mutants (A4.2m, A5.1m, A20.1m, and A26.8m) to bind TcdA was evaluated by SPR. SPR analyses confirmed the pepsin-treated mutants ("$V_HH$-tag") retained TcdA binding as their $k_{off}$ values (FIG. 23C)

were essentially the same as those of untreated controls (Table 4; FIG. 23C). SPR analysis on pepsin-digested wild-type $V_HHs$ could not be performed since these $V_HHs$ were significantly degraded by pepsin. Without wishing to be bound by theory, this highlights the impact a second disulfide bond in the hydrophobic core has on $V_HH$ conformational stability at low pH and resistance to proteolytic degradation by pepsin.

EXAMPLE 14

TcdA Toxin Neutralization Assay

In vitro TcdA neutralization assays were performed essentially as described [20]. Human lung fibroblast cell rounding was reported 24 h post addition of TcdA (100 ng/ml), TcdA+wild-type $V_HH$ (1000 nM) or TcdA+mutant $V_HH$ (1000 nM). Specifically, $V_HHs$ were added as pooled mixtures of A4.2, A5.1, A20.1, and A26.8 (250 nM each, 1000 nM total) or A4.2m, A5.1m, A20.1m, and A26.8m (250 nM each, 1000 nM total). The percentage of cell rounding was scored visually using light microscopy and the reported values are the average of two independent experiments in which each $V_HH$ mixture was tested in triplicate.

Figure 24:
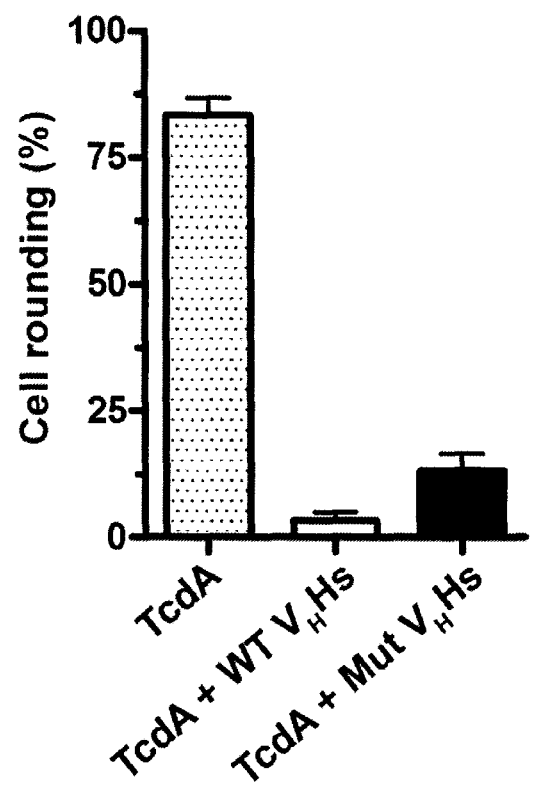
FIG. 24 is a bar graph showing that mutant $V_H$Hs retain TcdA-neutralizing capacity. Confluent monolayers of IMR-90 human lung fibroblasts were incubated with TcdA or TcdA+$V_H$Hs for 24 h, and the percentage of cells rounded was scored. $V_H$Hs (wild-type (WT) or mutant (Mut)) were added as pooled mixtures of A4.2, A5.1, A20.1, and A26.8 (250 nM each) or A4.2m, A5.1m, A20.1m, and A26.8m (250 nM each).

Mutant $V_HHs$ retained their ability to neutralize to cytotoxic effects of TcdA on monolayers of fibroblast cells. Comparison of the neutralization capacity of pooled mixtures (1000 nM total) of wild-type and mutant $V_HHs$ revealed mutants performed nearly as well as wild-types at reducing TcdA-mediated cell rounding (FIG. 24). Given that 3 of 4 mutants showed weaker affinity for TcdA the reduction in neutralizing capacity relative to wild-type $V_HHs$ was not unexpected.

As indicated above, the mutant antibodies were compared to their wild-type counterparts with respect to expression, yield, solubility, affinity for TcdA, thermal unfolding at neutral and acidic pH, and protease resistance. Mutant $V_HHs$ were found to be soluble, non-aggregating monomers, possessing similar affinity constants to that of WT $V_HHs$. A significant increase in the midpoint temperature of unfolding (4-12° C.) was observed for all mutants, at both neutral and acidic pH ($p<0.05$; unpaired two-tailed t test). Digestion of the $V_HHs$ with major gastrointestinal proteases at biologically relevant concentrations revealed a significant increase in pepsin resistance for all mutants ($p<0.05$; unpaired two-tailed Mann-Whitney U test), However, increases in resistance profiles to chymotrypsin and trypsin were not as universal. Overall, the introduction of an additional disulfide bond in the hydrophobic core of the anti-TcdA $V_HHs$ not only increased thermal stability at neutral pH, but also represents a generic strategy to increase antibody stability at low pH and impart pepsin resistance which is desirable for protein-based oral therapeutics.

EXAMPLE 15

Sequence Identities Between $V_HHs$

The sequences of $V_HH$ pairs were aligned using ClustalW (Thompson et al, 1994), and the percentage identity between the $V_HH$ pairs was calculated using the BIOEDIT Sequence Alignment Editor. Results are shown in Tables 9 and 10, below.

TABLE 9

Percentage amino acid sequence identities between TcdA-binding $V_HHs$.

| $V_HH$ 1 | $V_HH$ 2 | Identity (%) |
|---|---|---|
| A4.2 | A5.1 | 82 |
| A4.2 | A19.2 | 76 |
| A4.2 | A20.1 | 82 |
| A4.2 | A24.1 | 78 |
| A4.2 | A26.8 | 75 |
| A5.1 | A19.2 | 77 |
| A5.1 | A20.1 | 78 |
| A5.1 | A24.1 | 77 |
| A5.1 | A26.8 | 78 |
| A19.2 | A20.1 | 77 |
| A19.2 | A24.1 | 75 |
| A19.2 | A26.8 | 75 |
| A20.1 | A24.1 | 80 |
| A20.1 | A26.8 | 77 |
| A24.1 | A26.8 | 74 |
| A4.2 | A4.2m | 98.4 |
| A5.1 | A5.1m | 98.4 |
| A19.2 | A19.2m | 98.4 |
| A20.1 | A20.1m | 98.4 |
| A24.1 | A24.1m | 98.4 |
| A26.8 | A26.8m | 98.4 |

TABLE 10

Percentage amino acid sequence identities between TcdB-binding $V_HHs$.

| $V_HH$ 1 | $V_HH$ 2 | Identity (%) |
|---|---|---|
| B5.2 | B7.3 | 69 |
| B5.2 | B13.6 | 81 |
| B5.2 | B15.3 | 66 |
| B5.2 | B15.5 | 73 |
| B7.3 | B13.6 | 74 |
| B7.3 | B15.3 | 72 |
| B7.3 | B15.5 | 69 |
| B13.6 | B15.3 | 68 |
| B13.6 | B15.5 | 71 |
| B15.3 | B15.5 | 69 |
| B5.2 | B5.2m | 98.3 |
| B7.3 | B7.3m | 98.4 |
| B13.6 | B13.6m | 98.3 |
| B15.3 | B15.3m | 98.4 |
| B15.5 | B15.5m | 98.3 |

The embodiments and examples described herein are illustrative and are not meant to limit the scope of the invention as claimed. Variations of the foregoing embodiments, including alternatives, modifications and equivalents, are intended by the inventors to be encompassed by the claims. Furthermore, the discussed combination of features might not be necessary for the inventive solution.

REFERENCES

All patents, patent applications and publications referred to herein and throughout the application are hereby incorporated by reference.

Anderson, G. P., Liu, J. L., Hale, M. L., Bernstein, R. D., Moore, M., Swain, M. D., and Goldman, E. R. (2008) Anal. Chem. 80, 9604-9611.

Arbabi-Ghahroudi, M., MacKenzie, R., and Tanha, J. (2009c) Methods Mol. Biol. 525, 187-216.

Arbabi-Ghahroudi, M., MacKenzie, R., and Tanha, J. (2010) Methods Mol. Biol. 634, 309-330.

Arbabi-Ghahroudi, M., To, R., Gaudette, N., Hirama, T., Ding, W., MacKenzie, R., and Tanha, J. (2009b) Protein Eng. Des. Sel. 22, 59-66.

Babcock, G. J., Broering, T. J., Hernandez, H. J., Mandell, R. B., Donahue, K., Boatright, N., Stack, A. M., Lowy, I., Graziano, R., Molrine, D., Ambrosino, D. M., and Thomas, W. D. Jr. (2006) Infect. Immun. 74, 6339-6347.

Bell, A., Wang, Z. J., Arbabi-Ghahroudi, M., Chang, T. A., Durocher, Y., Trojahn, U., Baardsnes, J., Jaramillo, M. L., L1, S., Baral, T. N., O'Connor-McCourt, M., Mackenzie, R., and Zhang, J. (2010) Cancer Lett. 289, 81-90.

Chothia, C., and Lesk, A. M. (1987) J. Mol. Biol. 196, 901-917.

Corthier, G., Muller, M. C., Wilkins, T. D., Lyerly, D., and L'Haridon, R. (1991) Infect. Immun. 59, 1192-1195.

De Genst, E., Silence, K., Decanniere, K., Conrath, K., Loris, R., Kinne, J., Muyldermans, S., and Wyns, L. (2006) Proc. Natl. Acad. Sci. U.S.A. 103, 4586-4591.

De Kruif, J., and Logtenberg, T. (1996) J. Biol. Chem. 271, 7630-7634.

Doyle, P. J., Arbabi-Ghahroudi, M., Gaudette, N., Furzer, G., Savard, M. E., Gleddie, S., McLean, M. D., MacKenzie, C. R., and Hall, J. C. (2008) Mol. Immunol. 45, 3703-3713.

Eisenberg, D., Schwarz, E., Komaromy, M., and Wall, R. (1984) J. Mol. Biol. 179, 125-142

Fenner, L., Widmer, A. F., Goy, G., Rudin, S., and Frei, R. (2008) J. Clin. Microbiol. 46, 328-330.

Florin, I., and Thelestam, M. (1983) Biochim. Biophys. Acta 763, 383-392.

Gardiner, D. F., Rosenberg, T., Zaharatos, J., Franco, D., and Ho, D. D. (2009) Vaccine 27, 3598-3604.

Giannasca, P. J., Zhang, Z. X., Lei, W. D., Boden, J. A., Giel, M. A., Monath, T. P., and Thomas, W. D. Jr. (1999) Infect. Immun. 67, 527-538.

Goldman, E. R., Anderson, G. P., Conway, J., Sherwood, L. J., Fech, M., Vo, B., Liu, J. L., and Hayhurst, A. (2008) Anal. Chem. 80, 8583-8591.

Goldman, E. R., Anderson, G. P., Liu, J. L., Delehanty, J. B., Sherwood, L. J., Osborn, L. E., Cummins, L. B., and Hayhurst, A. (2006) Anal. Chem. 78, 8245-8255.

Greco, A., Ho, J. G., Lin, S. J., Palcic, M. M., Rupnik, M., and Ng, K. K. (2006) Nat. Struct. Mol. Biol. 13, 460-461.

Hagihara, Y., Mine, S., and Uegaki, K. (2007) J. Biol. Chem. 282, 36489-36495.

Hamers-Casterman, C., Atarhouch, T., Muyldermans, S., Robinson, G., Hamers, C., Songa, E. B., Bendahman, N., and Hamers, R. (1993) Nature 363, 446-448.

Hassoun, A., and Ibrahim, F. (2007) Am. J. Geriatr. Pharmacother. 5, 48-51.

Ho, S. N., Hunt, H. D., Horton, R. M., Pullen, J. K., and Pease, L. R. (1989) Gene 77, 51-59.

Hmila, I., Abdallah, R. B. A., Saerens, D., Benlasfar, Z., Conrath, K., Ayeb, M. E., Muyldermans, S., and Bouhaouala-Zahar, B. (2008) Mol. Immunol. 45, 3847-3856.

Hussack, G., Luo, Y., Veldhuis, L., Hall, J. C., Tanha, J., and MacKenzie, R. (2009) Sensors 9, 5351-5367.

Hussack, G., Hirama, T., Ding, W., MacKenzie, R., and Tanha, J. (2011) PLoS ONE, In press.

Iqbal, U., Trojahn, U., Albaghdadi, H., Zhang, J., O'Connor, M., Stanimirovic, D., Tomanek, B., Sutherland, G., and Abulrob, A. (2010) Br. J. Pharmacol. 160, 1016-1028.

Jank, T., and Aktories, K. (2008) Trends Microbiol. 16, 222-229.

Jank, T., Giesemann, T., and Aktories, K. (2007) Glycobiology 17, 15R-22R.

Jespers, L., Schon, O., Famm, K., and Winter, G. (2004) Nat. Biotechnol. 22, 1161-1165.

Johal, S. S., Lambert, C. P., Hammond, J., James, P. D., Borriello, S. P., and Mahida, Y. R. (2004) J. Clin. Pathol. 57, 973-979.

Johnson, S. (2009) J. Infect. 58, 403-410.

Juang, P., Skledar, S. J., Zgheib, N. K., Paterson, D. L., Vergis, E. N., Shannon, W. D., Ansani, N. T., and Branch, R. A. (2007) Am. J. Infect. Control 35, 131-137.

Kabat, E. A., and Wu, T. T. (1991) J. Immunol. 147:1709-19.

Katchar, K., Taylor, C. P., Tummala, S., Chen, X., Sheikh, J., and Kelly, C. P. (2007) Clin. Gastroenterol. Hepatol. 5, 707-713.

Keel, M. K., and Songer, J. G. (2007) Vet. Pathol. 44, 814-822.

Kelly, C. P., Chetham, S., Keates, S., Bostwick, E. F., Roush, A. M., Castagliuolo, I., LaMont J. T., and Pothoulakis, C. (1997) Antimicrob. Agents Chemother. 41, 236-241.

Kelly, C. P., Pothoulakis, C., and LaMount, J. T. (1994) N. Engl. J. Med. 330, 257-262.

Kelly, C. P., Pothoulakis, C., Oreliana, J., and LaMont, J. T. (1992) Gastroenterology 102, 35-40 (2009) Nat. Rev. Drug Discov. 8, 442.

Kelly, C. P., Pothoulakis, C., Vavva, F., Castagliuolo, I., Bostwick, E. F., O'Keane, J. C., Keates, S., and LaMont, J. T. (1996) Antimicrob. Agents Chemother. 40, 373-379.

Kink, J. A., and Williams, J. A. (1998) Infect. Immun. 66, 2018-2025.

Kyne, L., Hamel, M. B., Polavaram, R., and Kelly, C. P. (2002) Clin. Infect. Dis. 34, 346-353.

Kyne, L., Warny, M., Qamar, A., and Kelly, C. P. (2000) N. Engl. J. Med. 340, 390-397.

Kyne, L., Warny, M., Qamar, A., and Kelly, C. P. (2001) Lancet 357, 189-193.

Leffler, D. A., and Lamont, J. T. (2009) Gastroenterology 136, 1899-1912.

Lefranc, M.-P. et al., (2003) Dev. Comp. Immunol., 27, 55-77.

Leung, D. Y., Kelly, C. P., Boguniewicz, M., Pothoulakis, C., LaMont, J. T., and Flores, A. (1991) J. Pediatr. 118, 633-637.

Liu, J. L., Anderson, G. P., and Goldman, E. R. (2007a) BMC Biotechnol. 7, 78-88.

Lowy, I., Molrine, D. C., Leav, B. A., Blair, B. M., Baxter, R., Gerding, D. N., Nichol, G., Thomas, W. D. Jr., Leney, M., Sloan, S., Hay, C. A., and Ambrosino, D. M. (2010) N. Engl. J. Med. 362, 197-205.

Lyerly, D. M., Bostwick, E. F., Binion, S. B., and Wilkins, T. D. (1991) Infect. Immun. 59, 2215-2218.

Lyerly, D. M., Phelps, C. J., Toth, J., and Wilkins, J. D. (1986) Infect. Immun. 54, 70-76.

Lyras, D., O'Connor, J. R., Howarth, P. M., Sambol, S. P., Carter, G. P., Phumoonna, T., Poon, R., Adams, V., Vedantam, G., Johnson, S., Gerding, D. N., and Rood, J. I. (2009) Nature 458, 1176-1179.

McPherson, S., Rees, C. J., Ellis, R., Soo, S., and Panter, S. J. (2006) Dis. Colon Rectum 49, 640-645.

Merritt, E. A., and Hol, W. G. (1995) Curr. Opin. Struct. Biol. 5, 165-171.

Musher, D. M., Manhas, A., Jain, P., Nuila, F., Waqar, A., Logan, N., Marino, B., Graviss, E. A. (2007) J. Clin. Microbial. 45, 2737-2739.

Nielsen, U. B., Adams, G. P., Weiner, L. M., and Marks, J. D. (2000) Cancer Res. 60, 6434-6440.

Nuttall, S. D., Krishnan, U. V., Doughty, L., Pearson, K., Ryan, M. T., Hoogenraad, N. J., Hattarki, M., Carmichael, J. A., Irving, R. A., and Hudson, P. J. (2003) Eur. J. Biochem. 270, 3543-3554.

O'Connor, J. R., Johnson, S., and Gerding, D. N. (2009) Gastroenterology 136, 1913-1924.

Ochsner, U. A., Bell, S. J., O'Leary, A. L., Hoang, T., Stone, K. C., Young, C. L., Critchley, I. A., and Janjic, N. (2009) J. Antimicrob. Chemother. 63, 964-971.

Pace, C. N., Vajdos, F., Fee, L., Grimsley, G., and Gray, T. (1995) Protein Sci. 4, 2411-2423.

Pépin, J., Valiquette, L., and Cassette, B. (2005) CMAJ 173, 1037-1042.

Planche, T., Aghaizu, A., Holliman, R., Riley, P., Poloniecki, J., Breathnach, A., and Krishna, S. (2008) Lancet Infect. Dis. 8, 777-784.

Ridgway, J. B., Presta, L. G., and Carter, P. (1996) Protein Eng. 9, 617-621.

Rupnik, M., Wilcox, M. H., and Gerding, D. N. (2009) Nat. Rev. Microbial. 7, 526-536.

Rüssmann, H., Panthel, K., Bader, R. C., Schmitt, C., and Schaumann, R. (2007) Eur. J. Clin. Microbial. Infect. Dis. 26, 115-119.

Saerens, D., Conrath, K., Govaert, J., and Muyldermans, S. (2008) J. Mol. Biol. 377, 478-488.

Salcedo, J., Keates, S., Pothoulakis, C., Warny, M., Castagliuolo, I., LaMont, J. T., and Kelly, C. P. (1997) Gut 41, 366-370.

Salnikova, M. S., Joshi, S. B., Rytting, J. H., Warny, M., and Middaugh, C. R. (2008) J. Pharm. Sci. 97, 3735-3752.

Sloan, L. M., Duresko, B. J., Gustafson, D. R., and Rosenblatt, J. E. (2008) J. Clin. Microbial. 46, 1996-2001.

Songer, J. G. (2004) Anim. Health Res. Rev. 5, 321-326.

Stewart, C. S., MacKenzie, C. R., and Hall, J. C. (2007) Toxicon 49, 699-709.

Tanha, J., Muruganandam, A., and Stanimirovic, D. (2003) Methods Mol. Med. 89, 435-449.

Thompson, J. D., Higgins, D. G., and Gibson, T. J. (1994) Nucleic Acids Res. 22, 4673-4680.

Tjellström, B., Stenhammar, L., Eriksson, S., and Magnusson, K. E. (1993) Lancet 341, 701-702.

To, R., Hirama, T., Arbabi-Ghahroudi, M., MacKenzie, R., Wang, P., Xu, P., Ni, F., and Tanha, J. (2005) J. Biol. Chem. 280, 41395-41403.

Turgeon, D. K., Novicki, T. J., Quick, J., Carlson, L., Miller, P., Ulness, B., Cent, A., Ashley, R., Larson, A., Coyle, M., Limaye, A. P., Cookson, B. T., and Fritsche, T. R. (2003) J. Clin. Microbiol. 41, 667-670.

Viscidi, R., Laughon, B. E., Yolken, R., Bo-Linn, P., Moench, T., Ryeder, R. W., and Bartlett, J. G. (1983) J. Infect. Dis. 148, 93-100.

Vu, K. B., Ghahroudi, M. A., Wyns, L., and Muyldermans, S. (1997) Mol. Immunol. 34, 1121-1131.

Warny, M., Fatimi, A., Bostwick, E. F., Laine, D. C., Label, F., LaMont, J. T., Pothoulakis, C., and Kelly, C. P. (1999) Gut 44, 212-217.

Warny, M., Pepin, J., Fang, A., Killgore, G., Thompson, A., Brazier, J., Frost, E., and McDonald, L. C. (2005) Lancet 366, 1079-1084.

Warny, M., Vaerman, J. P., Avesani, V., and Delmée, M. (1994) Infect. Immun. 62, 384-389.

Wesolowski, J., Alzogaray, V., Reyelt, J., Unger, M., Juarez, K., Urrutia, M., Cauerhff, A., Danguah, W., Rissiek, B., Scheuplein, F., Schwarz, N., Adriouch, S., Boyer, O., Seman, M., Licea, A., Serreze, D. V., Goldbaum, F. A., Haag, F., and Koch-Nolte, F. (2009) Med. Microbiol. Immunol. 198, 157-174.

Wilcox, N. H. (2004) J. Antimicrob. Chemother. 53, 882-884.

Wilkins, T. D., and Lyerly, D. M. (2003) J. Clin. Microbiol. 41, 531-534.

Zhang, J., Li, Q., Nguyen, T.-D., Tremblay, T.-L., Stone, E., To, R., Kelly, J., and MacKenzie, C. R. (2004a) J. Mol. Biol. 341, 161-169.

Zhang, J., Tanha, J., Hirama, T., Khiew, N. H., To, R., Tong-Sevinc, H., Stone, E., Brisson, J. R., and MacKenzie, C. R. (2004b) J. Mol. Biol. 335, 49-56.

---

What is claimed is:

1. An isolated or purified single domain antibody, comprising a sequence of CDR 1 of GRTFSMYR (SEQ ID NO:2); CDR2 of ITRNGSST (SEQ ID NO:8); and CDR3 of AATSGSSYLDAAHVYDY (SEQ ID NO:14).

2. The isolated or purified single domain antibody of claim 1, comprising a sequence selected from the group consisting of:

```
                                          (SEQ ID NO: 35)
QVKLEESGGGLVQAGGSLRLSCAASGRTFSMYRMGWFRQAPGKEREFVGV

ITRNGSSTYYADSVKGRFTISRDNAKNTVYLQMNSLKPEDTALYYCAATS

GSSYLDAAHVYDYWGQGTQVTVSS;
and (SEQ ID NO: 46)
QVKLEESGGGLVQAGGSLRLSCAASGRTFSMYRMGWFRQAPGKEREFVCV

ITRNGSSTYYADSVKGRFTCSRDNAKNTVYLQMNSLKPEDTALYYCAATS

GSSYLDAAHVYDYWGQGTQVTVSS,
``` or a sequence at least 90% identical thereto, wherein any differences in sequence are limited to framework regions of the single domain antibody.

3. A multivalent polypeptide comprising at least one of the isolated or purified single domain antibody of claim 1.

4. The isolated or purified single domain antibody of claim 1, wherein the antibody is immobilized onto a surface.

5. The isolated or purified single domain antibody of claim 1, wherein the antibody is linked to a cargo molecule.

6. The isolated or purified single domain antibody of claim 5, wherein the cargo molecule is a detectable agent, a therapeutic, a drug, a peptide, a carbohydrate moiety, an enzyme, or a cytotoxic agent; one or more liposomes loaded with a detectable agent, a therapeutic, a drug, a peptide, an enzyme, or a cytotoxic agent; or one or more nanoparticle, nanowire, nanotube, or quantum dots.

7. A composition comprising one or more than one of the isolated or purified single domain antibody of claim 1 and a pharmaceutically-acceptable carrier, diluent, or excipient.

8. A method of treating a *Clostridium difficile* infection, comprising administering isolated or purified single domain antibody, comprising a sequence selected from the group consisting of:

```
                                          (SEQ ID NO: 35)
QVKLEESGGGLVQAGGSLRLSCAASGRTFSMYRMGWFRQAPGKEREFVGV

ITRNGSSTYYADSVKGRFTISRDNAKNTVYLQMNSLKPEDTALYYCAATS

GSSYLDAAHVYDYWGQGTQVTVSS;
and (SEQ ID NO: 46)
QVKLEESGGGLVQAGGSLRLSCAASGRTFSMYRMGWFRQAPGKEREFVCV

ITRNGSSTYYADSVKGRFTCSRDNAKNTVYLQMNSLKPEDTALYYCAATS

GSSYLDAAHVYDYWGQGTQVTVSS
``` to a subject in need thereof.

9. A method of detecting *Clostridium difficile* toxins comprising contacting a sample with an isolated or purified single domain antibody comprising a sequence selected from the group consisting of

```
                                          (SEQ ID NO: 35)
QVKLEESGGGLVQAGGSLRLSCAASGRTFSMYRMGWFRQAPGKEREFVGV

ITRNGSSTYYADSVKGRFTISRDNAKNTVYLQMNSLKPEDTALYYCAATS

GSSYLDAAHVYDYWGQGTQVTVSS
and (SEQ ID NO: 46)
QVKLEESGGGLVQAGGSLRLSCAASGRTFSMYRMGWFRQAPGKEREFVCV

ITRNGSSTYYADSVKGRFTCSRDNAKNTVYLQMNSLKPEDTALYYCAATS

GSSYLDAAHVYDYWGQGTQVTVSS;
``` allowing the *Clostridium difficile* toxin to bind the isolated or purified single domain antibody; and detecting the bound single domain antibody or fragment thereof using a suitable detection and/or imaging technology.

* * * * *

SEQUENCE LISTING

```
<160> NUMBER OF SEQ ID NOS: 90

<210> SEQ ID NO 1
<211> LENGTH: 8
<212> TYPE: PRT
<213> ORGANISM: Artificial
<220> FEATURE:
<223> OTHER INFORMATION: anti-TcdA CDR1

<400> SEQUENCE: 1

Gly Arg Thr Phe Asn Thr Leu Ser
1               5

<210> SEQ ID NO 2
<211> LENGTH: 8
<212> TYPE: PRT
<213> ORGANISM: Artificial
<220> FEATURE:
<223> OTHER INFORMATION: anti-TcdA CDR1

<400> SEQUENCE: 2

Gly Arg Thr Phe Ser Met Tyr Arg
1               5

<210> SEQ ID NO 3
<211> LENGTH: 8
<212> TYPE: PRT
```

```
<213> ORGANISM: Artificial
<220> FEATURE:
<223> OTHER INFORMATION: anti-TcdA CDR1

<400> SEQUENCE: 3

Gly Arg Thr Leu Ser Ser Tyr Ile
1               5

<210> SEQ ID NO 4
<211> LENGTH: 8
<212> TYPE: PRT
<213> ORGANISM: Artificial
<220> FEATURE:
<223> OTHER INFORMATION: anti-TcdA CDR1

<400> SEQUENCE: 4

Gly Arg Thr Phe Ser Met Asp Pro
1               5

<210> SEQ ID NO 5
<211> LENGTH: 8
<212> TYPE: PRT
<213> ORGANISM: Artificial
<220> FEATURE:
<223> OTHER INFORMATION: anti-TcdA CDR1

<400> SEQUENCE: 5

Ile Arg Ser Phe Ser Asn Arg Asn
1               5

<210> SEQ ID NO 6
<211> LENGTH: 8
<212> TYPE: PRT
<213> ORGANISM: Artificial
<220> FEATURE:
<223> OTHER INFORMATION: anti-TcdA CDR1

<400> SEQUENCE: 6

Glu Arg Thr Phe Ser Arg Tyr Pro
1               5

<210> SEQ ID NO 7
<211> LENGTH: 8
<212> TYPE: PRT
<213> ORGANISM: Artificial
<220> FEATURE:
<223> OTHER INFORMATION: anti-TcdA CDR2

<400> SEQUENCE: 7

Val Ser Arg Ser Gly Gly Ser Thr
1               5

<210> SEQ ID NO 8
<211> LENGTH: 8
<212> TYPE: PRT
<213> ORGANISM: Artificial
<220> FEATURE:
<223> OTHER INFORMATION: anti-TcdA CDR2

<400> SEQUENCE: 8

Ile Thr Arg Asn Gly Ser Ser Thr
1               5

<210> SEQ ID NO 9
<211> LENGTH: 8
<212> TYPE: PRT
<213> ORGANISM: Artificial
```

```
<220> FEATURE:
<223> OTHER INFORMATION: anti-TcdA CDR2

<400> SEQUENCE: 9

Ile Ser Arg Arg Gly Gly Asn Ser
1               5

<210> SEQ ID NO 10
<211> LENGTH: 8
<212> TYPE: PRT
<213> ORGANISM: Artificial
<220> FEATURE:
<223> OTHER INFORMATION: anti-TcdA CDR2

<400> SEQUENCE: 10

Gly Ser Ser Thr Gly Arg Thr Thr
1               5

<210> SEQ ID NO 11
<211> LENGTH: 8
<212> TYPE: PRT
<213> ORGANISM: Artificial
<220> FEATURE:
<223> OTHER INFORMATION: anti-TcdA CDR2

<400> SEQUENCE: 11

Ile Ser Trp Gly Gly Gly Ser Thr
1               5

<210> SEQ ID NO 12
<211> LENGTH: 8
<212> TYPE: PRT
<213> ORGANISM: Artificial
<220> FEATURE:
<223> OTHER INFORMATION: anti-TcdA CDR2

<400> SEQUENCE: 12

Ile Ser Ser Thr Gly Thr Ser Thr
1               5

<210> SEQ ID NO 13
<211> LENGTH: 18
<212> TYPE: PRT
<213> ORGANISM: Artificial
<220> FEATURE:
<223> OTHER INFORMATION: anti-TcdA CDR3

<400> SEQUENCE: 13

Ala Ala Ala Ala Thr Lys Ser Asn Thr Thr Ala Tyr Arg Leu Ser Phe
1               5                   10                  15

Asp Tyr

<210> SEQ ID NO 14
<211> LENGTH: 17
<212> TYPE: PRT
<213> ORGANISM: Artificial
<220> FEATURE:
<223> OTHER INFORMATION: anti-TcdA CDR3

<400> SEQUENCE: 14

Ala Ala Thr Ser Gly Ser Ser Tyr Leu Asp Ala Ala His Val Tyr Asp
1               5                   10                  15

Tyr

<210> SEQ ID NO 15
```

```
<211> LENGTH: 21
<212> TYPE: PRT
<213> ORGANISM: Artificial
<220> FEATURE:
<223> OTHER INFORMATION: anti-TcdA CDR3

<400> SEQUENCE: 15

Ala Ala Asp Gly Ser Val Ala Gly Trp Gly Arg Arg Ser Val Ser Val
1               5                   10                  15

Ser Ser Tyr Asp Tyr
            20

<210> SEQ ID NO 16
<211> LENGTH: 16
<212> TYPE: PRT
<213> ORGANISM: Artificial
<220> FEATURE:
<223> OTHER INFORMATION: anti-TcdA CDR3

<400> SEQUENCE: 16

Ala Ala Ala Pro Tyr Gly Ala Asn Trp Tyr Arg Asp Glu Tyr Ala Tyr
1               5                   10                  15

<210> SEQ ID NO 17
<211> LENGTH: 17
<212> TYPE: PRT
<213> ORGANISM: Artificial
<220> FEATURE:
<223> OTHER INFORMATION: anti-TcdA CDR3

<400> SEQUENCE: 17

Ala Ala Glu Phe Gly His Asn Ile Ala Thr Ser Ser Asp Glu Tyr Asp
1               5                   10                  15

Tyr

<210> SEQ ID NO 18
<211> LENGTH: 17
<212> TYPE: PRT
<213> ORGANISM: Artificial
<220> FEATURE:
<223> OTHER INFORMATION: anti-TcdA CDR3

<400> SEQUENCE: 18

Ala Val Asn Ser Gln Arg Thr Arg Leu Gln Asp Pro Asn Glu Tyr Asp
1               5                   10                  15

Tyr

<210> SEQ ID NO 19
<211> LENGTH: 8
<212> TYPE: PRT
<213> ORGANISM: Artificial
<220> FEATURE:
<223> OTHER INFORMATION: anti-TcdB CDR1

<400> SEQUENCE: 19

Gly Asn Ile Phe Ser Ile Asn Thr
1               5

<210> SEQ ID NO 20
<211> LENGTH: 8
<212> TYPE: PRT
<213> ORGANISM: Artificial
<220> FEATURE:
<223> OTHER INFORMATION: anti-TcdB CDR1

<400> SEQUENCE: 20
```

```
Gly Arg Thr Ala Ser Gly Tyr Gly
1               5

<210> SEQ ID NO 21
<211> LENGTH: 8
<212> TYPE: PRT
<213> ORGANISM: Artificial
<220> FEATURE:
<223> OTHER INFORMATION: anti-TcdB CDR1

<400> SEQUENCE: 21

Gly Arg Thr Phe Ser Ser Gly Val
1               5

<210> SEQ ID NO 22
<211> LENGTH: 6
<212> TYPE: PRT
<213> ORGANISM: Artificial
<220> FEATURE:
<223> OTHER INFORMATION: anti-TcdB CDR1

<400> SEQUENCE: 22

Gly Leu Ser Arg Tyr Ala
1               5

<210> SEQ ID NO 23
<211> LENGTH: 8
<212> TYPE: PRT
<213> ORGANISM: Artificial
<220> FEATURE:
<223> OTHER INFORMATION: anti-TcdB CDR1

<400> SEQUENCE: 23

Gly Ser Ile Ser Arg Ile Ser Thr
1               5

<210> SEQ ID NO 24
<211> LENGTH: 7
<212> TYPE: PRT
<213> ORGANISM: Artificial
<220> FEATURE:
<223> OTHER INFORMATION: anti-TcdB CDR2

<400> SEQUENCE: 24

Ile Thr Ser Gly Gly Thr Thr
1               5

<210> SEQ ID NO 25
<211> LENGTH: 8
<212> TYPE: PRT
<213> ORGANISM: Artificial
<220> FEATURE:
<223> OTHER INFORMATION: anti-TcdB CDR2

<400> SEQUENCE: 25

Ile Ser Arg Ser Gly Ala Gly Thr
1               5

<210> SEQ ID NO 26
<211> LENGTH: 7
<212> TYPE: PRT
<213> ORGANISM: Artificial
<220> FEATURE:
<223> OTHER INFORMATION: anti-TcdB CDR2

<400> SEQUENCE: 26
```

Ile Thr Thr Gly Gly Ser Thr
1               5

<210> SEQ ID NO 27
<211> LENGTH: 8
<212> TYPE: PRT
<213> ORGANISM: Artificial
<220> FEATURE:
<223> OTHER INFORMATION: anti-TcdB CDR2

<400> SEQUENCE: 27

Thr Asn Trp Ser Ser Gly Asn Thr
1               5

<210> SEQ ID NO 28
<211> LENGTH: 7
<212> TYPE: PRT
<213> ORGANISM: Artificial
<220> FEATURE:
<223> OTHER INFORMATION: anti-TcdB CDR2

<400> SEQUENCE: 28

Ile Ser Thr Gly Gly Thr Thr
1               5

<210> SEQ ID NO 29
<211> LENGTH: 15
<212> TYPE: PRT
<213> ORGANISM: Artificial
<220> FEATURE:
<223> OTHER INFORMATION: anti-TcdB CDR3

<400> SEQUENCE: 29

Asn Thr Val Lys Val Val Gly Gly Arg Leu Asp Asn Pro Asp Tyr
1               5                   10                  15

<210> SEQ ID NO 30
<211> LENGTH: 20
<212> TYPE: PRT
<213> ORGANISM: Artificial
<220> FEATURE:
<223> OTHER INFORMATION: anti-TcdB CDR3

<400> SEQUENCE: 30

Val Ala Arg Pro Thr Lys Val Asp Arg Asp Tyr Ala Thr Arg Glu
1               5                   10                  15

Met Tyr Asn Tyr
            20

<210> SEQ ID NO 31
<211> LENGTH: 15
<212> TYPE: PRT
<213> ORGANISM: Artificial
<220> FEATURE:
<223> OTHER INFORMATION: anti-TcdB CDR3

<400> SEQUENCE: 31

Asn Ser Val Ala Val Val Gly Gly Val Ile Lys Ser Pro Asp Tyr
1               5                   10                  15

<210> SEQ ID NO 32
<211> LENGTH: 17
<212> TYPE: PRT
<213> ORGANISM: Artificial
<220> FEATURE:
<223> OTHER INFORMATION: anti-TcdB CDR3

```
<400> SEQUENCE: 32

Ala Ala Arg Lys Leu Asp Val Pro Ser Arg Tyr Ser Gln His Tyr Asp
1               5                   10                  15

Tyr

<210> SEQ ID NO 33
<211> LENGTH: 15
<212> TYPE: PRT
<213> ORGANISM: Artificial
<220> FEATURE:
<223> OTHER INFORMATION: anti-TcdB CDR3

<400> SEQUENCE: 33

Ala Ala Gly Trp Lys Val Val Arg Gly Ser Leu Glu Tyr Glu Tyr
1               5                   10                  15

<210> SEQ ID NO 34
<211> LENGTH: 125
<212> TYPE: PRT
<213> ORGANISM: Artificial
<220> FEATURE:
<223> OTHER INFORMATION: Anti-TcdA sdAb

<400> SEQUENCE: 34

Gln Val Lys Leu Glu Glu Ser Gly Gly Gly Leu Val Gln Ala Gly Gly
1               5                   10                  15

Ser Leu Arg Leu Ser Cys Ala Ala Ser Gly Arg Thr Phe Asn Thr Leu
            20                  25                  30

Ser Met Gly Trp Phe Arg Gln Ala Pro Gly Lys Glu Arg Glu Phe Val
        35                  40                  45

Ala Ala Val Ser Arg Ser Gly Gly Ser Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Ala Ala Thr Lys Ser Asn Thr Thr Ala Tyr Arg Leu Ser Phe
            100                 105                 110

Asp Tyr Trp Gly Gln Gly Thr Gln Val Thr Val Ser Ser
        115                 120                 125

<210> SEQ ID NO 35
<211> LENGTH: 124
<212> TYPE: PRT
<213> ORGANISM: Artificial
<220> FEATURE:
<223> OTHER INFORMATION: Anti-TcdA sdAb

<400> SEQUENCE: 35

Gln Val Lys Leu Glu Glu Ser Gly Gly Gly Leu Val Gln Ala Gly Gly
1               5                   10                  15

Ser Leu Arg Leu Ser Cys Ala Ala Ser Gly Arg Thr Phe Ser Met Tyr
            20                  25                  30

Arg Met Gly Trp Phe Arg Gln Ala Pro Gly Lys Glu Arg Glu Phe Val
        35                  40                  45

Gly Val Ile Thr Arg Asn Gly Ser Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80
```

```
Leu Gln Met Asn Ser Leu Lys Pro Glu Asp Thr Ala Leu Tyr Tyr Cys
                 85                  90                  95

Ala Ala Thr Ser Gly Ser Ser Tyr Leu Asp Ala Ala His Val Tyr Asp
            100                 105                 110

Tyr Trp Gly Gln Gly Thr Gln Val Thr Val Ser Ser
        115                 120

<210> SEQ ID NO 36
<211> LENGTH: 128
<212> TYPE: PRT
<213> ORGANISM: Artificial
<220> FEATURE:
<223> OTHER INFORMATION: Anti-TcdA sdAb

<400> SEQUENCE: 36

Gln Val Lys Leu Glu Glu Ser Gly Gly Leu Val Gln Pro Gly Gly
1               5                   10                  15

Ser Leu Arg Leu Ser Cys Ala Ala Ser Gly Arg Thr Leu Ser Ser Tyr
            20                  25                  30

Ile Val Ala Trp Phe Arg Gln Ala Pro Gly Lys Glu Arg Glu Phe Val
            35                  40                  45

Ala Gly Ile Ser Arg Arg Gly Gly Asn Ser Ala Tyr Val Glu Ser Val
        50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                 85                  90                  95

Ala Ala Asp Gly Ser Val Ala Gly Trp Gly Arg Arg Ser Val Ser Val
            100                 105                 110

Ser Ser Tyr Asp Tyr Trp Gly Gln Gly Thr Gln Val Thr Val Ser Ser
            115                 120                 125

<210> SEQ ID NO 37
<211> LENGTH: 123
<212> TYPE: PRT
<213> ORGANISM: Artificial
<220> FEATURE:
<223> OTHER INFORMATION: Anti-TcdA sdAb

<400> SEQUENCE: 37

Gln Val Gln Leu Val Glu Ser Gly Gly Gly Leu Ala Gln Ala Gly Gly
1               5                   10                  15

Ser Leu Arg Leu Ser Cys Ala Ala Ser Gly Arg Thr Phe Ser Met Asp
            20                  25                  30

Pro Met Ala Trp Phe Arg Gln Pro Pro Gly Lys Glu Arg Glu Phe Val
            35                  40                  45

Ala Ala Gly Ser Ser Thr Gly Arg Thr Thr Tyr Tyr Ala Asp Ser Val
        50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                 85                  90                  95

Ala Ala Ala Pro Tyr Gly Ala Asn Trp Tyr Arg Asp Gly Tyr Ala Tyr
            100                 105                 110

Trp Gly Gln Gly Thr Gln Val Thr Val Ser Ser
        115                 120

<210> SEQ ID NO 38
```

```
<211> LENGTH: 124
<212> TYPE: PRT
<213> ORGANISM: Artificial
<220> FEATURE:
<223> OTHER INFORMATION: Anti-TcdA sdAb

<400> SEQUENCE: 38

Gln Val Gln Leu Val Glu Ser Gly Gly Gly Leu Val Gln Ala Gly Gly
1               5                   10                  15

Ser Leu Arg Leu Ser Cys Ala Ala Ser Ile Arg Ser Phe Ser Asn Arg
            20                  25                  30

Asn Met Gly Trp Phe Arg Gln Pro Pro Gly Lys Glu Arg Glu Phe Val
        35                  40                  45

Ala Gly Ile Ser Trp Gly Gly Ser Thr Arg Tyr Ala Asp Ser Val
    50                  55                  60

Lys Gly Arg Phe Thr Ile Ser Arg Asp Asn Ala Lys Lys Thr Val Tyr
65                  70                  75                  80

Leu Gln Met Asn Ser Leu Lys Pro Glu Asp Thr Ala Val Tyr Tyr Cys
                85                  90                  95

Ala Ala Glu Phe Gly His Asn Ile Ala Thr Ser Ser Asp Glu Tyr Asp
            100                 105                 110

Tyr Trp Gly Gln Gly Thr Gln Val Thr Val Ser Ser
        115                 120

<210> SEQ ID NO 39
<211> LENGTH: 124
<212> TYPE: PRT
<213> ORGANISM: Artificial
<220> FEATURE:
<223> OTHER INFORMATION: Anti-TcdA sdAb

<400> SEQUENCE: 39

Gln Val Lys Leu Glu Glu Ser Gly Gly Gly Leu Val Gln Ala Gly Gly
1               5                   10                  15

Ser Leu Arg Leu Ser Cys Ala Ala Ser Glu Arg Thr Phe Ser Arg Tyr
            20                  25                  30

Pro Val Ala Trp Phe Arg Gln Ala Pro Gly Ala Glu Arg Glu Phe Val
        35                  40                  45

Ala Val Ile Ser Ser Thr Gly Thr Ser Thr Tyr Tyr Ala Asp Ser Val
    50                  55                  60

Lys Gly Arg Phe Thr Ile Ser Arg Asp Asn Ala Lys Val Thr Val Tyr
65                  70                  75                  80

Leu Gln Met Asn Asn Leu Lys Arg Glu Asp Thr Ala Val Tyr Phe Cys
                85                  90                  95

Ala Val Asn Ser Gln Arg Thr Arg Leu Gln Asp Pro Asn Glu Tyr Asp
            100                 105                 110

Tyr Trp Gly Gln Gly Thr Gln Val Thr Val Ser Ser
        115                 120

<210> SEQ ID NO 40
<211> LENGTH: 121
<212> TYPE: PRT
<213> ORGANISM: Artificial
<220> FEATURE:
<223> OTHER INFORMATION: Anti-TcdB sdAb

<400> SEQUENCE: 40

Gln Val Gln Leu Val Glu Ser Gly Gly Gly Leu Val Gln Pro Gly Gly
1               5                   10                  15
```

```
Ser Leu Arg Leu Ser Cys Ala Ala Ser Gly Asn Ile Phe Ser Ile Asn
            20                  25                  30

Thr Met Gly Trp Tyr Arg Gln Ala Pro Gly Lys Gln Leu Glu Leu Val
        35                  40                  45

Ala Ala Ile Thr Ser Gly Gly Thr Thr Ser Tyr Thr Asp Ser Val Glu
 50                  55                  60

Gly Arg Phe Thr Ile Ser Arg Asp Asn Ala Lys Asn Ala Val Tyr Leu
 65                  70                  75                  80

Gln Met Asn Ser Leu Lys Ala Glu Asp Thr Ala Val Tyr Tyr Cys Asn
                85                  90                  95

Thr Val Lys Val Val Gly Gly Arg Leu Asp Asn Pro Asp Tyr Trp Gly
            100                 105                 110

Gln Gly Thr Gln Val Thr Val Ser Ser
        115                 120
```

<210> SEQ ID NO 41
<211> LENGTH: 127
<212> TYPE: PRT
<213> ORGANISM: Artificial
<220> FEATURE:
<223> OTHER INFORMATION: Anti-TcdB sdAb

<400> SEQUENCE: 41

```
Gln Val Lys Leu Glu Glu Ser Gly Gly Gly Leu Val Gln Pro Gly Gly
 1               5                  10                  15

Ser Leu Arg Leu Ser Cys Ala Ala Ser Gly Arg Thr Ala Ser Gly Tyr
            20                  25                  30

Gly Met Gly Trp Phe Arg Gln Ala Pro Gly Lys Glu Arg Glu Phe Val
        35                  40                  45

Ala Ala Ile Ser Arg Ser Gly Ala Gly Thr Leu Asn Ala Asp Phe Val
 50                  55                  60

Lys Gly Arg Phe Thr Ile Ser Arg Asp Asn Ala Lys Asn Thr Val Tyr
 65                  70                  75                  80

Leu Gln Met Asn Ser Leu Lys Pro Glu Asp Thr Ala Val Tyr Tyr Cys
                85                  90                  95

Val Ala Arg Pro Thr Lys Val Asp Arg Asp Tyr Ala Thr Arg Arg Glu
            100                 105                 110

Met Tyr Asn Tyr Trp Gly Gln Gly Thr Gln Val Thr Val Ser Ser
        115                 120                 125
```

<210> SEQ ID NO 42
<211> LENGTH: 121
<212> TYPE: PRT
<213> ORGANISM: Artificial
<220> FEATURE:
<223> OTHER INFORMATION: Anti-TcdB sdAb

<400> SEQUENCE: 42

```
Gln Val Lys Leu Glu Glu Ser Gly Gly Gly Leu Val Gln Ala Gly Gly
 1               5                  10                  15

Ser Leu Arg Leu Ser Cys Ser Ala Ser Gly Arg Thr Phe Ser Ser Gly
            20                  25                  30

Val Met Gly Trp Phe Arg Gln Ala Pro Gly Lys Gln Arg Glu Leu Val
        35                  40                  45

Ala Ala Ile Thr Thr Gly Gly Ser Thr Tyr Thr Asp Ser Val Lys
 50                  55                  60

Gly Arg Phe Thr Ile Ser Arg Asp Asn Ala Lys Asn Thr Val Tyr Leu
 65                  70                  75                  80
```

```
Gln Met Asn Ser Leu Lys Pro Glu Asp Thr Ala Val Tyr Tyr Cys Asn
                85                  90                  95

Ser Val Ala Val Val Gly Gly Val Ile Lys Ser Pro Asp Tyr Trp Gly
            100                 105                 110

Gln Gly Thr Gln Val Thr Val Ser Ser
        115                 120

<210> SEQ ID NO 43
<211> LENGTH: 122
<212> TYPE: PRT
<213> ORGANISM: Artificial
<220> FEATURE:
<223> OTHER INFORMATION: Anti-TcdB sdAb

<400> SEQUENCE: 43

Gln Val Gln Leu Val Glu Ser Gly Gly Gly Ser Val Gln Ala Gly Gly
1               5                   10                  15

Ser Leu Arg Leu Ser Cys Ala Ala Ser Gly Leu Ser Arg Tyr Ala Met
            20                  25                  30

Ala Trp Phe Arg Gln Gly Thr Gly Lys Glu Arg Glu Phe Val Ala Ser
        35                  40                  45

Thr Asn Trp Ser Ser Gly Asn Thr Pro Tyr Ala Asp Ser Val Lys Gly
    50                  55                  60

Arg Phe Ile Ile Ser Arg Asp Asn Ala Lys Asn Thr Val Tyr Leu Gln
65                  70                  75                  80

Met Asn Ser Leu Lys Pro Gly Asp Thr Ala Ile Tyr Tyr Cys Ala Ala
                85                  90                  95

Arg Lys Leu Asp Val Pro Ser Arg Tyr Ser Gln His Tyr Asp Tyr Trp
            100                 105                 110

Gly Gln Gly Thr Gln Val Thr Val Ser Ser
        115                 120

<210> SEQ ID NO 44
<211> LENGTH: 121
<212> TYPE: PRT
<213> ORGANISM: Artificial
<220> FEATURE:
<223> OTHER INFORMATION: Anti-TcdB sdAb

<400> SEQUENCE: 44

Gln Val Gln Leu Val Glu Ser Gly Gly Asp Leu Val Gln Ala Gly Gly
1               5                   10                  15

Ser Leu Arg Leu Ser Cys Ala Ala Ser Gly Ser Ile Ser Arg Ile Ser
            20                  25                  30

Thr Met Gly Trp Tyr Arg Gln Ala Pro Gly Lys Gln Arg Glu Leu Val
        35                  40                  45

Ala Thr Ile Ser Thr Gly Gly Thr Thr Asn Tyr Ala Glu Ser Val Lys
    50                  55                  60

Gly Arg Phe Thr Val Ser Arg Asp Asn Ala Lys Asn Thr Met Tyr Leu
65                  70                  75                  80

Gln Met Asn Ser Leu Lys Pro Glu Asp Thr Ala Val Tyr Tyr Cys Ala
                85                  90                  95

Ala Gly Trp Lys Val Val Arg Gly Ser Leu Glu Tyr Glu Tyr Ser Gly
            100                 105                 110

Gln Gly Thr Gln Val Thr Val Ser Ser
        115                 120
```

```
<210> SEQ ID NO 45
<211> LENGTH: 125
<212> TYPE: PRT
<213> ORGANISM: Artificial
<220> FEATURE:
<223> OTHER INFORMATION: Anti-TcdA sdAb

<400> SEQUENCE: 45

Gln Val Lys Leu Glu Glu Ser Gly Gly Gly Leu Val Gln Ala Gly Gly
1               5                   10                  15

Ser Leu Arg Leu Ser Cys Ala Ala Ser Gly Arg Thr Phe Asn Thr Leu
            20                  25                  30

Ser Met Gly Trp Phe Arg Gln Ala Pro Gly Lys Glu Arg Glu Phe Val
        35                  40                  45

Cys Ala Val Ser Arg Ser Gly Gly Ser Thr Tyr Tyr Ala Asp Ser Val
    50                  55                  60

Lys Gly Arg Phe Thr Cys Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Ala Ala Thr Lys Ser Asn Thr Thr Ala Tyr Arg Leu Ser Phe
            100                 105                 110

Asp Tyr Trp Gly Gln Gly Thr Gln Val Thr Val Ser Ser
        115                 120                 125

<210> SEQ ID NO 46
<211> LENGTH: 124
<212> TYPE: PRT
<213> ORGANISM: Artificial
<220> FEATURE:
<223> OTHER INFORMATION: Anti-TcdA sdAb

<400> SEQUENCE: 46

Gln Val Lys Leu Glu Glu Ser Gly Gly Gly Leu Val Gln Ala Gly Gly
1               5                   10                  15

Ser Leu Arg Leu Ser Cys Ala Ala Ser Gly Arg Thr Phe Ser Met Tyr
            20                  25                  30

Arg Met Gly Trp Phe Arg Gln Ala Pro Gly Lys Glu Arg Glu Phe Val
        35                  40                  45

Cys Val Ile Thr Arg Asn Gly Ser Ser Thr Tyr Tyr Ala Asp Ser Val
    50                  55                  60

Lys Gly Arg Phe Thr Cys Ser Arg Asp Asn Ala Lys Asn Thr Val Tyr
65                  70                  75                  80

Leu Gln Met Asn Ser Leu Lys Pro Glu Asp Thr Ala Leu Tyr Tyr Cys
                85                  90                  95

Ala Ala Thr Ser Gly Ser Ser Tyr Leu Asp Ala Ala His Val Tyr Asp
            100                 105                 110

Tyr Trp Gly Gln Gly Thr Gln Val Thr Val Ser Ser
        115                 120

<210> SEQ ID NO 47
<211> LENGTH: 128
<212> TYPE: PRT
<213> ORGANISM: Artificial
<220> FEATURE:
<223> OTHER INFORMATION: Anti-TcdA sdAb

<400> SEQUENCE: 47

Gln Val Lys Leu Glu Glu Ser Gly Gly Gly Leu Val Gln Pro Gly Gly
1               5                   10                  15
```

-continued

Ser Leu Arg Leu Ser Cys Ala Ala Ser Gly Arg Thr Leu Ser Ser Tyr
            20                  25                  30

Ile Val Ala Trp Phe Arg Gln Ala Pro Gly Lys Glu Arg Glu Phe Val
            35                  40                  45

Cys Gly Ile Ser Arg Arg Gly Gly Asn Ser Ala Tyr Val Glu Ser Val
50                  55                  60

Lys Gly Arg Phe Thr Cys Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
            85                  90                  95

Ala Ala Asp Gly Ser Val Ala Gly Trp Gly Arg Arg Ser Val Ser Val
            100                 105                 110

Ser Ser Tyr Asp Tyr Trp Gly Gln Gly Thr Gln Val Thr Val Ser Ser
            115                 120                 125

<210> SEQ ID NO 48
<211> LENGTH: 123
<212> TYPE: PRT
<213> ORGANISM: Artificial
<220> FEATURE:
<223> OTHER INFORMATION: Anti-TcdA sdAb

<400> SEQUENCE: 48

Gln Val Gln Leu Val Glu Ser Gly Gly Gly Leu Ala Gln Ala Gly Gly
1               5                   10                  15

Ser Leu Arg Leu Ser Cys Ala Ala Ser Gly Arg Thr Phe Ser Met Asp
            20                  25                  30

Pro Met Ala Trp Phe Arg Gln Pro Pro Gly Lys Glu Arg Glu Phe Val
            35                  40                  45

Cys Ala Gly Ser Ser Thr Gly Arg Thr Thr Tyr Tyr Ala Asp Ser Val
50                  55                  60

Lys Gly Arg Phe Thr Cys Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
            85                  90                  95

Ala Ala Ala Pro Tyr Gly Ala Asn Trp Tyr Arg Asp Glu Tyr Ala Tyr
            100                 105                 110

Trp Gly Gln Gly Thr Gln Val Thr Val Ser Ser
            115                 120

<210> SEQ ID NO 49
<211> LENGTH: 124
<212> TYPE: PRT
<213> ORGANISM: Artificial
<220> FEATURE:
<223> OTHER INFORMATION: Anti-TcdA sdAb

<400> SEQUENCE: 49

Gln Val Gln Leu Val Glu Ser Gly Gly Gly Leu Val Gln Ala Gly Gly
1               5                   10                  15

Ser Leu Arg Leu Ser Cys Ala Ala Ser Ile Arg Ser Phe Ser Asn Arg
            20                  25                  30

Asn Met Gly Trp Phe Arg Gln Pro Pro Gly Lys Glu Arg Glu Phe Val
            35                  40                  45

Cys Gly Ile Ser Trp Gly Gly Ser Thr Arg Tyr Ala Asp Ser Val
50                  55                  60

Lys Gly Arg Phe Thr Cys Ser Arg Asp Asn Ala Lys Lys Thr Val Tyr

```
                65                  70                  75                  80
Leu Gln Met Asn Ser Leu Lys Pro Glu Asp Thr Ala Val Tyr Tyr Cys
                85                  90                  95

Ala Ala Glu Phe Gly His Asn Ile Ala Thr Ser Ser Asp Glu Tyr Asp
            100                 105                 110

Tyr Trp Gly Gln Gly Thr Gln Val Thr Val Ser Ser
            115                 120

<210> SEQ ID NO 50
<211> LENGTH: 124
<212> TYPE: PRT
<213> ORGANISM: Artificial
<220> FEATURE:
<223> OTHER INFORMATION: Anti-TcdA sdAb

<400> SEQUENCE: 50

Gln Val Lys Leu Glu Glu Ser Gly Gly Gly Leu Val Gln Ala Gly Gly
1               5                   10                  15

Ser Leu Arg Leu Ser Cys Ala Ala Ser Glu Arg Thr Phe Ser Arg Tyr
            20                  25                  30

Pro Val Ala Trp Phe Arg Gln Ala Pro Gly Ala Glu Arg Glu Phe Val
        35                  40                  45

Cys Val Ile Ser Ser Thr Gly Thr Ser Thr Tyr Tyr Ala Asp Ser Val
    50                  55                  60

Lys Gly Arg Phe Thr Cys Ser Arg Asp Asn Ala Lys Val Thr Val Tyr
65                  70                  75                  80

Leu Gln Met Asn Asn Leu Lys Arg Glu Asp Thr Ala Val Tyr Phe Cys
                85                  90                  95

Ala Val Asn Ser Gln Arg Thr Arg Leu Gln Asp Pro Asn Glu Tyr Asp
            100                 105                 110

Tyr Trp Gly Gln Gly Thr Gln Val Thr Val Ser Ser
            115                 120

<210> SEQ ID NO 51
<211> LENGTH: 121
<212> TYPE: PRT
<213> ORGANISM: Artificial
<220> FEATURE:
<223> OTHER INFORMATION: Anti-TcdB sdAb

<400> SEQUENCE: 51

Gln Val Gln Leu Val Glu Ser Gly Gly Gly Leu Val Gln Pro Gly Gly
1               5                   10                  15

Ser Leu Arg Leu Ser Cys Ala Ala Ser Gly Asn Ile Phe Ser Ile Asn
            20                  25                  30

Thr Met Gly Trp Tyr Arg Gln Ala Pro Gly Lys Gln Leu Glu Leu Val
        35                  40                  45

Cys Ala Ile Thr Ser Gly Gly Thr Thr Ser Tyr Thr Asp Ser Val Glu
    50                  55                  60

Gly Arg Phe Thr Cys Ser Arg Asp Asn Ala Lys Asn Ala Val Tyr Leu
65                  70                  75                  80

Gln Met Asn Ser Leu Lys Ala Glu Asp Thr Ala Val Tyr Tyr Cys Asn
                85                  90                  95

Thr Val Lys Val Val Gly Gly Arg Leu Asp Asn Pro Asp Tyr Trp Gly
            100                 105                 110

Gln Gly Thr Gln Val Thr Val Ser Ser
            115                 120
```

-continued

<210> SEQ ID NO 52
<211> LENGTH: 127
<212> TYPE: PRT
<213> ORGANISM: Artificial
<220> FEATURE:
<223> OTHER INFORMATION: Anti-TcdB sdAb

<400> SEQUENCE: 52

```
Gln Val Lys Leu Glu Glu Ser Gly Gly Gly Leu Val Gln Pro Gly Gly
1               5                   10                  15

Ser Leu Arg Leu Ser Cys Ala Ala Ser Gly Arg Thr Ala Ser Gly Tyr
            20                  25                  30

Gly Met Gly Trp Phe Arg Gln Ala Pro Gly Lys Glu Arg Glu Phe Val
        35                  40                  45

Cys Ala Ile Ser Arg Ser Gly Ala Gly Thr Leu Asn Ala Asp Phe Val
    50                  55                  60

Lys Gly Arg Phe Thr Cys Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Val Ala Arg Pro Thr Lys Val Asp Arg Asp Tyr Ala Thr Arg Arg Glu
            100                 105                 110

Met Tyr Asn Tyr Trp Gly Gln Gly Thr Gln Val Thr Val Ser Ser
        115                 120                 125
```

<210> SEQ ID NO 53
<211> LENGTH: 121
<212> TYPE: PRT
<213> ORGANISM: Artificial
<220> FEATURE:
<223> OTHER INFORMATION: Anti-TcdB sdAb

<400> SEQUENCE: 53

```
Gln Val Lys Leu Glu Glu Ser Gly Gly Gly Leu Val Gln Ala Gly Gly
1               5                   10                  15

Ser Leu Arg Leu Ser Cys Ser Ala Ser Gly Arg Thr Phe Ser Ser Gly
            20                  25                  30

Val Met Gly Trp Phe Arg Gln Ala Pro Gly Lys Gln Arg Glu Leu Val
        35                  40                  45

Cys Ala Ile Thr Thr Gly Gly Ser Thr Ser Tyr Thr Asp Ser Val Lys
    50                  55                  60

Gly Arg Phe Thr Cys Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ser Val Ala Val Val Gly Gly Val Ile Lys Ser Pro Asp Tyr Trp Gly
            100                 105                 110

Gln Gly Thr Gln Val Thr Val Ser Ser
        115                 120
```

<210> SEQ ID NO 54
<211> LENGTH: 122
<212> TYPE: PRT
<213> ORGANISM: Artificial
<220> FEATURE:
<223> OTHER INFORMATION: Anti-TcdB sdAb

<400> SEQUENCE: 54

```
Gln Val Gln Leu Val Glu Ser Gly Gly Gly Ser Val Gln Ala Gly Gly
```

```
            1               5                  10                 15
          Ser Leu Arg Leu Ser Cys Ala Ala Ser Gly Leu Ser Arg Tyr Ala Met
                          20                 25                 30

Ala Trp Phe Arg Gln Gly Thr Gly Lys Glu Arg Glu Phe Val Cys Ser
                          35                 40                 45

Thr Asn Trp Ser Ser Gly Asn Thr Pro Tyr Ala Asp Ser Val Lys Gly
              50                 55                 60

Arg Phe Ile Cys Ser Arg Asp Asn Ala Lys Asn Thr Val Tyr Leu Gln
          65                  70                 75                 80

Met Asn Ser Leu Lys Pro Gly Asp Thr Ala Ile Tyr Tyr Cys Ala Ala
                          85                 90                 95

Arg Lys Leu Asp Val Pro Ser Arg Tyr Ser Gln His Tyr Asp Tyr Trp
                          100                105                110

Gly Gln Gly Thr Gln Val Thr Val Ser Ser
                          115                120

<210> SEQ ID NO 55
<211> LENGTH: 120
<212> TYPE: PRT
<213> ORGANISM: Artificial
<220> FEATURE:
<223> OTHER INFORMATION: Anti-TcdB sdAb

<400> SEQUENCE: 55

Gln Val Gln Leu Val Glu Ser Gly Gly Asp Leu Val Gln Ala Gly Gly
          1               5                  10                 15

Ser Leu Arg Leu Ser Cys Ala Ala Ser Gly Ser Ile Ser Arg Ile Ser
                          20                 25                 30

Thr Met Gly Trp Tyr Arg Gln Ala Pro Gly Lys Gln Arg Glu Leu Cys
                          35                 40                 45

Ala Thr Ile Ser Thr Gly Gly Thr Thr Asn Tyr Ala Glu Ser Val Lys
              50                 55                 60

Gly Arg Phe Thr Cys Ser Arg Asp Asn Ala Lys Asn Thr Met Tyr Leu
          65                  70                 75                 80

Gln Met Asn Ser Leu Lys Pro Glu Asp Thr Ala Val Tyr Tyr Cys Ala
                          85                 90                 95

Ala Gly Trp Lys Val Val Arg Gly Ser Leu Glu Tyr Glu Tyr Ser Gly
                          100                105                110

Gln Gly Thr Gln Val Thr Val Ser
                          115                120

<210> SEQ ID NO 56
<211> LENGTH: 45
<212> TYPE: DNA
<213> ORGANISM: Artificial
<220> FEATURE:
<223> OTHER INFORMATION: Primer MJ1

<400> SEQUENCE: 56
gcccagccgg ccatggccsm kgtgcagctg gtggaktctg gggga            45

<210> SEQ ID NO 57
<211> LENGTH: 42
<212> TYPE: DNA
<213> ORGANISM: Artificial
<220> FEATURE:
<223> OTHER INFORMATION: Primer MJ2

<400> SEQUENCE: 57
```
cagccggcca tggcccaggt aaagctggag gagtctgggg ga                                42

<210> SEQ ID NO 58
<211> LENGTH: 45
<212> TYPE: DNA
<213> ORGANISM: Artificial
<220> FEATURE:
<223> OTHER INFORMATION: Primer MJ3

<400> SEQUENCE: 58
gcccagccgg ccatggccca ggctcaggta cagctggtgg agtct                             45

<210> SEQ ID NO 59
<211> LENGTH: 23
<212> TYPE: DNA
<213> ORGANISM: Artificial
<220> FEATURE:
<223> OTHER INFORMATION: Primer CH2

<400> SEQUENCE: 59
chcgccatca aggtaccagt tga                                                     23

<210> SEQ ID NO 60
<211> LENGTH: 30
<212> TYPE: DNA
<213> ORGANISM: Artificial
<220> FEATURE:
<223> OTHER INFORMATION: Primer CH2b3

<400> SEQUENCE: 60
chbggtacct gtcatccacg gaccagctga                                              30

<210> SEQ ID NO 61
<211> LENGTH: 34
<212> TYPE: DNA
<213> ORGANISM: Artificial
<220> FEATURE:
<223> OTHER INFORMATION: Primer MJ7

<400> SEQUENCE: 61
catgtgtaga ctcgcggccc agccggccat ggcc                                         34

<210> SEQ ID NO 62
<211> LENGTH: 47
<212> TYPE: DNA
<213> ORGANISM: Artificial
<220> FEATURE:
<223> OTHER INFORMATION: Primer MJ8

<400> SEQUENCE: 62
catgtgtaga ttcctggccg gcctggcctg aggagacggt gacctgg                           47

<210> SEQ ID NO 63
<211> LENGTH: 38
<212> TYPE: DNA
<213> ORGANISM: Artificial
<220> FEATURE:
<223> OTHER INFORMATION: Bbsl1-VHH sense primer

<400> SEQUENCE: 63
tatgaagaca ccaggcccag gtaaagctgg aggagtct                                     38

<210> SEQ ID NO 64
<211> LENGTH: 38
<212> TYPE: DNA
<213> ORGANISM: Artificial

<220> FEATURE:
<223> OTHER INFORMATION: Bbsl2-VHH sense primer

<400> SEQUENCE: 64
tatgaagaca ccaggcccag gtgcagctgg tggagtct           38

<210> SEQ ID NO 65
<211> LENGTH: 30
<212> TYPE: DNA
<213> ORGANISM: Artificial
<220> FEATURE:
<223> OTHER INFORMATION: BamHI-VHH antisense primer

<400> SEQUENCE: 65
ttgttcggat cctgaggaga cggtgacctg           30

<210> SEQ ID NO 66
<211> LENGTH: 17
<212> TYPE: DNA
<213> ORGANISM: Artificial
<220> FEATURE:
<223> OTHER INFORMATION: Primer M13FP

<400> SEQUENCE: 66
gtaaaacgac ggccagt           17

<210> SEQ ID NO 67
<211> LENGTH: 17
<212> TYPE: DNA
<213> ORGANISM: Artificial
<220> FEATURE:
<223> OTHER INFORMATION: Primer M13RP

<400> SEQUENCE: 67
caggaaacag ctatgac           17

<210> SEQ ID NO 68
<211> LENGTH: 52
<212> TYPE: DNA
<213> ORGANISM: Artificial
<220> FEATURE:
<223> OTHER INFORMATION: Primer A4.2mR-Cys

<400> SEQUENCE: 68
agtctgcata gtatgtgcta ccaccactcc ggctaacagc gcaaacaaac tc           52

<210> SEQ ID NO 69
<211> LENGTH: 52
<212> TYPE: DNA
<213> ORGANISM: Artificial
<220> FEATURE:
<223> OTHER INFORMATION: Primer A4.2mF-Cys

<400> SEQUENCE: 69
tagcacatac tatgcagact ccgtgaaggg ccgattcacc tgctccagag ac           52

<210> SEQ ID NO 70
<211> LENGTH: 52
<212> TYPE: DNA
<213> ORGANISM: Artificial
<220> FEATURE:
<223> OTHER INFORMATION: Primer A5.1mR-Cys

<400> SEQUENCE: 70
agtctgcata gtatgtgcta ctaccattcc gggtaataac gcatacaaac tc           52

<210> SEQ ID NO 71
<211> LENGTH: 52
<212> TYPE: DNA
<213> ORGANISM: Artificial
<220> FEATURE:
<223> OTHER INFORMATION: Primer A19.2mR-Cys

<400> SEQUENCE: 71
actctacata ggcactatta ccaccacgcc ggctaatacc gcatacaaac tc         52

<210> SEQ ID NO 72
<211> LENGTH: 52
<212> TYPE: DNA
<213> ORGANISM: Artificial
<220> FEATURE:
<223> OTHER INFORMATION: Primer A19.2mF-Cys

<400> SEQUENCE: 72
taatagtgcc tatgtagagt ccgtgaaggg ccgattcacc tgctccagag ac         52

<210> SEQ ID NO 73
<211> LENGTH: 40
<212> TYPE: DNA
<213> ORGANISM: Artificial
<220> FEATURE:
<223> OTHER INFORMATION: Primer A20.1mSfil-F

<400> SEQUENCE: 73
accgttgcgc aggcccagcc ggccatggcc caggtacagc                       40

<210> SEQ ID NO 74
<211> LENGTH: 52
<212> TYPE: DNA
<213> ORGANISM: Artificial
<220> FEATURE:
<223> OTHER INFORMATION: Primer A20.1mR-Cys

<400> SEQUENCE: 74
tgtctgcata gtatgtggtc cgccccgtag aactccccgc gcatacaaac tc         52

<210> SEQ ID NO 75
<211> LENGTH: 52
<212> TYPE: DNA
<213> ORGANISM: Artificial
<220> FEATURE:
<223> OTHER INFORMATION: Primer A20.1 mF-Cys

<400> SEQUENCE: 75
gaccacatac tatgcagaca gcgtgaaggg ccgattcacc tgctccagag ac         52

<210> SEQ ID NO 76
<211> LENGTH: 41
<212> TYPE: DNA
<213> ORGANISM: Artificial
<220> FEATURE:
<223> OTHER INFORMATION: Primer A20.1mSfil-R

<400> SEQUENCE: 76
gttcggatcc ctggccggcc tggcctgagg agacggtgac c                     41

<210> SEQ ID NO 77
<211> LENGTH: 52
<212> TYPE: DNA
<213> ORGANISM: Artificial
<220> FEATURE:
<223> OTHER INFORMATION: Primer A24.1mR-Cys

```
<400> SEQUENCE: 77
agtctgcata gcgtgtgcta cctccacccc agctaatacc gcatacaaac tc          52

<210> SEQ ID NO 78
<211> LENGTH: 52
<212> TYPE: DNA
<213> ORGANISM: Artificial
<220> FEATURE:
<223> OTHER INFORMATION: Primer A24.1mF-Cys

<400> SEQUENCE: 78
tagcacacgc tatgcagact ccgtgaaggg ccgattcacc tgctccagag ac          52

<210> SEQ ID NO 79
<211> LENGTH: 52
<212> TYPE: DNA
<213> ORGANISM: Artificial
<220> FEATURE:
<223> OTHER INFORMATION: Primer A26.8mR-Cys

<400> SEQUENCE: 79
agtctgcata gtatgtgctc gtaccagtcg agctaataac gcatacaaac tc          52

<210> SEQ ID NO 80
<211> LENGTH: 52
<212> TYPE: DNA
<213> ORGANISM: Artificial
<220> FEATURE:
<223> OTHER INFORMATION: Primer A26.8mF-Cys

<400> SEQUENCE: 80
gagcacatac tatgcagact cggtgaaggg ccggttcacc tgctccagag ac          52

<210> SEQ ID NO 81
<211> LENGTH: 8
<212> TYPE: PRT
<213> ORGANISM: Artificial
<220> FEATURE:
<223> OTHER INFORMATION: Tryptic peptide

<400> SEQUENCE: 81

Glu Phe Val Cys Ala Val Ser Arg
1               5

<210> SEQ ID NO 82
<211> LENGTH: 8
<212> TYPE: PRT
<213> ORGANISM: Artificial
<220> FEATURE:
<223> OTHER INFORMATION: Tryptic peptide

<400> SEQUENCE: 82

Glu Phe Val Cys Val Ile Thr Arg
1               5

<210> SEQ ID NO 83
<211> LENGTH: 8
<212> TYPE: PRT
<213> ORGANISM: Artificial
<220> FEATURE:
<223> OTHER INFORMATION: Tryptic peptide

<400> SEQUENCE: 83

Glu Phe Val Cys Gly Ile Ser Arg
1               5
```

<210> SEQ ID NO 84
<211> LENGTH: 11
<212> TYPE: PRT
<213> ORGANISM: Artificial
<220> FEATURE:
<223> OTHER INFORMATION: Tryptic peptide

<400> SEQUENCE: 84

Glu Phe Val Cys Ala Gly Ser Ser Thr Gly Arg
1               5                   10

<210> SEQ ID NO 85
<211> LENGTH: 14
<212> TYPE: PRT
<213> ORGANISM: Artificial
<220> FEATURE:
<223> OTHER INFORMATION: Tryptic peptide

<400> SEQUENCE: 85

Glu Phe Val Cys Gly Ile Ser Trp Gly Gly Gly Ser Thr Arg
1               5                   10

<210> SEQ ID NO 86
<211> LENGTH: 20
<212> TYPE: PRT
<213> ORGANISM: Artificial
<220> FEATURE:
<223> OTHER INFORMATION: Tryptic peptide

<400> SEQUENCE: 86

Glu Phe Val Cys Val Ile Ser Ser Thr Gly Thr Ser Thr Tyr Tyr Ala
1               5                   10                  15

Asp Ser Val Lys
            20

<210> SEQ ID NO 87
<211> LENGTH: 5
<212> TYPE: PRT
<213> ORGANISM: Artificial
<220> FEATURE:
<223> OTHER INFORMATION: Tryptic peptide

<400> SEQUENCE: 87

Phe Thr Cys Ser Arg
1               5

<210> SEQ ID NO 88
<211> LENGTH: 124
<212> TYPE: PRT
<213> ORGANISM: Artificial
<220> FEATURE:
<223> OTHER INFORMATION: Anti-TcdA sdAb A1.3

<400> SEQUENCE: 88

Gln Val Lys Leu Glu Glu Ser Gly Gly Gly Leu Val Gln Ala Gly Gly
1               5                   10                  15

Ser Leu Arg Leu Ser Cys Ala Ala Ser Ile Arg Ser Phe Ser Tyr Arg
            20                  25                  30

Asn Met Gly Trp Phe Arg Gln Ala Pro Gly Lys Glu Arg Glu Phe Val
        35                  40                  45

Ala Ala Ile Thr Trp Asp Gly Gly Ser Thr Arg Tyr Ala Asp Ser Val
    50                  55                  60

Lys Gly Arg Phe Thr Ile Ser Arg Asp Asn Ala Lys Asn Thr Val Tyr

```
                65                  70                  75                  80
Leu Gln Met Asn Ser Leu Lys Pro Glu Asp Thr Ala Val Tyr Tyr Cys
                85                  90                  95

Ala Ala Gly Phe Gly His Thr Leu Ala Thr Ser Ser Asp Glu Tyr Asp
            100                 105                 110

Tyr Trp Gly Gln Gly Thr Gln Val Thr Val Ser Ser
        115                 120
```

<210> SEQ ID NO 89
<211> LENGTH: 125
<212> TYPE: PRT
<213> ORGANISM: ARTIFICIAL
<220> FEATURE:
<223> OTHER INFORMATION: Anti-TcdB sdAb B13.2

<400> SEQUENCE: 89

```
Gln Val Lys Leu Glu Glu Ser Gly Gly Gly Leu Val Gln Ala Gly Gly
1               5                   10                  15

Ser Leu Arg Leu Ser Cys Ala Ala Ser Gly Arg Asp Phe Ser Thr Leu
            20                  25                  30

Ala Met Gly Trp Phe Arg Gln Ala Pro Gly Lys Glu Arg Glu Phe Val
        35                  40                  45

Ala Thr Ile Asn Trp Ser Gly Gly Thr Thr His Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Gly Ser Leu Lys Pro Glu Asp Thr Ala Val Tyr Tyr Cys
                85                  90                  95

Gly Arg Ser Lys Tyr Ala Ala Gly Ala Leu Thr Arg Ala Tyr Asp Tyr
            100                 105                 110

Asn Tyr Trp Gly Gln Gly Thr Gln Val Thr Val Ser Ser
        115                 120                 125
```

<210> SEQ ID NO 90
<211> LENGTH: 124
<212> TYPE: PRT
<213> ORGANISM: ARTIFICIAL
<220> FEATURE:
<223> OTHER INFORMATION: Anti-TcdB sdAb 13.3

<400> SEQUENCE: 90

```
Gln Val Lys Leu Glu Glu Ser Gly Gly Gly Leu Val Gln Pro Gly Gly
1               5                   10                  15

Ser Leu Arg Leu Ser Cys Ser Ala Ser Gly Ser Ile Phe Ser Ile Asn
            20                  25                  30

Asp Met Gly Trp Tyr Arg Arg Ala Pro Gly Lys Arg Arg Glu Leu Val
        35                  40                  45

Ala Ala Ile Thr Ser Gly Gly Ile Pro Asn Tyr Ala Asp Ser Val Lys
    50                  55                  60

Gly Arg Phe Thr Ile Ser Arg Asp Asn Ala Lys Asn Thr Gly Tyr Leu
65                  70                  75                  80

Gln Met Asn Ser Leu Lys Pro Glu Asp Thr Ala Val Tyr Tyr Cys Ala
                85                  90                  95

Ala Gln Phe Gly Thr Val Ala Ala Ala Leu Arg Arg His Glu Tyr Asp
            100                 105                 110

Tyr Trp Gly Gln Gly Thr Gln Val Thr Val Ser Ser
        115                 120
```